US007141053B2

(12) United States Patent
Rosa et al.

(10) Patent No.: US 7,141,053 B2
(45) Date of Patent: *Nov. 28, 2006

(54) METHODS OF MINIMALLY INVASIVE UNICOMPARTMENTAL KNEE REPLACEMENT

(75) Inventors: Richard A. Rosa, Short Hills, NJ (US); Vernon R. Hartdegen, Collierville, TN (US); Eric A. Stookey, Cordova, TN (US); Brian R. Harris, Jr., Cordova, TN (US); Robert M Fencl, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 365 days.

This patent is subject to a terminal disclaimer.

(21) Appl. No.: 10/305,369

(22) Filed: Nov. 27, 2002

(65) Prior Publication Data

US 2003/0100906 A1 May 29, 2003

Related U.S. Application Data

(60) Provisional application No. 60/333,488, filed on Nov. 28, 2001.

(51) Int. Cl.
*A61F 5/00* (2006.01)
*A61B 17/58* (2006.01)

(52) U.S. Cl. .................. 606/86; 606/87; 606/88
(58) Field of Classification Search ............ 606/86, 606/87, 88, 79
See application file for complete search history.

(56) References Cited

U.S. PATENT DOCUMENTS 3,852,830 A * 12/1974 Marmor ............... 623/20.3

| 4,421,112 A | 12/1983 | Mains et al. |
| 4,467,801 A | 8/1984 | Whiteside |
| 4,502,483 A | 3/1985 | Lacey |
| 4,509,511 A | 4/1985 | Neufeld |
| 4,524,766 A | 6/1985 | Petersen |
| 4,567,886 A | 2/1986 | Petersen |
| 4,574,794 A | 3/1986 | Cooke et al. |
| 4,703,751 A | 11/1987 | Pohl |
| 4,718,413 A | 1/1988 | Johnson |
| 4,719,908 A | 1/1988 | Averill et al. |
| 4,773,407 A | 9/1988 | Petersen |
| 4,787,383 A | 11/1988 | Kenna |
| 4,841,975 A | 6/1989 | Woolson |
| 4,926,847 A | 5/1990 | Luckman |
| 5,059,196 A | 10/1991 | Coates |
| 5,098,436 A | 3/1992 | Ferrante et al. |
| 5,100,409 A | 3/1992 | Coates et al. |

(Continued)

FOREIGN PATENT DOCUMENTS

DE 250255 8/1912

(Continued)

*Primary Examiner*—Pedro Philogene

(57) ABSTRACT

A method of minimally invasive unicompartmental knee replacement includes accessing a knee through a minimal incision, forming a planar surface along a tibial plateau of the knee, forming a planar posterior surface along a posterior aspect of the corresponding femoral condyle, resurfacing a distal aspect of the femoral condyle to form a resurfaced area having a curved portion, implanting a prosthetic tibial component on the planar surface along the tibial plateau and implanting a prosthetic femoral component on the prepared surface of the femoral condyle formed by the planar posterior surface and the resurfaced area. The curved portion of the resurfaced area has an anterior-posterior curvature corresponding to a fixation surface of the prosthetic femoral component. Prior to implantation, the femur and tibia are prepared to receive fixation structure of the femoral and tibial components.

29 Claims, 30 Drawing Sheets

U.S. PATENT DOCUMENTS

| | | |
|---|---|---|
| 5,122,144 A | 6/1992 | Bert et al. |
| 5,171,244 A | 12/1992 | Caspari et al. |
| 5,228,459 A | 7/1993 | Caspari et al. |
| 5,234,433 A | 8/1993 | Bert et al. |
| 5,263,498 A | 11/1993 | Caspari et al. |
| 5,304,181 A | 4/1994 | Caspari et al. |
| 5,312,411 A | 5/1994 | Steele et al. |
| 5,364,402 A * | 11/1994 | Mumme et al. ............... 606/88 |
| 5,395,376 A | 3/1995 | Caspari et al. |
| 5,423,822 A * | 6/1995 | Hershberger et al. ......... 606/79 |
| 5,486,180 A | 1/1996 | Dietz et al. |
| 5,514,139 A | 5/1996 | Goldstein et al. |
| 5,520,695 A | 5/1996 | Luckman |
| 5,569,259 A | 10/1996 | Ferrante et al. |
| 5,597,379 A | 1/1997 | Haines et al. |
| 5,643,272 A | 7/1997 | Haines et al. |
| 5,662,656 A | 9/1997 | White |
| 5,704,941 A | 1/1998 | Jacober et al. |
| 5,709,689 A | 1/1998 | Ferrante et al. |
| 5,810,827 A | 9/1998 | Haines et al. |
| 6,024,746 A | 2/2000 | Katz |
| 6,056,754 A | 5/2000 | Haines et al. |
| 6,059,831 A | 5/2000 | Braslow et al. |
| 6,102,954 A | 8/2000 | Albrektsson et al. |
| 6,468,280 B1 | 10/2002 | Saenger et al. |
| 6,554,838 B1 * | 4/2003 | McGovern et al. ........... 606/87 |
| 2002/0029038 A1 | 3/2002 | Haines |
| 2003/0100907 A1 * | 5/2003 | Rosa et al. .................... 606/86 |

FOREIGN PATENT DOCUMENTS

| | | |
|---|---|---|
| FR | 1083013 | 1/1955 |
| FR | 2 726 458 A1 | 11/1994 |

* cited by examiner

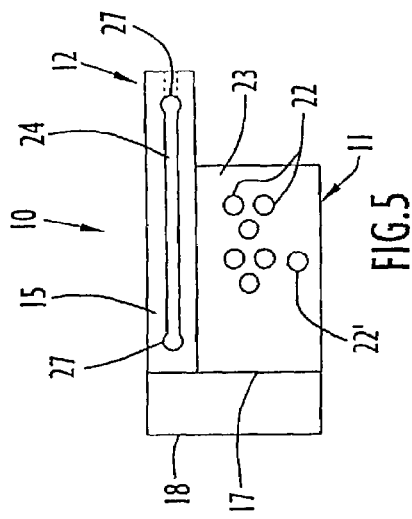
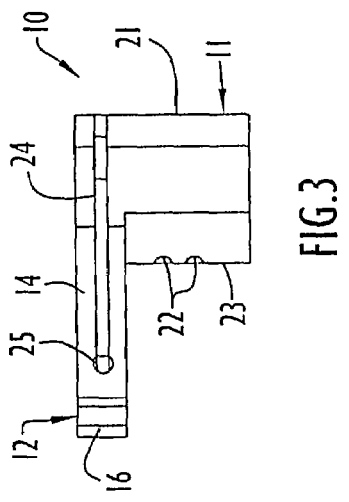
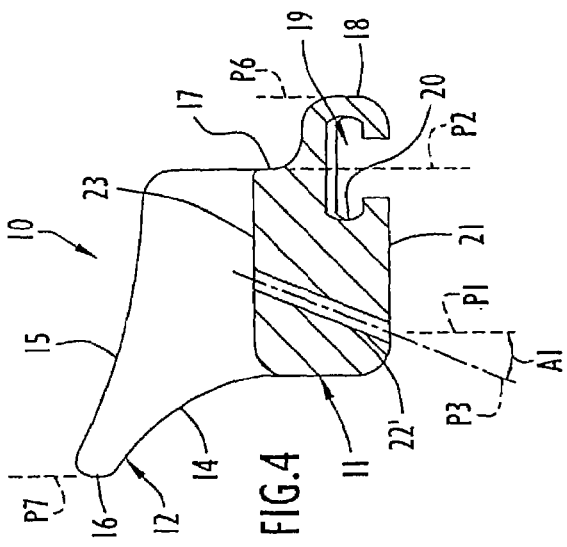
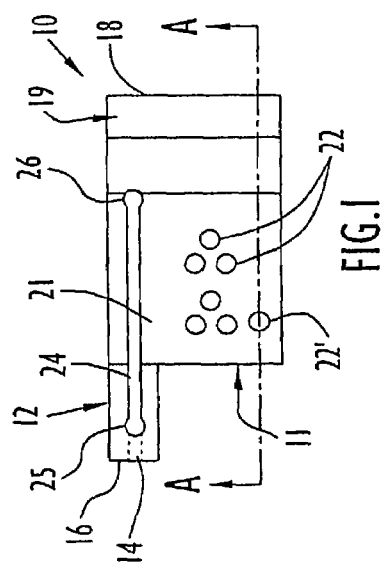
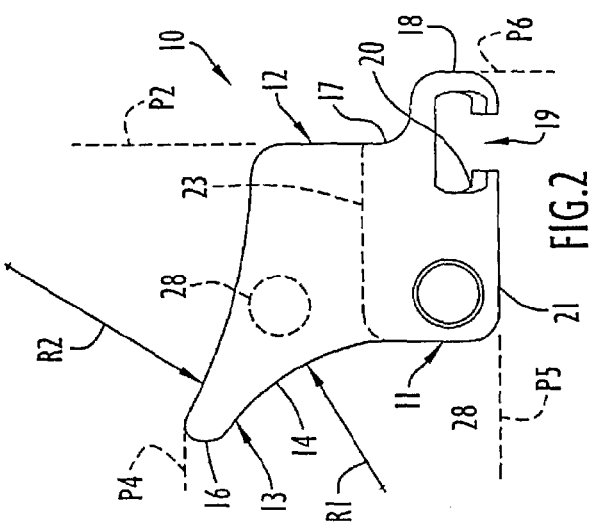

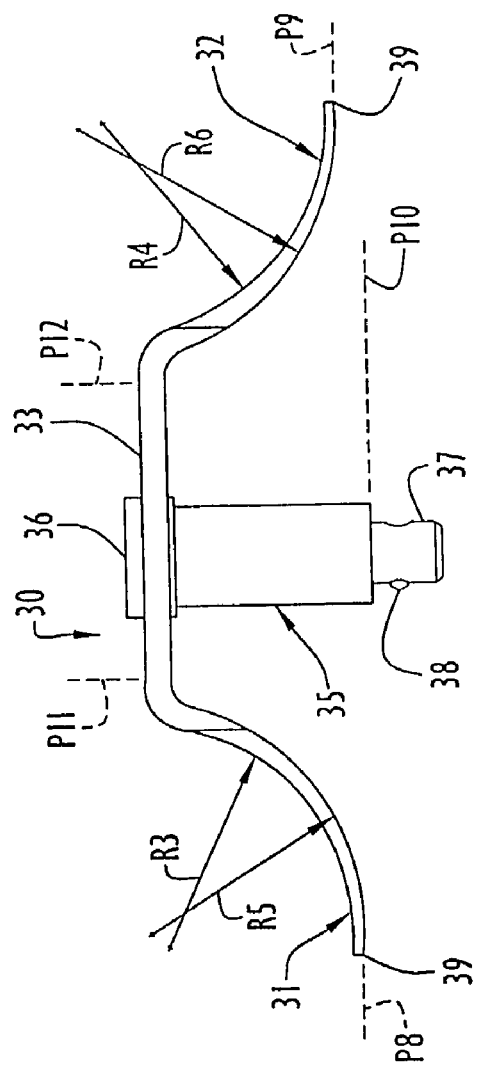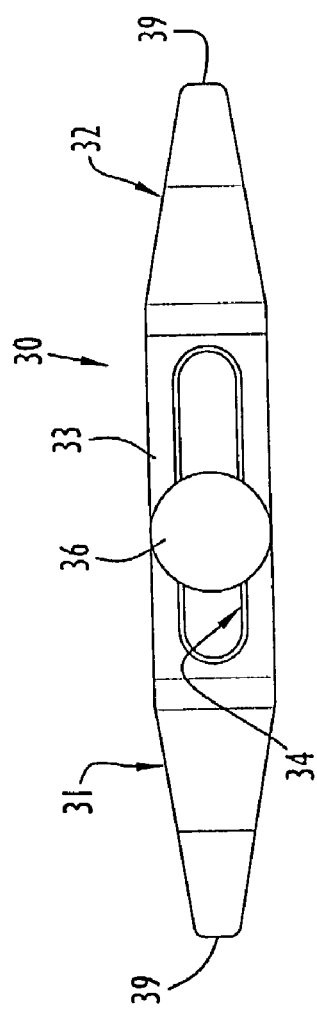
FIG.6
FIG.7

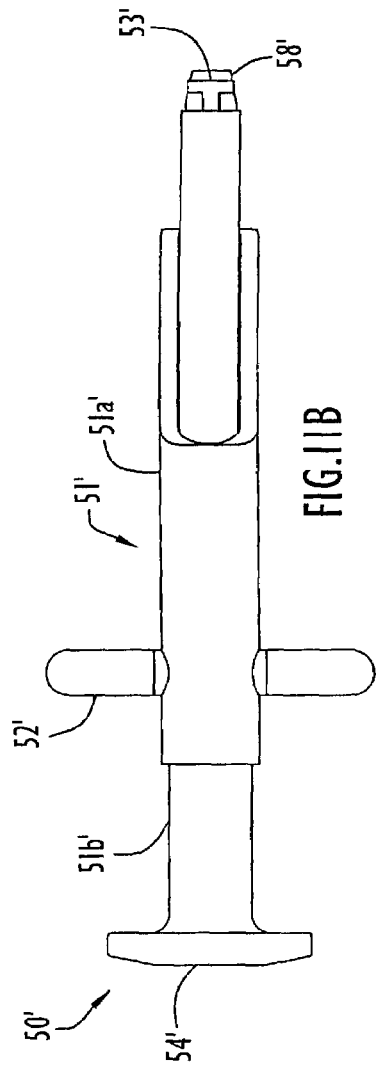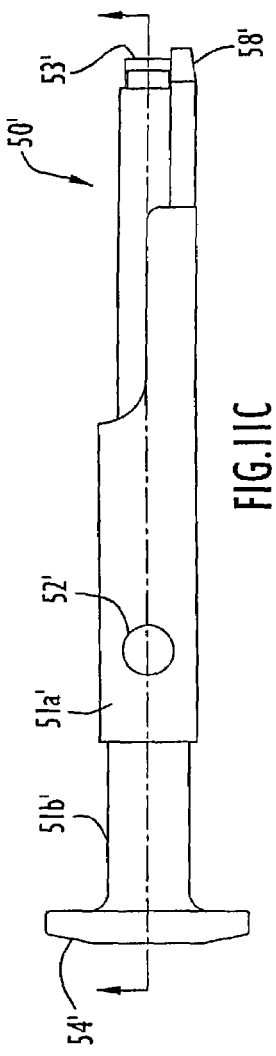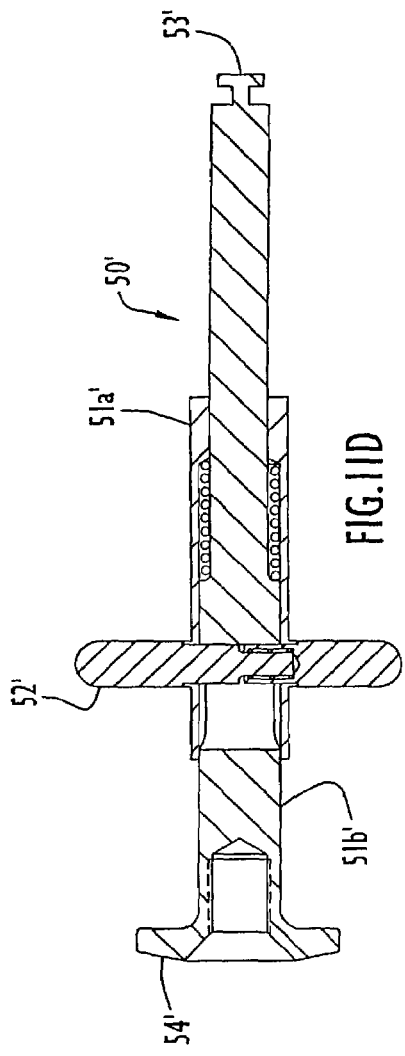

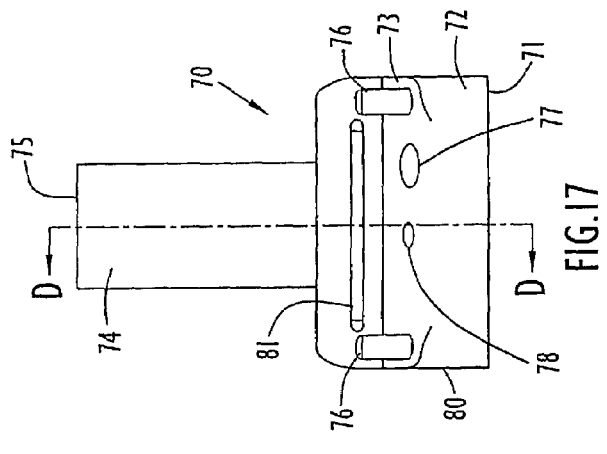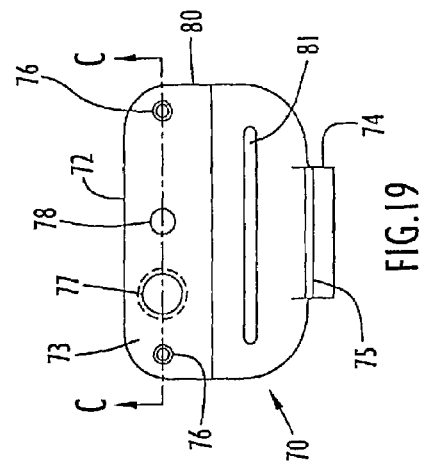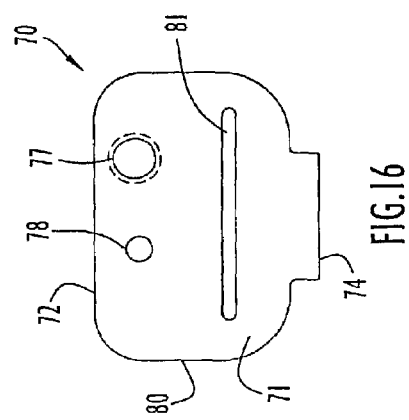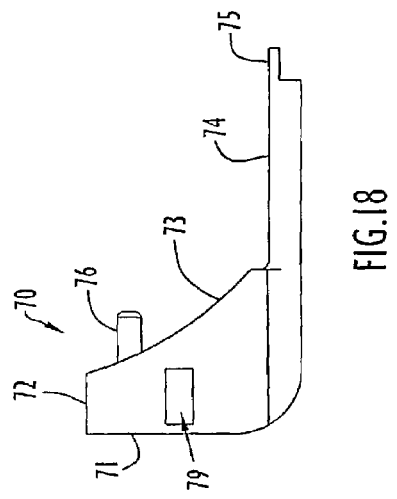

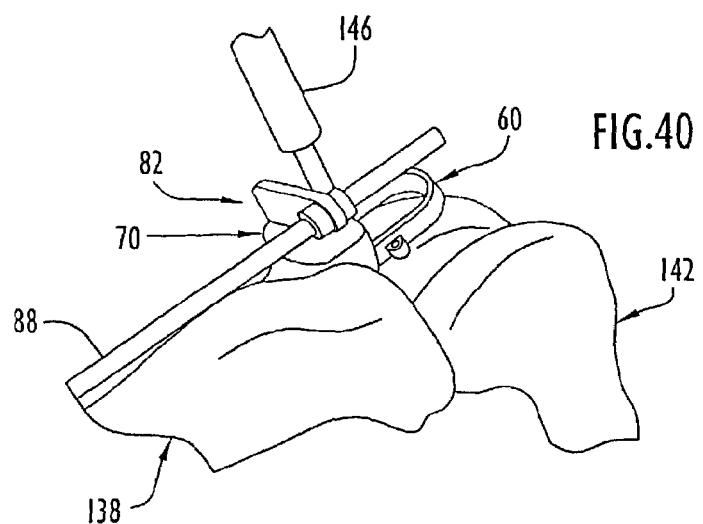
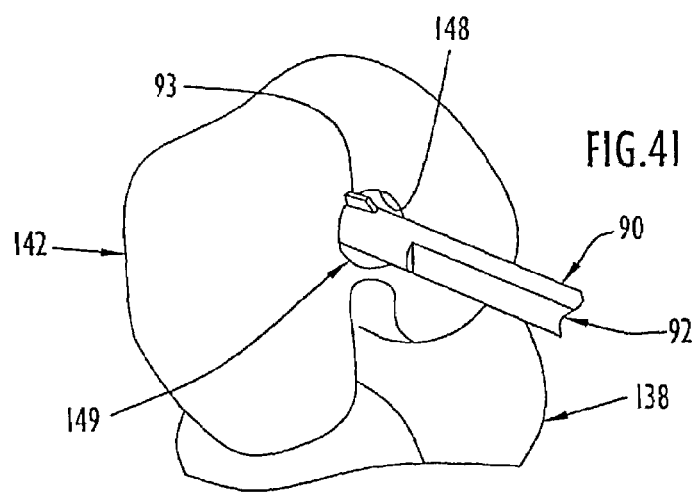
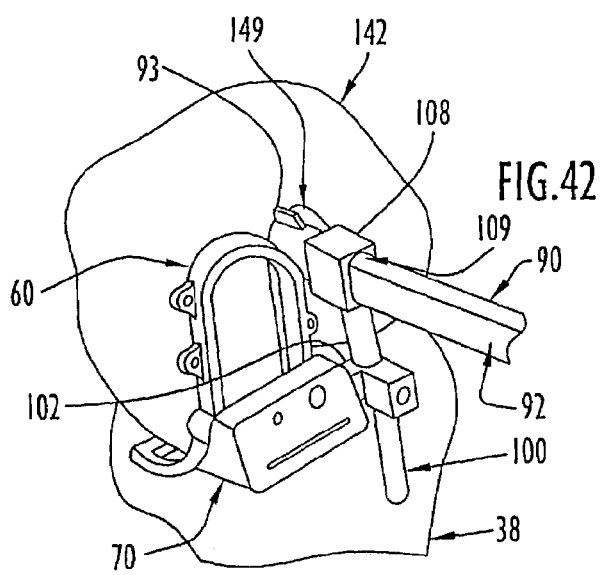

METHODS OF MINIMALLY INVASIVE UNICOMPARTMENTAL KNEE REPLACEMENT

CROSS-REFERENCE TO RELATED PATENT APPLICATIONS

This application claims priority from prior provisional patent application Ser. No. 60/333,488 filed Nov. 28, 2001, the entire disclosure of which is incorporated herein by reference. This application is related to the co-pending non-provisional patent applications filed concurrently herewith and entitled Knee Joint Prostheses (Ser. No. 10/305,370) and Instrumentation for Minimally Invasive Unicompartmental Knee Replacement (Ser. No. 10/305,371), the entire disclosures of which are incorporated herein by reference.

BACKGROUND OF THE INVENTION

1. Field of the Invention

The present invention relates generally to knee replacement procedures and, more particularly, to methods of minimally invasive unicompartmental knee replacement.

2. Brief Description of the Related Art

Prosthetic knee joint components are increasingly used to repair knee joints damaged by trauma and/or disease. Basically, the natural knee joint includes an upper or proximal part of the tibia, constituted by the medial and lateral tibial plateaus, a lower or distal part of the femur, constituted by the medial and lateral femoral condyles, and menisci between the tibial plateaus and the femoral condyles along with the patella which covers the anterior surface of the knee. The type of prosthesis implanted in the knee must be matched to the needs of the patient and may involve total knee replacement or arthroplasty in which both femoral condyles and both tibial plateaus are surgically restored using appropriate femoral and tibial prosthetic components. Depending on the particular patient, unicompartmental or partial knee replacement or arthroplasty may be preferable to total knee replacement and involves implantation of femoral and tibial prosthetic components on either the medial or lateral portion of the tibial-femoral joint while preserving more of the normal remaining anatomical structure in the knee. Both total and unicompartmental knee joint replacement procedures involve preparing the bone surfaces of the femoral condyle and the tibial plateau to receive the corresponding prosthetic components. It is very important in both total and unicompartmental knee joint replacement procedures that the bone surfaces be prepared accurately and at the proper location to ensure that the implanted prosthetic components achieve replication as close as possible to the natural knee joint.

Where unicompartmental knee replacement is preferable to total knee replacement, it is desirable that unicompartmental knee replacement be accomplished with minimal bone removal so that sufficient bone remains for potential future surgical intervention, such as future total knee replacement. Unicompartmental knee replacement may be a viable interim procedure to delay the need for a total knee replacement in many patients, since it is easier to later revise a unicompartmental knee replacement to a total knee replacement than it is to revise a total knee replacement to another total knee replacement. Other advantages of unicompartmental knee replacement over total knee replacement include easier recuperations and quicker recovery times for patients, decreased hospital stays, elimination of the need for formal physical therapy in many patients after hospital discharge, retention of the cruciate ligaments, preservation of nearly normal kinematics, and use of minimally invasive incisions to access the operative site.

Unfortunately, conventional unicompartmental knee replacement techniques are very technically demanding and the instrumentation and prostheses used in conventional unicompartmental knee replacements have various drawbacks such that reproducible clinical results are difficult to attain. Many conventional unicompartmental knee replacement procedures and instrumentation involve relatively large incisions with significant exposure, greater intramedullary invasiveness, poor alignment and reproducibility, and/or inaccurate bone preparation. The instrumentation used in many prior unicompartmental knee replacement procedures is inapplicable to minimally invasive surgery. Unicompartmental knee replacement systems designed for minimal exposure have historically provided limited instrumentation, making reproducible alignment difficult, or bulky instrumentation, which requires more intrusive surgery. Furthermore, conventional unicompartmental knee replacement procedures typically involve significant bone removal such that quality bone must be unduly sacrificed.

Various instruments have been proposed for use in knee replacement procedures to provide alignment and/or bone cutting for femoral and tibial bone preparation. Such instruments are represented by U.S. Pat. No. 4,502,483 to Lacey, U.S. Pat. Nos. 4,524,766 and 4,567,886 to Petersen, U.S. Pat. No. 4,574,794 to Cooke et al, U.S. Pat. No. 4,718,413 to Johnson, U.S. Pat. No. 4,773,407 to Petersen, U.S. Pat. No. 4,787,383 to Kenna, U.S. Pat. No. 4,926,847 to Luckman, U.S. Pat. No. 5,098,436 to Ferrante et al, U.S. Pat. No. 5,100,409 to Coates et al, U.S. Pat. No. 5,122,144 to Bert et al, U.S. Pat. Nos. 5,171,244 and 5,228,459 to Caspari, U.S. Pat. No. 5,234,433 to Bert et al, U.S. Pat. Nos. 5,263,498 and 5,304,181 to Caspari et al, U.S. Pat. No. 5,312,411 to Steele et al, U.S. Pat. No. 5,395,376 to Caspari et al, U.S. Pat. No. 5,520,695 to Luckman, U.S. Pat. No. 5,569,259 to Ferrante et al, U.S. Pat. No. 5,662,656 to White, U.S. Pat. No. 5,709,689 to Ferrante et al, U.S. Pat. No. 6,059,831 to Braslow et al, and U.S. Pat. No. 6,102,954 to Albrektsson et al, the Biomet Repicci II, the MIS Minimally Invasive Solution of Zimmer, Inc., and the Johnson & Johnson P.F.C. In many cases, femoral preparation involves forming a plurality of planar angled or chamfered resections. The Braslow et al and Luckman '695 patents are, for example, illustrative of this type of femoral preparation. The need to implement a plurality of planar angled cuts in the femur in order to accommodate the prosthetic femoral component is disadvantageous for the relatively large quantity of bone that must be removed. U.S. Pat. No. 4,719,908 to Averill et al describes contouring the femur using a cutter and a contouring guide to obtain a contour that minimizes the amount of bone removed from the femoral condyle. However, placement of the contouring guide depends for accuracy on the location of holes previously formed in the condyle to receive fixation posts of the femoral component.

The Biomet Repicci II, the MIS Minimally Invasive Solution of Zimmer, Inc., and the Johnson & Johnson P.F.C. relate to unicompartmental knee replacement procedures and instrumentation but present various disadvantages. The Biomet Repicci II knee replacement procedure lacks alignment instrumentation and requires a completely freehand burring technique to shape the femoral condyle. In addition, a pegless tibial base must be placed completely in a pocket of the cancellous bone. The MIS knee replacement procedure involves full femoral and tibial resections, incorporates a difficult implantation technique and requires invasive intramedullary alignment. The Johnson & Johnson P.F.C. knee replacement procedure fails to provide minimally invasive instrumentation and requires full femoral and tibial resections.

Accordingly, the need exists for instruments and methods for unicompartmental knee replacement which provide a conservative approach in terms of bone removal and exposure while providing consistent alignment and reproducible clinical results in a minimal incision technique. There is a need for better instrumentation and for a unicompartmental knee replacement procedure utilizing such instrumentation in a minimally invasive technique while providing the alignment needed to produce consistent, repeatable outcomes.

SUMMARY OF THE INVENTION

Accordingly, it is a primary object of the present invention to overcome the above-mentioned disadvantages of prior methods of unicompartmental knee replacement and of instruments used in prior methods of unicompartmental knee replacement.

Another object of the present invention is to remove a minimal amount of bone to accommodate a knee joint prosthesis in a unicompartmental knee replacement procedure performed through a minimal incision.

A further object of the present invention is to promote stable and secure fixation of prosthetic femoral and tibial components to bone in a unicompartmental knee replacement procedure.

An additional object of the present invention is to accurately establish the areas of a femoral condyle and a tibial plateau to be prepared to receive a knee joint prosthesis in a unicompartmental knee replacement procedure.

The present invention has as another object to externally delineate an area of a femoral condyle to be resurfaced to receive a prosthetic femoral component.

The present invention also has as an object to controllably resurface a femoral condyle to have a contour corresponding to the contour of a fixation surface of a prosthetic femoral component in a unicompartmental knee replacement procedure.

It is also an object of the present invention to prepare a femoral condyle to receive a prosthetic femoral component by removing cartilage and/or bone from the condyle to match an angular sweep of the femoral component in a coronal plane.

It is a further object of the present invention to prepare a femoral condyle to receive a prosthetic femoral component by removing cartilage and/or bone from the condyle to match a plurality of tangential radii of a fixation surface of the femoral component in a sagittal plane.

Additionally, it is an object of the present invention to controllably resurface a portion of a femoral condyle in a unicompartmental knee replacement procedure while essentially retaining the anatomic geometry of the femoral condyle portion.

Yet another object of the present invention is to maintain accuracy in bone preparation and in locating a knee joint prosthesis on the prepared bone surfaces within the confines of limited access available at the knee joint in a minimally invasive unicompartmental knee replacement procedure.

A still further object of the present invention is to utilize a minimum number of instrument components and steps of limited complexity in carrying out unicompartmental knee joint replacement.

It is also an object of the present invention to prepare a femoral condyle to facilitate anatomical femoral-tibial tracking of a knee joint prosthesis in a unicompartmental knee replacement procedure.

Moreover, it is an object of the present invention to provide a femoral resurfacing guide and posterior resection block for consistent alignment and reproducible preparation of a femoral condyle in unicompartmental knee replacement procedures.

The present invention has as an additional object to provide a resurfacing instrument and resurfacing guide for externally delineating and controllably resurfacing an area of a femoral condyle to obtain precision implant fit with minimal exposure in unicompartmental knee replacement procedures.

Still another object of the present invention is to simplify and facilitate application of a tibial cutting guide and/or tibial stylus in small incision unicompartmental knee replacement procedures.

Yet a further object of the present invention is to facilitate preparation of the proximal tibia to receive a posterior tibial fixation peg within the confines of a small incision in unicompartmental knee replacement procedures.

It is another object of the present invention to promote reproducible, accurate bone preparation in unicompartmental knee replacement procedures.

Additionally, the present invention has as an object to enhance reproducible, proper alignment between prosthetic femoral and tibial components in unicompartmental knee replacement procedures.

Some of the advantages of the present invention are that the unicompartmental knee replacement procedures and instrumentation may be used in minimally invasive procedures as well as in open surgical procedures, sufficient access for the unicompartmental knee replacement procedures and instrumentation may be established through a three to four inch incision, bone is conserved and particularly about twenty percent more quality bone stock may be conserved in the femur, surgical time is significantly reduced, implant placement is consistent and accurate so that each implanted knee tracks anatomically, the need for hand-sculpting and/or eyeball judgement when preparing the bone surfaces is/are avoided, the opportunity for surgical error is reduced, the femoral resurfacing guide provides soft tissue retraction and retraction of the patella for enhanced surgical exposure, the femoral resurfacing guide has a stylus to facilitate proper positioning on the bone and to provide an indication of where the prosthetic femoral component will transition into the bone, the posterior resection block cooperates with a resected surface of the tibial plateau to ensure that a resection slot of the posterior resection block is parallel to the resected tibial surface, various tissue removing instruments can be used with the different femoral resurfacing guides, the femoral resurfacing guides may be used to prepare the posterior aspect of the femoral condyle as well as the distal aspect of the femoral condyle, increased congruency, high contact area and decreased surface stresses are achieved in the implanted knee, sufficient bone is retained to support future surgical intervention including future total knee replacement, the unicompartmental knee replacement procedures may be performed using an extramedullary technique and/or an intramedullary technique for proper alignment and positioning, the tibial stylus is anatomically contoured to the femoral condyle for enhanced use in a minimal incision procedure, the tibial cutting guide is anatomically contoured to the tibia for enhanced use in a minimal incision procedure, variable accurate tibial resection depths are possible, enhanced fixation is achieved for the tibial component in an onlay cementitious fixation, and the instruments and methods of the present invention can be used in medial compartment knee replacement as well as lateral compartment knee replacement procedures.

These and other objects, advantages and benefits are realized with the present invention as generally characterized in a method of establishing the depth for a proximal tibial resection in a minimally invasive unicompartmental knee replacement procedure. The method includes the steps of accessing a knee through a minimal incision, mounting a tibial cutting guide anteriorly along the tibia of the knee for movement along the long axis of the tibia, and mounting a stylus arm on the tibial cutting guide such that a resection slot of the tibial cutting guide is located a predetermined depth below the stylus arm. The stylus arm is positioned upon the tibial plateau such that the resection slot is located the predetermined depth below the tibial plateau. The corresponding femoral condyle is accommodated in an anatomic contour of the stylus arm. A cutting member is inserted through the resection slot and into the tibia to effect a planar surface along the tibial plateau at the predetermined depth, and the cutting member is withdrawn from the resection slot upon formation of the planar surface. The tibial cutting guide may be mounted along the tibia to position the resection slot perpendicular to the long axis of the tibia or at a downward posterior angle relative to a plane perpendicular to the long axis of the tibia.

The present invention is also generally characterized in a method of surgically preparing a femoral condyle to receive a prosthetic femoral component in a minimally invasive unicompartmental knee replacement procedure. The method involves accessing a knee through a minimal incision, positioning a femoral resurfacing guide on a femoral condyle of the knee to externally delineate an area of the femoral condyle with a rail member of the resurfacing guide, and removing anatomical tissue from the externally delineated area by moving a tissue removing instrument along the externally delineated area within the confines of the rail member. The externally delineated area may be located along a distal aspect of the femoral condyle, and the method may include forming a planar resected surface along a posterior of the femoral condyle via a cutting member inserted through a resection block attached to the femur. The externally delineated area may be accessed by introducing the tissue removing instrument through a window of a slide movably carried by the rail member, with the slide being moved during tissue removal in response to movement of the tissue removing instrument along the delineated area. The method may involve use of an alignment module and/or linking instrument to confirm proper alignment and positioning of the femoral instrumentation.

The present invention is further generally characterized in a method of minimally invasive unicompartmental knee replacement comprising the steps of accessing a knee through a minimal incision, forming a planar surface along a tibial plateau of the knee, forming a planar posterior surface along a posterior aspect of the corresponding femoral condyle, and resurfacing a distal aspect of the femoral condyle to form a resurfaced area including a curved portion having an anterior-posterior curvature extending from the planar posterior surface and a planar portion extending from the curved portion. The resurfaced area may be formed with a plurality of tangent radii in a sagittal plane that match a fixation surface of a prosthetic femoral component. The resurfaced area may have an angular sweep in the coronal plane and may thusly extend from the planar posterior surface at an angle in the medial-lateral direction to match the geometry of a prosthetic femoral component. The planar surface may be formed along the tibial plateau to extend posteriorly at a downward slope or angle or at a zero, neutral or no slope or angle relative to a plane perpendicular to the long axis of the tibia. The method further includes implanting a prosthetic tibial component on the planar surface formed along the tibial plateau and implanting a prosthetic femoral component on the prepared femoral surface formed by the planar posterior surface and the resurfaced area.

The present invention is additionally generally characterized in a method of preparing a femur to receive fixation structure of a prosthetic femoral component in a minimally invasive unicompartmental knee replacement procedure. The method involves accessing a prepared femoral condyle through a minimal incision and using a trial femoral component to establish the location for a peg hole and slot to be formed in the femur to respectively receive a femoral fixation peg and a femoral fixation fin comprising the fixation structure of the prosthetic femoral component. The trial femoral component is fixated on the prepared femoral condyle, and the peg hole for the femoral fixation peg is formed by inserting a cutting member through a bore hole of the trial femoral component at a location corresponding to the location for the femoral fixation peg. The cutting member is advanced through the bore hole and into the femur to form a peg hole in the femur for receiving the femoral fixation peg. Formation of the slot for the femoral fixation fin involves inserting a fin element of a femoral fin punch through a slot in the trial femoral component at a location corresponding to the location for the femoral fixation fin, with a peg element of the femoral fin punch disposed in the bore hole. The femoral fin punch is advanced to advance the peg element through the bore hole and into the peg hole and to advance the fin element through the slot and into the femur to form a slot in the femur for receiving the femoral fixation fin.

Another characterization of the present invention is in a method of preparing a tibia to receive fixation structure of a prosthetic tibial component in a minimally invasive unicompartmental knee replacement procedure. The method involves accessing a prepared tibial plateau through a minimal incision and attaching a trial tibial component on the prepared tibial plateau to establish the location for anterior and posterior peg holes to respectively receive anterior and posterior tibial fixation pegs comprising the fixation structure of the prosthetic tibial component. With the trial tibial component fixated on the prepared tibial plateau at the correct location, a guide is positioned on the trial tibial component with a sleeve of the guide aligned with and extending anteriorly at an angle to a posterior bore hole of the trial tibial component at a location corresponding to the location of the posterior tibial fixation peg. A cutting member is inserted through the sleeve and the posterior bore hole into the tibia to form a posterior peg hole in the tibia for receiving the posterior tibial fixation peg. The cutting member is inserted through an anterior bore hole of the trial tibial component at a location corresponding to the location of the anterior tibial fixation peg to form an anterior peg hole in the tibia for receiving the anterior tibial fixation peg. The cutting member has a stop for engaging the sleeve to limit penetration of the cutting member into the tibia to a predetermined depth. The cutting member has a depth stop, and the cutting member is advanced through the anterior bore hole to the depth stop to ensure the proper depth of penetration.

The present invention is also generally characterized in a method of implanting a prosthetic femoral component on a prepared femoral condyle in minimally invasive unicompartmental knee replacement. The method comprises the steps of accessing a prepared femoral condyle through a minimal incision, applying cementitious material to a fixation surface of a prosthetic femoral component in which the fixation surface includes a border surrounding a cavity, aligning a femoral fixation peg and a femoral fixation fin of the prosthetic femoral component with a peg hole and slot, respectively, prepared in the femoral condyle, and inserting the femoral fixation peg and fin in the peg hole and slot, respectively, to place the border on the prepared femoral condyle. A planar rearward section of the border is placed on a planar resected surface prepared along a posterior aspect of the femoral condyle. A curved intermediate section of the border is placed on a curved portion of a resurfaced area prepared along a distal aspect of the femoral condyle extending anteriorly from the planar resected surface. A planar forward section of the border is placed on a planar portion of the resurfaced area extending anteriorly from the curved portion. The prosthetic femoral component is secured on the prepared femoral condyle via the cementitious material.

An additional characterization of the present invention is in a method of implanting a prosthetic tibial component on a prepared tibial plateau in a minimally invasive unicompartmental knee replacement procedure. The method involves accessing a prepared tibial plateau through a minimal incision, applying cementitious material to a fixation surface of a prosthetic tibial component, aligning anterior and posterior tibial fixation pegs protruding from the fixation surface with anterior and posterior peg holes, respectively, prepared in the tibia, inserting the anterior and posterior tibial fixation pegs in the anterior and posterior peg holes, respectively, and supporting a continuously planar rim of the fixation surface upon a planar surface prepared along the tibial plateau. The cementitious material is confined to a cavity of the fixation surface via a dovetail wall surrounding the cavity as pressure is applied to the prosthetic tibial component, and the prosthetic tibial component is secured in place on the prepared surface via the cementitious material.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 1 is a front view of a tibial cutting guide or crosshead for use in the methods of the present invention.

FIG. 2 is a top view of the tibial crosshead.

FIG. 3 is a side view of the tibial crosshead.

FIG. 4 is a sectional view of the tibial crosshead taken along line A—A of FIG. 1.

FIG. 5 is a rear view of the tibial crosshead.

FIG. 6 is a side view of a tibial stylus for use with the tibial crosshead of the present invention.

FIG. 7 is a top view of the tibial stylus.

FIG. 11B is a top view of a modified handle for use with the trial femoral component.

FIG. 11C is a side view of the modified handle of FIG. 11B.

FIG. 11D is a longitudinal sectional view of the modified handle of FIG. 11B.

FIG. 16 is a front view of the posterior resection block.

FIG. 17 is a top view of the posterior resection block.

FIG. 18 is a side view of the posterior resection block.

FIG. 19 is a rear view of the posterior resection block.

FIG. 40 is a broken perspective view further depicting the femoral alignment module assembled to the posterior resection block.

FIG. 41 is a broken perspective view showing the valgus rod placed in the femoral intramedullary canal.

FIG. 42 is a broken perspective view illustrating the linking instrument assembled with the femoral resurfacing guide/posterior resection block assembly to form a construct coupled with the valgus rod.

DESCRIPTION OF THE PREFERRED EMBODIMENTS

Figure 9:
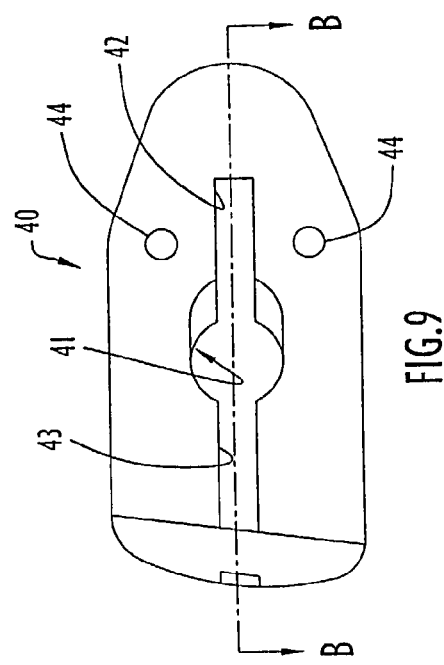
FIG. 9 is a top view of the trial femoral component.

The instruments and methods of the present invention relate to implantation of knee joint prostheses and, in particular, to minimally invasive unicompartmental implantation of knee joint prostheses, especially the knee joint prostheses disclosed in the concurrently filed non-provisional patent applications entitled Knee Joint Prostheses, Prosthetic Femoral Components and Prosthetic Tibial Components, the entire disclosures of which were previously incorporated herein by reference. Accordingly, the knee joint prostheses and the prosthetic femoral and tibial components discussed herein include the knee joint prostheses and the prosthetic femoral and tibial components disclosed in the aforementioned patent applications. It should be appreciated, however, that the instruments and methods of the present invention may be used or adapted for use with other knee joint prostheses and may be performed using open surgical techniques. Although the instruments and methods of the present invention are illustratively described below for medial compartment knee joint replacement of a left or right knee, it should be appreciated that the instruments and methods of the present invention may be used or adapted for use in lateral compartment knee joint replacement of a left or right knee.

As used herein, "medial compartment" of a knee refers to the femoral condyle and corresponding tibial plateau of the knee located closer to the median plane of the patient's body, i.e. the plane that divides the body in half lengthwise, and "lateral compartment" of a knee refers to the femoral condyle and corresponding tibial plateau of the knee located further from the median plane. The term "medial" refers to a side or direction toward the median plane, the term "lateral" refers to a side or direction away from the median plane, the term "anterior" refers to a side or direction toward the front of the knee, the term "posterior" refers to a side or direction toward the back of the knee, the term "distal" refers to a downward side or direction, and the term "proximal" refers to an upward side or direction.

A tibial crosshead or cutting guide 10 for use in the methods of the present invention is illustrated in FIGS. 1–5. The tibial crosshead 10 is shown as a "left" tibial crosshead for use in implantation of a knee joint prosthesis on the left knee of a patient, and a "right" tibial crosshead in accordance with the present invention for use on a right knee is a mirror image of the "left" tibial crosshead 10. The tibial crosshead 10 has an anterior portion 11 of greater height than a posterior portion 12 thereof, the posterior portion 12 forming a curving wing 13 defined by a curved side wall 14 of the posterior portion, a curved posterior wall 15 of the posterior portion and a transition wall 16 of the posterior portion joining the side wall 14 to the posterior wall 15. As shown in FIG. 2, the side wall 14 has a radius of curvature R1, and the posterior wall 15 has a radius of curvature R2. The anterior portion 11 has an inner side wall 17 and a parallel outer side wall 18 spaced outwardly from inner side wall 17 to define a generally C-shaped outer arm extending from the anterior portion. A channel 19 extends through the anterior portion 11 from top to bottom and is defined by the C-shaped outer arm and by an opposing, C-shaped inner arm formed by a curved internal surface 20 of the anterior portion. The channel 19 has a configuration in cross-section to receive a shaft of a tibial alignment guide as explained further below. An anterior opening along a planar anterior wall 21 of the anterior portion 11 extends from top to bottom between the opposing C-shaped arms and provides an entrance to channel 19. The channel 19 has a central longitudinal axis that is angled posteriorly from top to bottom relative to a medial-lateral plane perpendicular to a planar resection slot 24 of the tibial crosshead, so as to provide a posteriorly sloped resection through the resection slot 24 of the crosshead when the tibial crosshead is assembled to the tibial alignment guide as explained further below. A plurality of fixation holes 22 extend entirely through the anterior portion 11 from the planar anterior wall 21 to a planar posterior wall 23 of the anterior portion. The lowermost fixation hole 22', as shown in FIG. 4, has an opening on the anterior wall 21 with a center disposed in a plane P1 parallel to a plane P2 containing inner side wall 17. The fixation hole 22' has a central longitudinal axis disposed in a plane P3 forming an angle A1 with plane P1. The slot 24 extends entirely through the tibial crosshead from anterior to posterior, and has a uniform or constant height or depth between upper and lower planar internal surfaces of the tibial crosshead. The slot 24 may be limited or bounded by a slot end 25 in side wall 14 adjacent transition wall 16, by a slot end 26 in anterior wall 21 adjacent the C-shaped inner arm, and by slot ends 27 in posterior wall 15. It should be appreciated that the slot end 25 and/or the slot end 27 can be eliminated in that the slot 24 may extend to and open on the side of the crosshead as shown by dotted lines in FIGS. 1 and 5. A through hole 28 is formed in the tibial crosshead perpendicular to the planar top wall thereof for attachment of a tibial stylus as explained below. The hole can be provided at one or more suitable predetermined locations as shown by dotted lines in FIG. 2, and more than one hole 28 can be provided in the tibial crosshead. The posterior wall 15 conforms to the anatomic configuration of the anterior tibia when the cutting guide 10 is positioned adjacent thereto as explained below.

An illustrative but not limiting tibial crosshead has an overall length between planes P4 and P5 and an overall width between planes P6 and P7. Plane P2 bisects the channel 19. The planar resection slot has a height or depth between the upper and lower internal surfaces. The fixation hole 22' has an opening on posterior wall 23 with a center located above a planar bottom surface of the anterior portion 11. Three pairs of fixation holes have openings on the posterior wall 23 with centers located below the planar top surface of the tibial crosshead. The angle of channel 19 may be five degrees to provide a five degree posteriorly sloped tibial resection relative to a plane perpendicular to the long axis of the tibia, may be seven degrees to provide a seven degree posteriorly sloped tibial resection or may be any other suitable angle to provide a tibial resection of appropriate angle or slope. In addition, the tibial crosshead can be designed to provide a tibial resection of neutral, zero or no slope or angle, i.e. within the plane perpendicular to the long axis of the tibia, in which case the central longitudinal axis of channel 19 is not angled from the vertical and is perpendicular to the resection slot 24. Different crossheads having different angles or no angles may be provided.

A tibial stylus 30 for use with the tibial cutting guide or crosshead 10 is shown in FIGS. 6 and 7. The tibial stylus 30 has first and second curved stylus arms 31 and 32 extending downwardly from opposing ends of a flat connecting plate 33. An elongate, longitudinal slot 34 with radiused ends is formed in connecting plate 33, and a cylindrical stylus base 35 extends through the slot 34 in a direction perpendicular to plate 33. The slot 34 has a length and a width, with the slot 34 being centered between the side edges of connecting plate 33. The stylus base 35 may be selectively movable longitudinally within slot 34 and held in place via a cap 36 which may be threaded and/or spring biased to the base 35. A cylindrical stem 37 protrudes downwardly from base 35 in axial alignment therewith and mounts a detent 38, which is illustrated as but not limited to a protruding, spring biased detent ball. Stylus arms 31 and 32 have respective ends 39 with lower surfaces, respectively, disposed in planes P8 and P9, respectively. A lower edge of stylus base 35 is contained in a plane P10 parallel to planes P8 and P9. Plane P10 is disposed below planes P8 and P9, and is disposed a greater distance below plane P9 than plane P8. Upper surfaces of stylus arms 31 and 32 have radii of curvatures R3 and R4, respectively, and the lower surfaces of the stylus arms 31 and 32 have radii of curvatures R5 and R6, respectively. The connecting plate 33 is of uniform or constant width between opposing, straight side edges thereof, and the stylus arms 31 and 32 taper in width from the connecting plate to their ends 39, respectively. In the tibial stylus 30, the connecting plate has a thickness and the thickness of the stylus arms tapers from the connecting plate to the ends 39. In use, the stem 37 of the tibial stylus is inserted in the appropriate through hole 28 of the tibial crosshead, with the detent 38 deflecting inwardly to permit such insertion. Upon the detent clearing the upper internal surface of the tibial crosshead, the detent is spring biased to its protruding position to releasably connect the tibial stylus to the crosshead with the lower edge of the stylus base 35 upon the planar top surface of the crosshead.

The tibial stylus 30 is illustrated as a compound tibial stylus capable of establishing a tibial resection through the resection slot of the crosshead at two different depths, i.e. a first depth below the level where the corresponding stylus arm 31 rests on the proximal tibia or a second depth below the level where the corresponding stylus arm 32 rests on the proximal tibia. In one illustrative but not limiting embodiment, for example, stylus arm 31 may be a 4 mm stylus arm for establishing a tibial resection depth 4 mm below the level where the stylus arm 31 rests on the proximal tibia, and the stylus arm 32 may be a 2 mm or a 6 mm stylus arm for establishing a tibial resection depth 2 mm or 6 mm below the level where the stylus arm 32 rests on the proximal tibia. In another illustrative but not limiting embodiment, the stylus arm 31 may be a 6 mm stylus arm to establish a 6 mm tibial resection depth below the level where the stylus arm 31 rests on the proximal tibia, and the stylus arm 32 may be an 8 mm stylus arm to establish an 8 mm tibial resection depth below the level where the stylus arm 32 rests on the proximal tibia. It should be appreciated, therefore, that the stylus arms can be designed to establish tibial resections of any desired depths. The curvatures of the stylus arms correspond to, conform to, match or follow the anatomic geometry of the femoral condyle such that the stylus arms closely accommodate or cradle the distal surface of the femoral condyle when the stylus arms are positioned on the corresponding tibial plateau as explained further below. The design of the stylus enhances ease of use in minimally invasive unicompartmental procedures.

Figure 10:
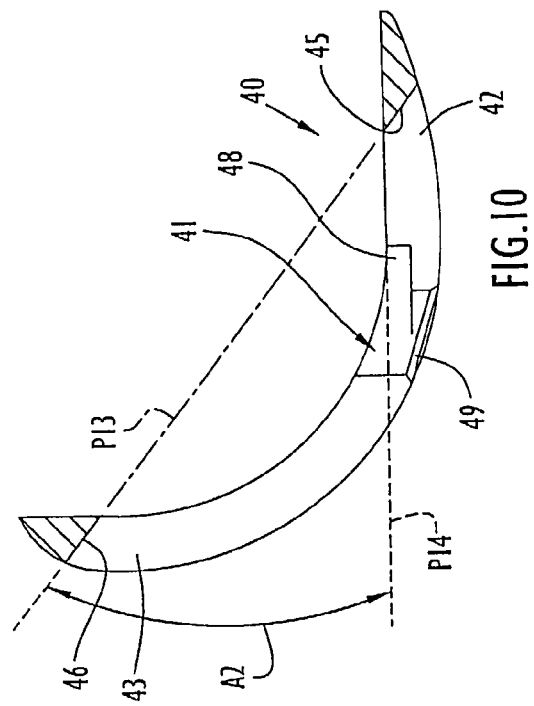
FIG. 10 is a sectional view of the trial femoral component taken along line B—B of FIG. 9.
Figure 8:
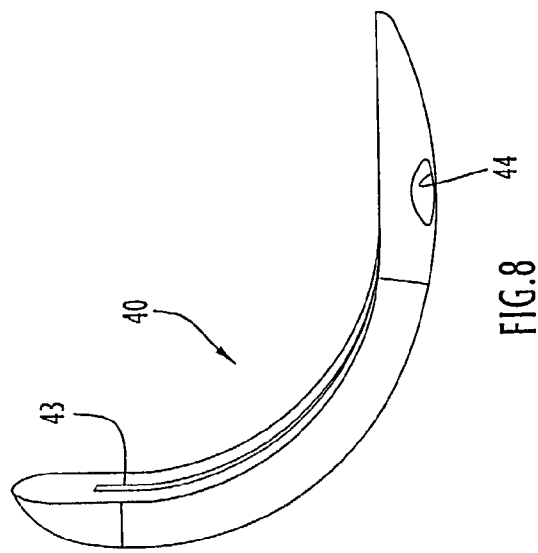
FIG. 8 is a side view of a trial femoral component for use in the methods of the present invention.

FIGS. 8–10 illustrate a trial femoral component 40 used to properly size and locate the actual or prosthetic femoral component of the knee joint prosthesis. Trial femoral component 40 is illustrated as a "left" trial femoral component corresponding to the "left" femoral component disclosed in the aforementioned patent application incorporated herein by reference for implantation on the "left" knee of a patient, and a "right" trial femoral component corresponding to a femoral component designed to be implanted on the right knee of a patient is a mirror image of the "left" trial femoral component 40. Trial femoral component 40 is similar to the actual femoral component disclosed in the applications incorporated herein by reference and thusly has a femoral trial fixation surface corresponding to the femoral fixation surface of the prosthetic femoral component. Accordingly, the femoral trial fixation surface includes a planar rearward section, a curved intermediate section and a planar forward section corresponding to the rearward, intermediate and forward sections of the femoral fixation surface of the prosthetic femoral component. The trial femoral component 40 does not have a femoral fixation peg or fin but has a stepped bore hole 41 corresponding to the femoral fixation peg of the actual femoral component and has a slot comprising anterior and posterior slot segments 42 and 43, respectively, extending from bore hole 41 in correspondence with the anterior and posterior femoral fixation fin segments, respectively, of the actual femoral component. Also, the trial femoral component 40 has stepped, anterior bore holes 44 on opposite sides of anterior slot segment 42 to receive fixation pins or other fixation elements for temporarily fixating the trial femoral component to the femur. The counterbored or stepped holes which receive the fixation pins ensure that the heads of the fixation pins are recessed from the outer surface of the trial femoral component corresponding to the femoral articular surface of the actual femoral component. As shown in FIG. 10, the anterior slot segment terminates anteriorly at an angled end surface 45 that is angled downwardly and anteriorly from the inner surface of the trial femoral component. The posterior slot segment 43 terminates posteriorly at an angled end surface 46 angled upwardly and posteriorly from the inner surface of the trial femoral component. The end surfaces 45 and 46 are in a plane P13 disposed at angle A2 with a plane P14 containing a planar anterior section of the inner surface of the trial femoral component.

The trial femoral component 40 may be made available in various sizes corresponding to the sizes of the femoral component disclosed in the application incorporated herein by reference. In an illustrative but not limiting embodiment, angle A2 is 38 degrees. As shown in FIG. 10, the stepped bore 41 has an inner bore section 48 opening on the inner surface of the trial femoral component and an outer bore section 49 opening on the outer surface of the trial femoral component. In an illustrative but not limiting embodiment, the inner bore section 48 has an oblong configuration in cross-section, and the outer bore section 49 has a circular configuration in cross-section flaring to an opening along the outer surface of the trial femoral component.

Figure 11A:
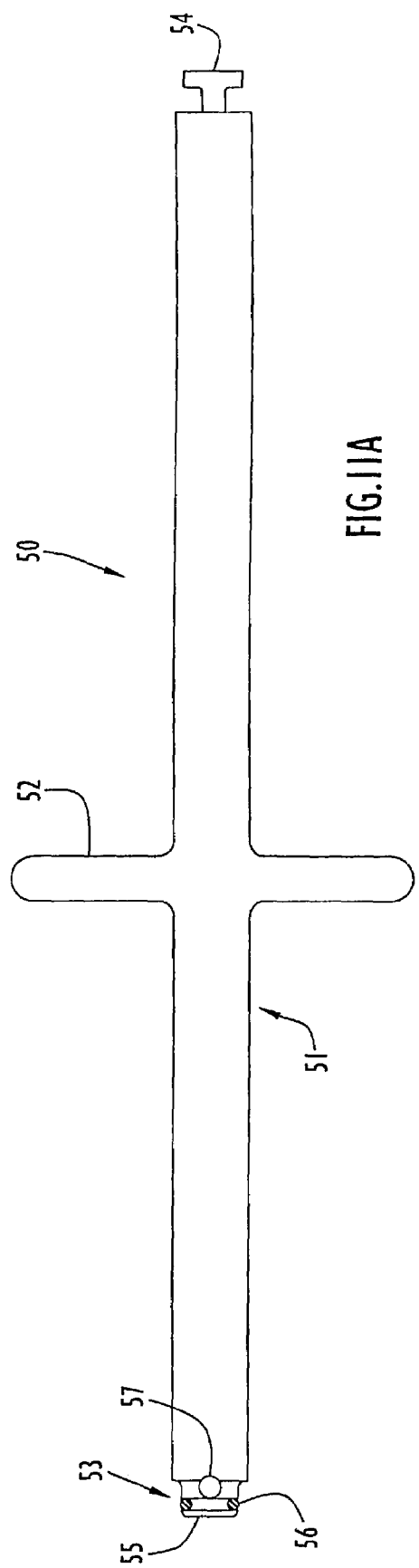
FIG. 11A is a top view of a handle for use with the trial femoral component of the present invention.

A selectively attachable handle 50 for use with the trial femoral component is shown in FIG. 11A and includes an elongate body 51 with a cross-piece 52 forming a T-formation to facilitate grasping. A forward end 53 of the body 51 defines a trial femoral component holder and a proximal end 54 thereof defines a trial femoral component extractor. The forward end 53 forms a lip member 55 having an annular groove receiving an O-ring 56, shown in cross-section. The forward end 53 is adapted to releasably engage with the stepped bore hole 41 of the trial femoral component 40. A cross pin 57 in the forward end 53 protrudes diametrically and prevents rotation of the trial femoral component on the handle by engaging in the anterior and posterior slot segments 42 and 43 of the trial femoral component.

A modified and preferred selectively attachable handle for use with the trial femoral component is illustrated at 50' in FIGS. 11B, 11C and 11D. The handle 50' includes elongate body 51' comprising outer body member 51a' and inner body member 51b' slidably disposed in the outer body member. The outer body member 51a' has a cross-piece 52' forming a T-formation to facilitate grasping and operation. A forward end 53' of the inner body member 51b' forms a releasable holder for the trial femoral component. A bias member biases the outer body member 51a' to an extended position shown in FIGS. 11B, 11C and 11D, while allowing the outer body member 51a' to be moved to a retracted or withdrawn position when a proximal end 54' of the inner body member is moved closer to the cross-piece 52' via manual compressive or squeezing operation of the proximal end 54' and cross-piece 52'. Also, the bias member automatically returns the outer body member 51a' to the extended position when the compressive or squeezing force is removed. A slot in the inner body member 51b' permits relative sliding movement of the outer and inner body members between the extended and retracted positions. The bias member is shown as a coil spring disposed around the inner body member 51b' and confined within the outer body member 51a' between an internal shoulder on the outer body member 51a' and an external shoulder on the inner body member 51b'. However, the bias member may comprise other types of springs or other biasing devices including one or more components. In the extended position, a wedge element 58' carried by and movable with the outer body member 51a' alongside the inner body member 51b' is extended forwardly and, in the retracted position, the wedge element 58' is retracted so that forward end 53' is extended forwardly from or beyond the wedge element 58'. Accordingly, when the cross-piece 52' and proximal end 54' are squeezed, the outer body member 51a' is moved to the retracted position with the forward end 53' disposed forwardly of the wedge element 58' to permit the forward end 53' to be inserted in the bore hole 41 of the trial femoral component. When the squeezing force on cross-piece 52' and proximal end 54' is removed, the outer body member 51a' is returned to the extended position, causing wedge element 58' to be moved into the bore hole 41 alongside the forward end 53' and thereby secure the trial femoral component to the forward end 53' with a wedging action or force. When the handle 50' is thereafter squeezed to move the outer body member 51a' to the retracted position, the wedge element 58' is withdrawn from the bore hole, allowing the forward end 53' to be withdrawn or removed from the bore hole 41 to effect detachment of the handle from the trial femoral component.

Figure 12:
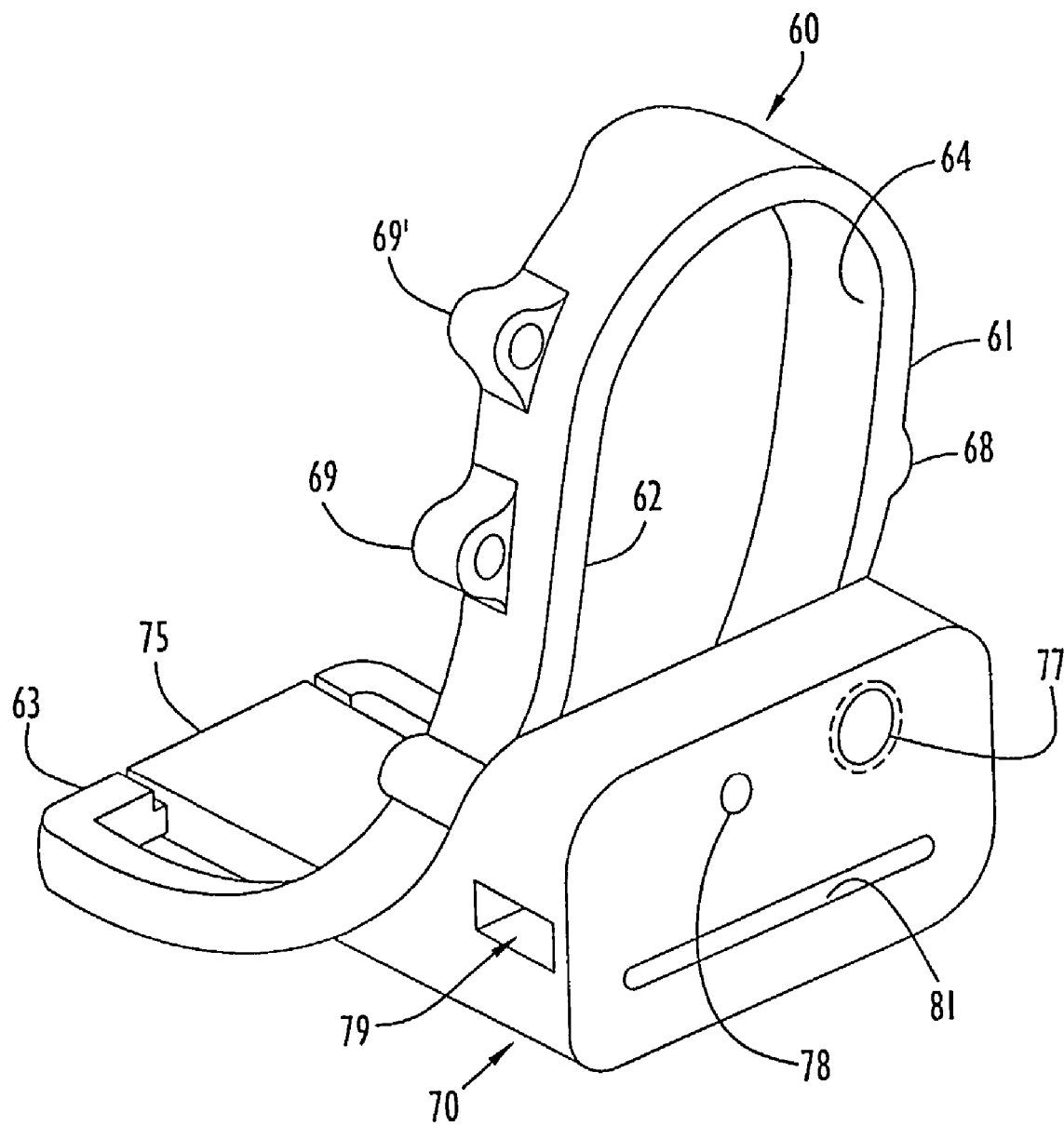
FIG. 12 is a perspective view of a femoral resurfacing guide/posterior resection block assembly for use in the methods of the present invention.
Figure 15:
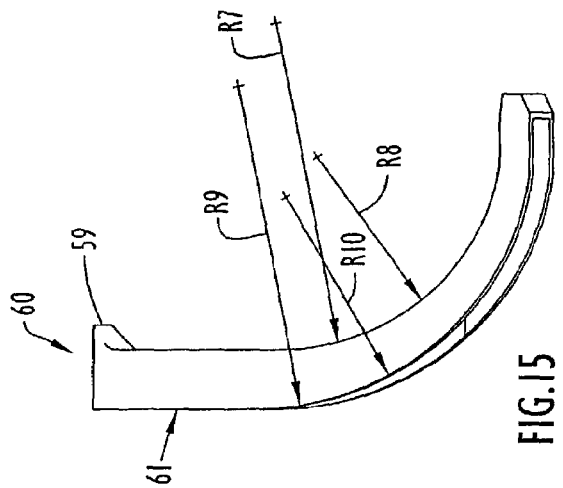
FIG. 15 is a side view of the femoral resurfacing guide.
Figure 14:
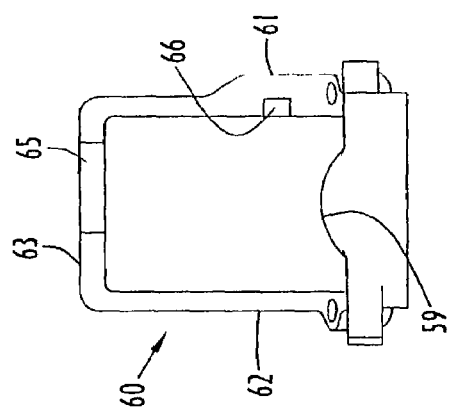
FIG. 14 is a top view of the femoral resurfacing guide.
Figure 13:
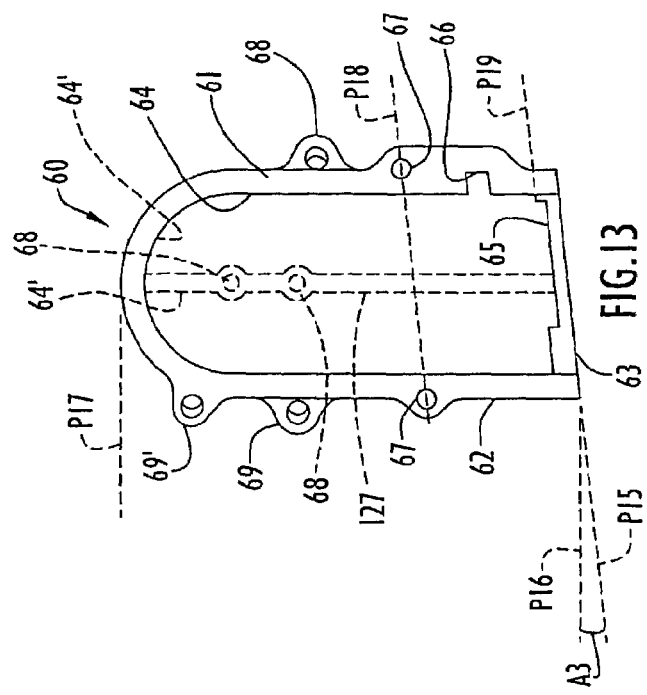
FIG. 13 is a front view of the femoral resurfacing guide.
Figure 21:
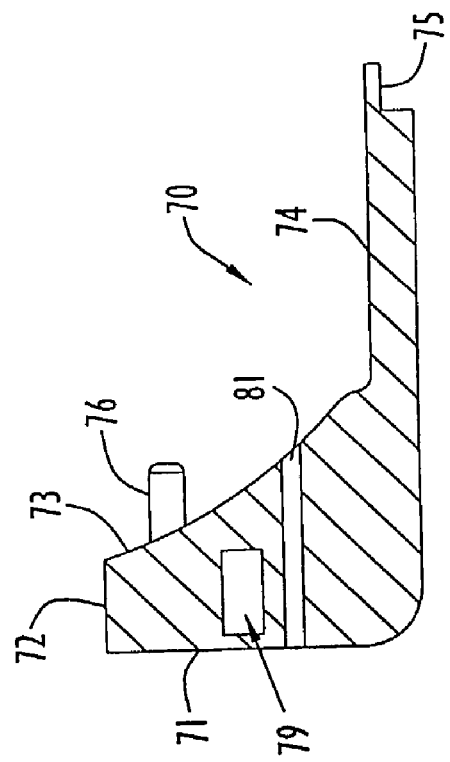
FIG. 21 is a sectional view of the posterior resection block taken along line D—D of FIG. 17.

FIG. 12 illustrates a femoral resurfacing guide/posterior resection block assembly including a femoral resurfacing guide 60 and a posterior resection block 70. The femoral resurfacing guide 60 is illustrated in FIGS. 12–15 and includes a generally U-shaped rail member having parallel legs 61 and 62, which curve in the posterior direction to posterior ends connected by a transverse connecting pad 63, which may be formed integrally, unitarily with the legs. The rail member has an inside surface 64 defining a track for a femoral resurfacing instrument as described below, the inside surface or track 64 externally delineating an area of the femoral condyle to be resurfaced. As best shown in FIG. 13, the connecting pad 63 is angled downwardly from leg 61 to leg 62, and its lower surface is in a plane P15 that forms an angle A3 with a horizontal plane P16. The angle A3 corresponds to the angular sweep of the actual femoral component disclosed in the application previously incorporated herein by reference. Of course, for femoral components not having an angular sweep, the connecting pad may be oriented in the horizontal plane between legs 61 and 62. The plane P16 is parallel to a plane P17 containing a top of the rail member which forms an arcuate, posteriorly protruding stylus or tab 59 for a purpose to be described below. The top surface of the connecting pad 63 has a recessed surface 65, and a notch 66 is formed along the inside surface of leg 61. The legs 61 and 62 have through holes 67, respectively, extending therethrough from the front surface to the back surface of the rail member, and the centers of the through holes are in a plane P18 parallel to plane P15. An eyelet 68 is disposed on leg 61, and eyelets and 69' are disposed on leg 62. The legs 61 and 62 have posterior radii of curvatures R7 and R8 and anterior radii of curvatures R9 and R10 as shown in FIG. 15.

The femoral resurfacing guide 60 is designed for use with a "left" femoral component as disclosed in the application incorporated herein by reference and is thusly a "left" femoral resurfacing guide. It should be appreciated, however, that a "right" femoral resurfacing guide may be provided as a mirror image of the "left" femoral resurfacing guide for use with a "right" femoral component. Also, the femoral resurfacing guide is made available in sizes corresponding to the sizes of the actual femoral components. For example, the illustrated femoral resurfacing guide 60 may be a Size 2 femoral resurfacing guide corresponding to a Size 2 femoral component of the aforementioned patent application. The inside surface or track of the femoral resurfacing guide 60 follows a configuration corresponding to the anterior-posterior and outer medial-lateral geometry of the actual femoral component and, depending on the actual femoral component, the track of the femoral resurfacing guide may or may not have an angular sweep.

An illustrative but not limiting femoral resurfacing guide has an overall height between planes P16 and P17. The medial-lateral width of the track corresponds to the perpendicular distance between the inside surface of leg 61 and the inside surface of leg 62. The hole for eyelet 68 has a center located in a plane parallel to plane P17. The hole for eyelet 69 has a center located in a plane parallel to plane P17. The center of the hole for eyelet 69' is located in a plane disposed at an angle to a sagittal plane bisecting the femoral resurfacing guide 60 vertically. The actual dimensions of the femoral resurfacing guide will depend on the particular size of the femoral resurfacing guide.

Figure 20:
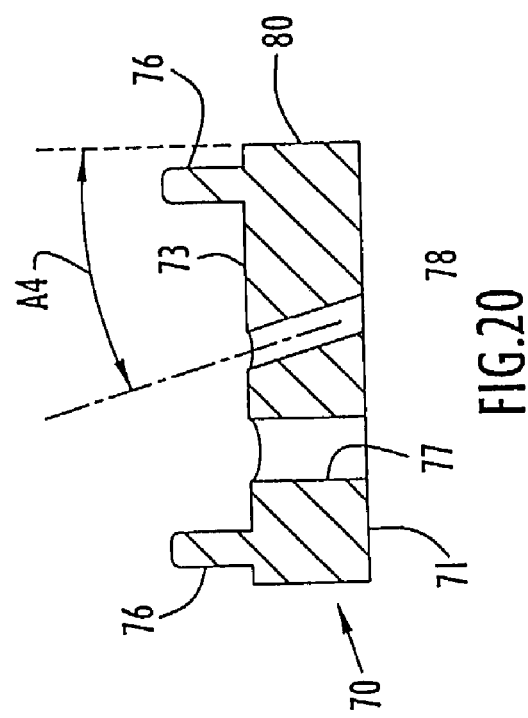
FIG. 20 is a sectional view of a housing of the posterior resection block taken along line C—C of FIG. 19.

The posterior resection block 70, as shown in FIGS. 12 and 16–21, includes a housing having an anterior or forward portion and a base plate extending posteriorly or rearwardly from the anterior portion. The anterior portion for resection block 70 has a front surface 71, a top surface 72 and a back surface 73 curving downwardly from top surface 72 to the elongate, rearwardly extending base plate 74 terminating at a cantilevered planar tongue 75. The base plate 74 defines a bottom surface or wall of the housing as shown in FIGS. 16, 18 and 19. A pair of attachment posts 76 extend rearwardly from back surface 73 and are adapted to be received in the through holes 67 of the femoral resurfacing guide with the tongue 75 resting on the recessed surface 65 of the femoral resurfacing guide as shown in FIG. 12. The posterior resection block is thusly connectible with the femoral resurfacing guide 60 such that the resulting femoral resurfacing guide/ posterior resection block assembly may be handled essentially as a one-piece unit or construct for ease of use and simplification of procedural steps. The femoral resurfacing guide/posterior resection block assembly may be provided with or without structure for mechanically locking the posterior resection block to the femoral resurfacing guide. A threaded hole 77 and a fixation hole 78 open on the front surface 71 and extend rearwardly through the anterior portion of the housing to open on back surface 73. The attachment posts 76 and the holes 77 and 78 are aligned with one another in the medial-lateral direction as best shown in FIG. 19. A channel 79 extends through the housing in the medial-lateral direction and opens on opposing side walls of the housing. The channel 79 has a central longitudinal axis transverse or perpendicular to a central longitudinal axis of the housing. The channel 79 is rectangular in cross-section with its cross-sectional length oriented perpendicular to front surface 71, which is planar, and its cross-sectional width oriented parallel to front surface 71. As shown in FIG. 20, threaded hole 77 extends perpendicular to front surface 71 and parallel to attachment posts 76, but could extend at any suitable angle to the front surface. Fixation hole 78 extends from the front surface 71 at an angle toward threaded hole 77. A central longitudinal axis of fixation hole 78 is disposed at angle A4 with a side wall 80 of the housing. A resection slot 81 extends through the housing from front to rear, the slot having a front slot opening on front surface 71 and a back slot opening on back surface 73, which is planar and parallel to front surface 71. The slot 81 is planar with a uniform height in the vertical direction between parallel upper and lower internal surfaces of the housing, and the slot 81 is parallel to a bottom surface of base plate 74 and to tongue 75. It should be appreciated that the posterior resection block and the femoral resurfacing guide need not be assembled and used as an essentially one-piece assembly, but can constitute and be used individually as separate and distinct instruments in multiple procedural steps.

The posterior resection block is made available in size ranges, for example, Size 1–2 and Size 3–4, corresponding to the sizes of the prosthetic femoral components of the referenced application. The illustrated posterior resection block 70 may, for example, be a Size 1–2 posterior resection block for use in implantation of a Size 2 femoral component. By way of illustration and not limitation, the posterior resection block 70 has an overall length from front to rear, with the base plate 74 extending rearwardly of the back surface 73; the front surface 71 has an overall medial-lateral width, with the base plate 74 having a width less than the width of the front surface; the posterior resection block 70 has an overall height in the vertical direction, with the base plate 74 having a height or thickness in the vertical direction less than the overall height and the tongue 75 having a thickness less than the thickness of the base plate; the attachment posts 76 terminate rearwardly of front surface 71; the attachment posts 76 have centers spaced from one another, and each attachment post may be spaced the same distance from the sagittal plane defined by line D—D; the centers for the attachment posts 76 are above the planar top surface of the base plate; the resection slot 81 has radiused medial-lateral ends and has a medial-lateral width between the radiused ends; and the slot 81 is centered within the medial-lateral width of the resection block.

Figure 22:
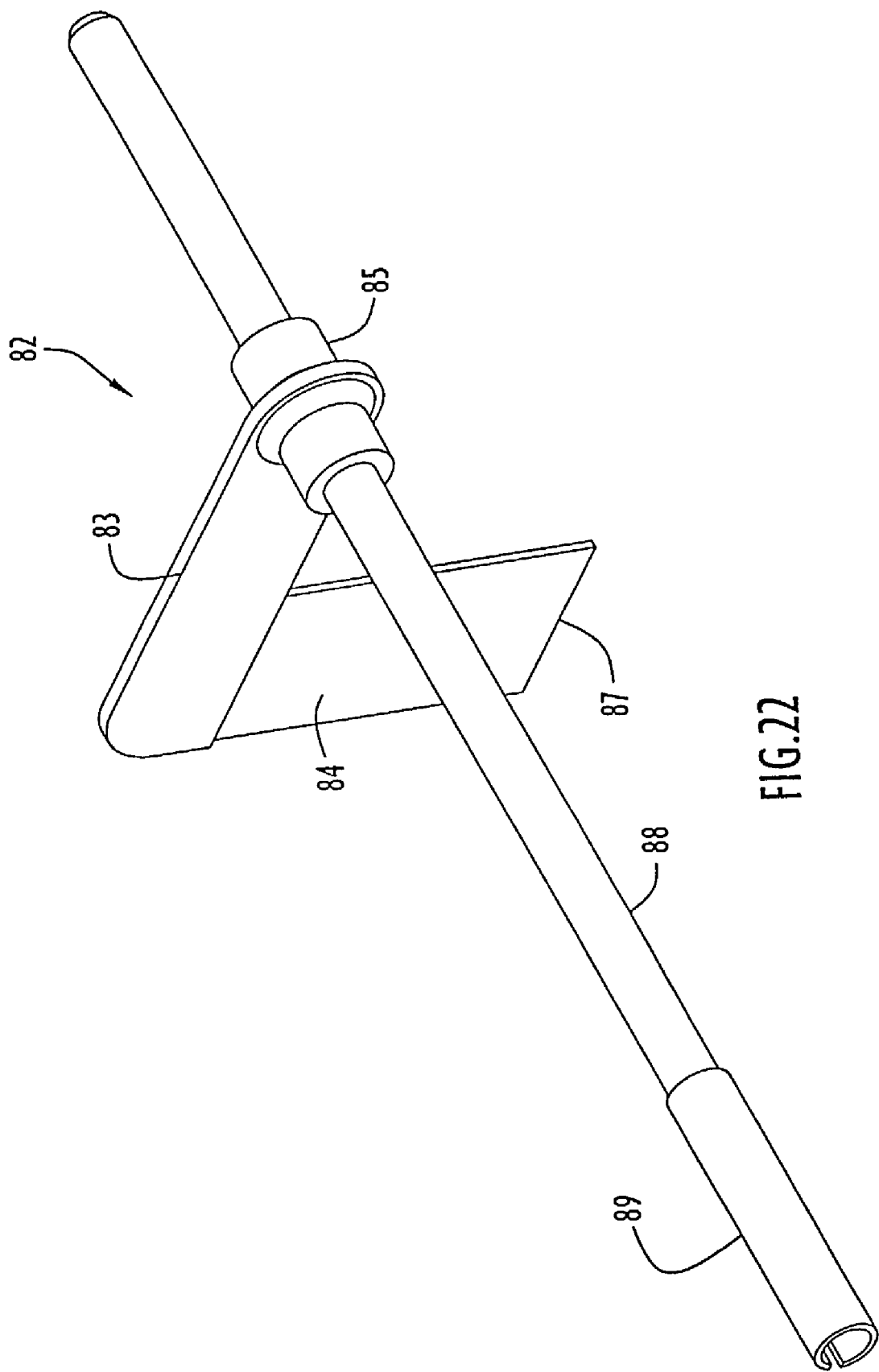
FIG. 22 is a perspective view of a femoral alignment module for use with the posterior resection block and/or tibial crosshead in accordance with the present invention.

A femoral alignment module 82 for use with the tibial cutting guide or crosshead 10 and/or the posterior resection block 70 is illustrated in FIG. 22 and includes an angled tab having a planar leg 83 and a planar foot 84 extending perpendicularly from a first end of leg 83. The same femoral alignment module 82 may be used as either a "left" femoral alignment module on the left knee of a patient, or as a "right" femoral alignment module on the right knee of a patient merely by reversing the orientation of the femoral alignment module 82. A second end of leg 83 carries a cylindrical barrel 85 having a lumen of circular cross-section extending therethrough. The cylindrical barrel protrudes beyond parallel upper and lower surfaces of leg 83, and the lumen is perpendicular to the upper and lower surfaces of leg 83 such that the lumen is perpendicular to the plane of foot 84. The leg 83 has a height or thickness between its parallel upper and lower surfaces. Foot 84 extends posteriorly from the leg 83 to a straight posterior edge 87 and is of uniform medial-lateral width between parallel side edges of foot 84. Foot 84 has a height or thickness between parallel upper and lower surfaces thereof and is dimensioned to be received in the resection slot 24 of the tibial crosshead 10 and/or the resection slot 81 of the posterior resection block 70 with a close fit. The parallel upper and lower surfaces of foot 84 are parallel to the upper and lower surfaces of leg 83, with the foot 84 having a height or thickness slightly less than the height or thickness of leg 83. The first end of leg 83 is joined to the foot 84 by a curved outside corner, and the second end of leg 83 is curved or rounded. An extramedullary check rod 88 is insertable in the lumen of barrel 85 to protrude upwardly and downwardly from the barrel. The check rod 88 may be slidably and rotatably mounted or received in the lumen of the barrel and may be held in a desired position via a friction or interference fit with the barrel. The check rod may be provided with indicia to facilitate proper directional orientation.

Figure 23:
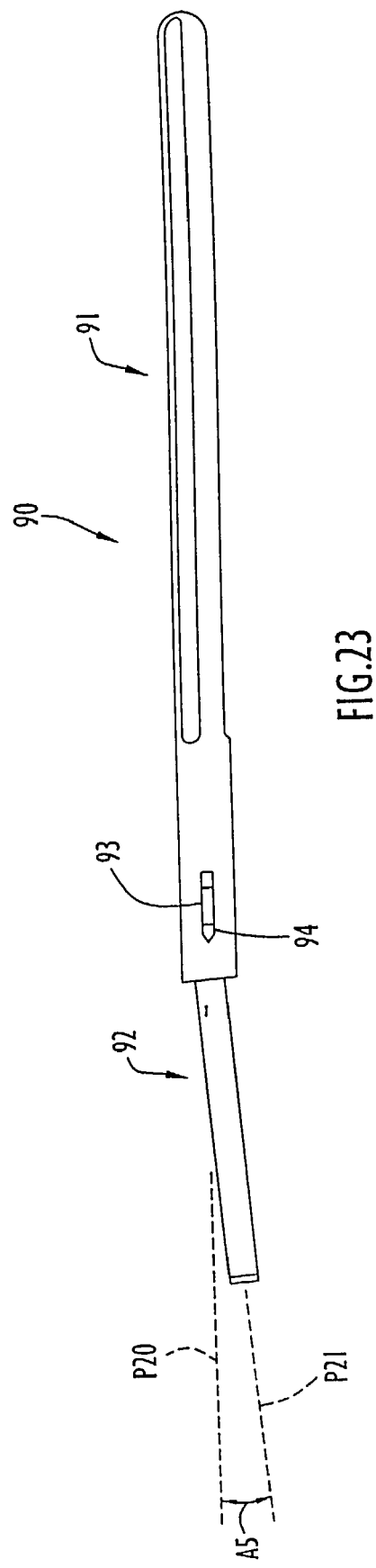
FIG. 23 is a top view of an intramedullary or valgus rod for use in the methods of the present invention.
Figure 25:
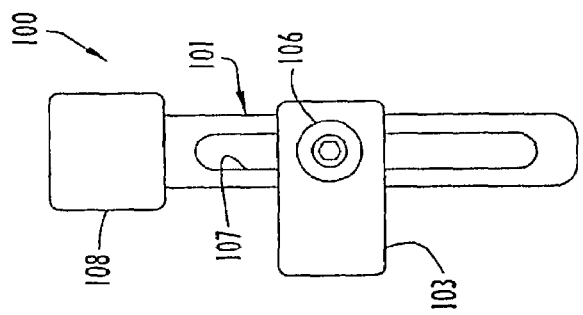
FIG. 25 is a side view of the linking instrument.
Figure 24:
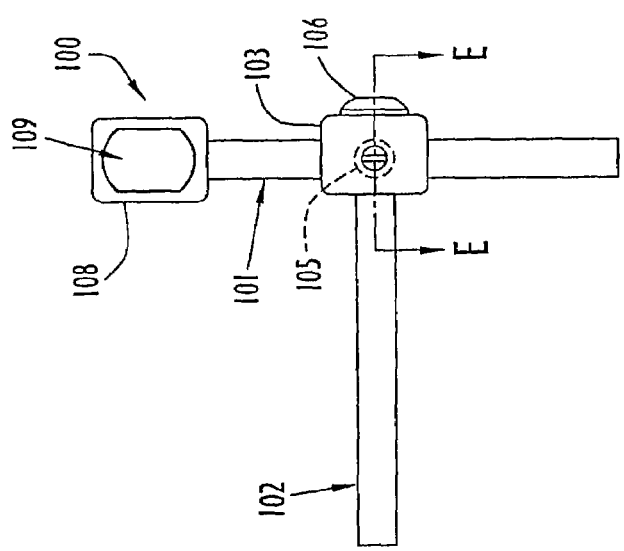
FIG. 24 is a front view of a linking instrument for use with the posterior resection block and valgus rod in the methods of the present invention.

An intramedullary rod or valgus rod 90 for use in the methods of the present invention is illustrated in FIG. 23 and includes a longitudinal bone insertion element 91 and a handle 92 extending from a rearward end of bone insertion element 91 at an angle A5. Bone insertion element 91 has longitudinal flutes in its external surface and has longitudinally extending vanes 93 protruding radially outwardly from its external surface. The flutes allow the rod 90 to be inserted into the femoral intramedullary canal without pressurizing the marrow. Vanes 93, only one of which is visible in FIG. 23, are located at diametric locations on bone insertion element 91 and are thusly spaced about 180 degrees from one another. The vanes 93 prevent rotation of the valgus rod 90 in the intramedullary canal during use thereof and have sharpened, angled edges 94 that point outwardly to facilitate extraction or removal of the valgus rod from the intramedullary canal after use thereof. The hand 92 has diametrically opposed flat surfaces, as best seen in FIG. 42, for a purpose described below in greater detail. The angle A5 is defined between plane P20 containing the central longitudinal axis of bone insertion element 91 and a plane P21 containing the central longitudinal axis of the handle 92. Angle A5 approximates the valgus angle of the distal femur, and valgus rods having different angles A5 can be provided. For example, valgus rods can be provided having angles A5 of 3 degrees, 5 degrees and 7 degrees, respectively. A single valgus rod can be used for both left and right knees merely by reversing its orientation. Accordingly, a top surface of the valgus rod can be provided with indicia, such as the word "left", indicating orientation for use on the left knee, and a bottom surface of the valgus rod can be provided with different indicia, such as the word "right", indicating orientation for use on the right knee. When the "left" indicating indicia faces upwardly, the valgus rod will be oriented for use on the left knee, and when the "right" indicating indicia faces upwardly, the valgus rod will be oriented for use on the right knee.

Figure 27:
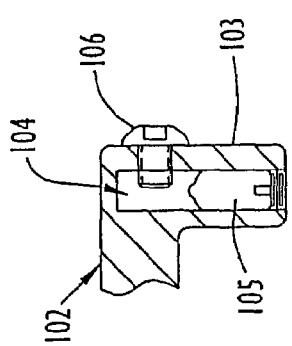
FIG. 27 is a broken sectional view of a horizontal linking bar of the linking instrument taken along line E—E of FIG. 24.
Figure 26:
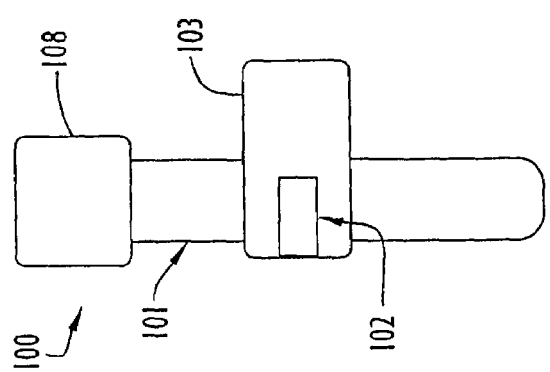
FIG. 26 is an opposite side view of the linking instrument.

A linking instrument 100 for use with posterior resection block 70 and valgus rod 90 is illustrated in FIGS. 24–27. Linking instrument 100 includes a vertical linking bar 101 and a horizontal linking bar 102 perpendicular to vertical linking bar 101. The horizontal linking bar 102 has an end joined to an L-shaped socket 103. As best shown in FIG. 27, socket 103 extends anteriorly from the horizontal linking bar 102 and has a channel 104 extending therethrough from top to bottom. A detent is associated with the channel 104 and may comprise a ball plunger 105 mounted in and partially occupying the cross-sectional dimension of the channel 104. A portion of the channel cross-sectional dimension not occupied by plunger 105 is of a size and configuration to receive the vertical linking bar 101 therethrough, the vertical linking bar being shown removed from the channel 104 in FIG. 27. The vertical linking bar 101 is slidably disposed in channel 104 and is confined in a desired position in the channel by the detent, such as the plunger 105 and a locking screw 106 engaged with a longitudinal groove 107 formed in a side wall of the vertical linking bar. An upper end of the vertical linking bar 101 carries a fixture 108 having a passage 109 extending therethrough from anterior to posterior, with a central longitudinal axis of passage 109 being perpendicular to the central longitudinal axis of the vertical linking bar and also being perpendicular to a central longitudinal axis of horizontal linking bar 102. The passage 109 has a cross-sectional size and configuration to receive the handle 92 of valgus rod 90 with a close fit. The horizontal linking bar 102 has a size and configuration in cross-section to be received in the channel 79 of the posterior resection block 70 with a close fit. The linking instrument may be made available in different sizes.

Figure 28:
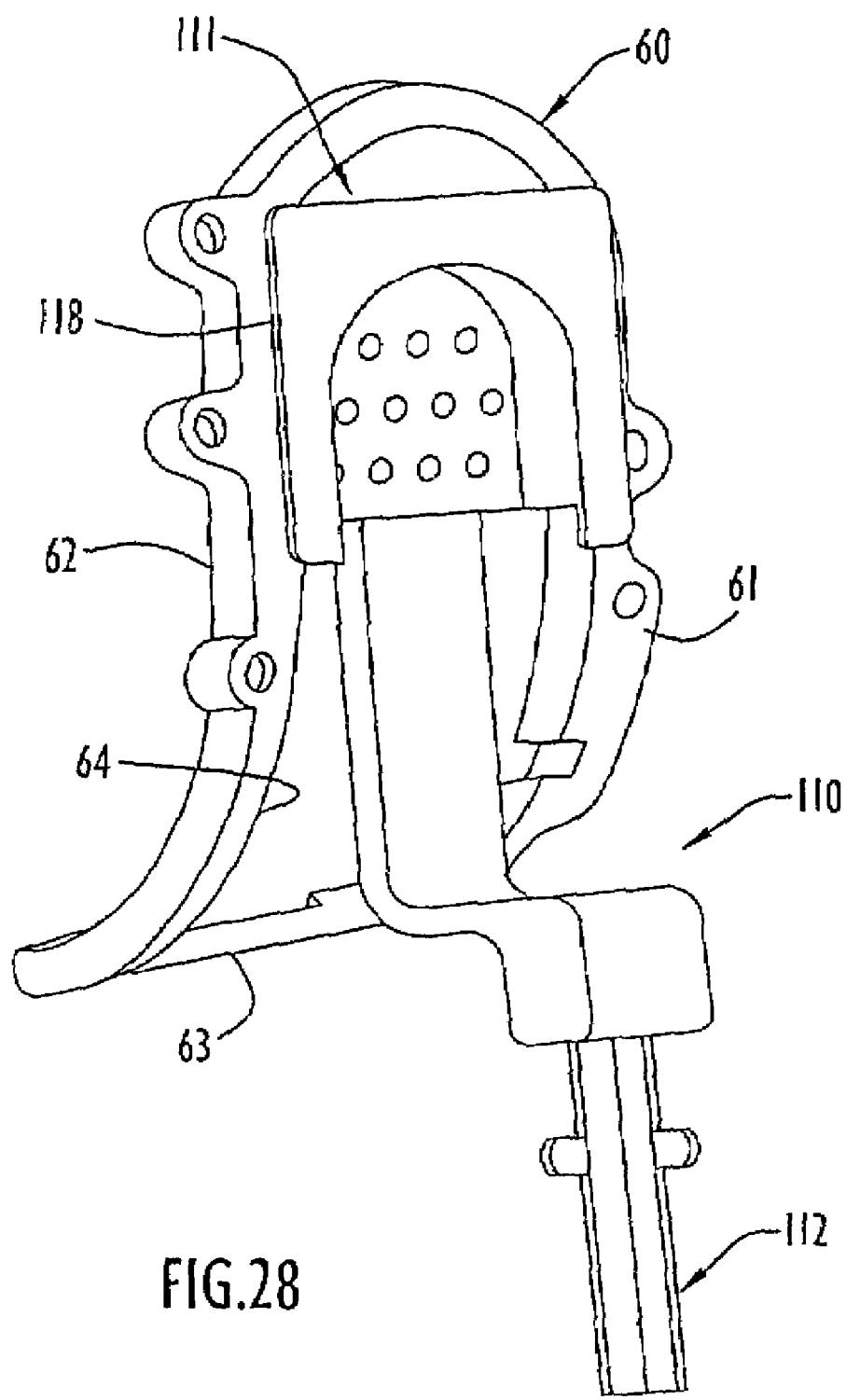
FIG. 28 is a perspective view of the femoral resurfacing guide with a femoral resurfacing instrument used in the methods of the present invention.
Figure 30A:
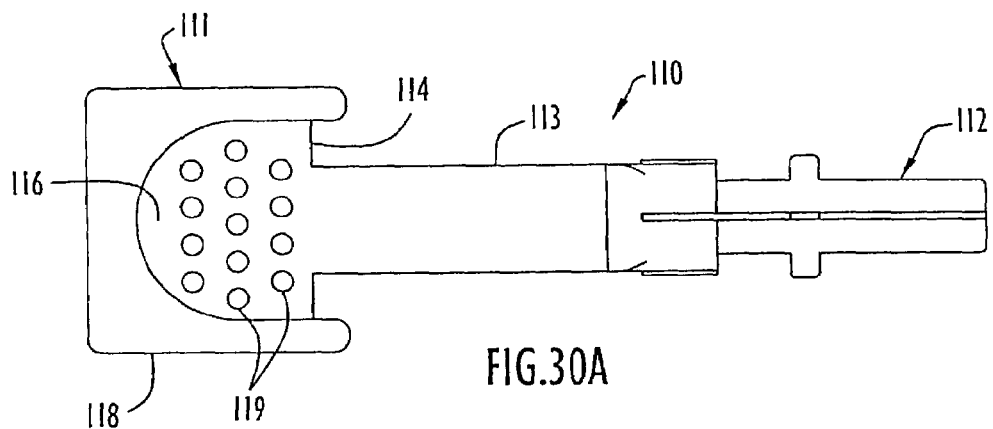
FIG. 30A is a top view of the femoral resurfacing instrument of FIG. 28.
Figure 29A:
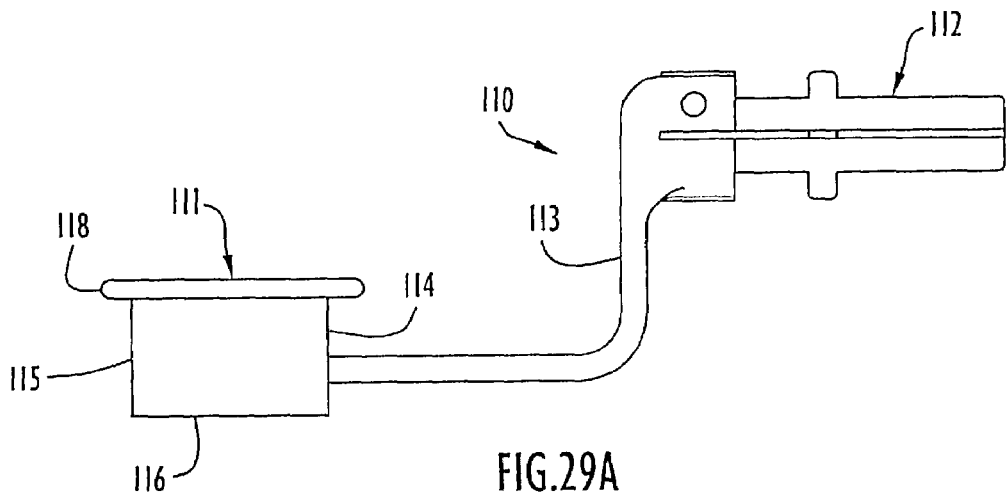
FIG. 29A is a side view of the femoral resurfacing instrument of FIG. 28.
Figure 31A:
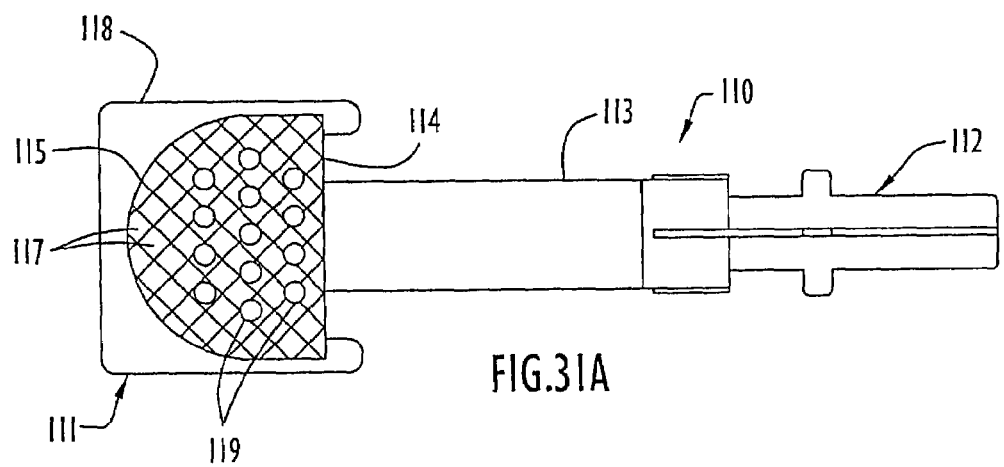
FIG. 31A is a bottom view of the femoral resurfacing instrument of FIG. 28.

FIG. 28 illustrates a femoral resurfacing or tissue removing instrument 110 for use with the femoral resurfacing guide 60 to resurface a femoral condyle to accommodate the femoral component of the knee joint prosthesis. The femoral resurfacing instrument 110 is illustrated as but is not limited to a femoral rasp, which may be provided in sizes corresponding to the sizes of the femoral resurfacing guide. For example, a Size 2 femoral rasp may be provided for use with a Size 2 femoral resurfacing guide. However, the femoral rasp can be made available in other sizes corresponding to other sizes of the femoral resurfacing guide. It should be appreciated, however, that the resurfacing instrument may be size independent. Although size specific resurfacing instruments may be made available for optimal or enhanced performance, a generic resurfacing instrument may be used with the various sizes of femoral resurfacing guides. The femoral resurfacing instrument or rasp 110, as best illustrated in FIGS. 28, 29A, 30A and 31A, includes a cutting member, a tissue removing member, or an abrading member 111 connected to an angled flange or shaft 113 by which the tissue removing member is coupled with a handpiece, which may be a manual handpiece or a powered handpiece. A rearward end of the flange 113 is shown connected to an adapter 112 designed for connection to a standard powered handpiece or instrument by which the tissue removing member 111 is reciprocated. Various adapters or other connections may be used to couple the tissue removing member with a powered handpiece or instrument. Although powered operation is optimal, the tissue removing member may be connected to or formed with various handpieces by which the tissue removing member may be manually moved to effect resurfacing, and such handpieces may be integral and unitary with the tissue removing member or separate therefrom. The angled flange 113 has a 90 degree bend with a rearward portion of the flange extending upwardly from the bend and a forward portion of the flange extending forwardly from the bend at a right angle to the rearward portion as shown in FIG. 29A. The tissue removing member 111 has a bottom wall 116 with a straight rear edge 114 joined to opposite ends of an upstanding curved side wall 115. The side wall 115 may follow a configuration substantially corresponding to the anterior configuration of the femoral component and forms an abutment for engaging the inside surface 64 of the rail member of the femoral resurfacing guide 60. The bottom wall 116 of the tissue removing member is circumscribed by rear edge 114 and side wall 115, and a lower surface of bottom wall 116 is covered in a pattern of cutting teeth 117 to define a cutting, tissue removing or abrading surface that fits within the track of the rail member of the femoral resurfacing guide 60. The tissue removing surface is illustrated as being planar but may be non-planar and may be curved. The cutting teeth 117 provide a bidirectional or multidirectional cutting action in that the cutting teeth 117 are configured to remove tissue as the tissue removing member is moved in more than one direction along the delineated area, for example, anteriorly and posteriorly along the delineated area. Accordingly, tissue removal is accomplished in response to both forward/anterior and rearward/posterior movements of the tissue removing member along the area delineated by the rail member. A ledge 118 protrudes from the top of side wall 115 and the distance between the ledge 118 and the tissue removing surface limits or controls the depth of resurfacing via engagement of a lower surface of the ledge with an abutment wall carried by the rail member of the femoral resurfacing guide 60. Particularly, the tissue removing surface protrudes a predetermined distance from the back or posterior surface of the rail member when an engagement wall formed by the lower surface of the ledge engages an abutment wall formed by the front surface of the rail member, such that the ledge defines a stop limiting the depth of resurfacing as described further below. An upper surface of bottom wall 116 is recessed below the ledge 118, and a plurality of apertures 119 may be formed through bottom wall 116 to allow passage of bone fragments or other anatomical tissue debris away from the tissue removing surface. The resurfacing instrument thusly controls the depth to which tissue is removed and effects an improved bone surface for implantation compared to current conventional techniques.

Figure 30B:
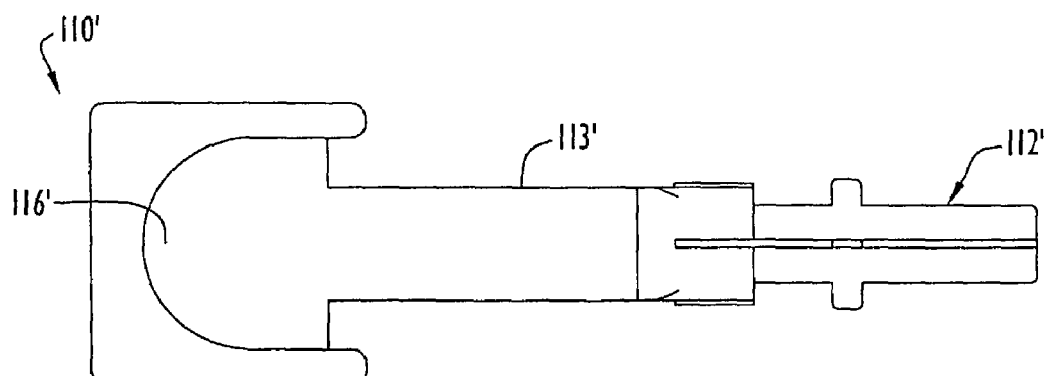
FIG. 30B is a top view of the modified femoral resurfacing instrument of FIG. 29B.
Figure 29B:
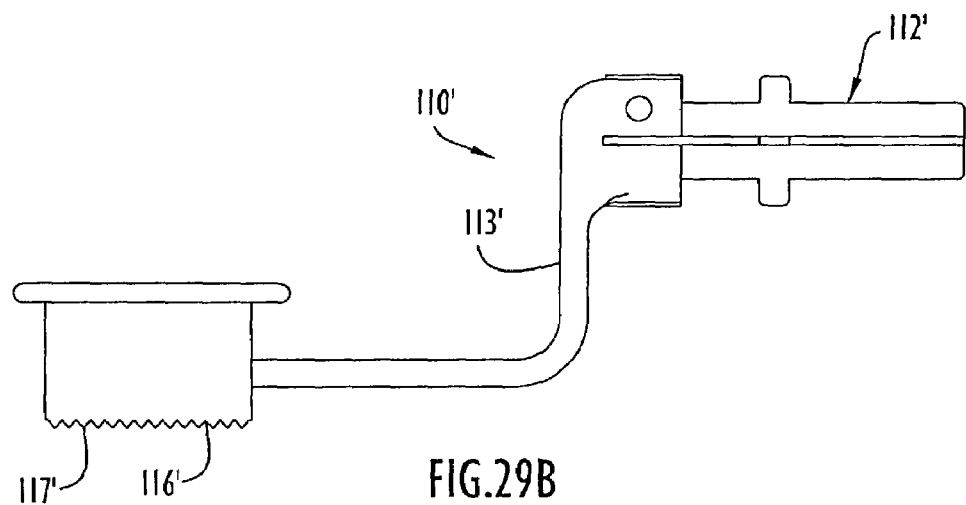
FIG. 29B is a side view of a modified femoral resurfacing instrument for use with the femoral resurfacing guide in the methods of the present invention.
Figure 31B:
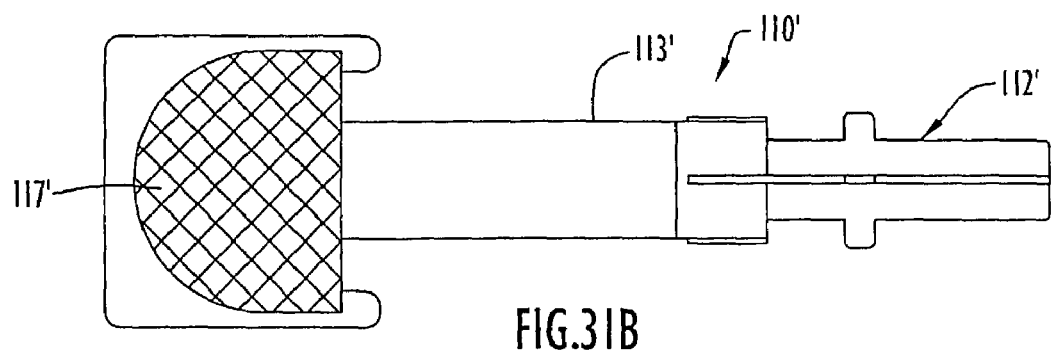
FIG. 31B is a bottom view of the modified femoral resurfacing instrument of FIG. 29B.

A modified and preferred femoral rasp for use as the femoral resurfacing instrument in the methods of the present invention is illustrated at 110' in FIGS. 29B, 30B and 31B. The femoral rasp 110' is similar to femoral rasp 110 but does not have apertures in bottom wall 116'. Of course, the bottom wall 116' could be provided with apertures as described for bottom wall 116 of femoral rasp 110. The cutting teeth 117' for rasp 110' differ from the cutting teeth 117 for rasp 110 in that the cutting teeth 117' are deeper and larger and provide a monodirectional or unidirectional cutting action. Accordingly, the cutting teeth 117' are configured to remove anatomical tissue as the tissue removing member is moved in one direction, for example rearwardly or posteriorly, along the delineated area. Of course, the cutting teeth 117' can be configured to effect unidirectional cutting as the tissue removing member is moved anteriorly or forwardly along the delineated area. Also, the connection used in femoral rasp 110' to connect the flange 113' with the adapter 112' is different than the connection used in femoral rasp 110.

Figure 32:
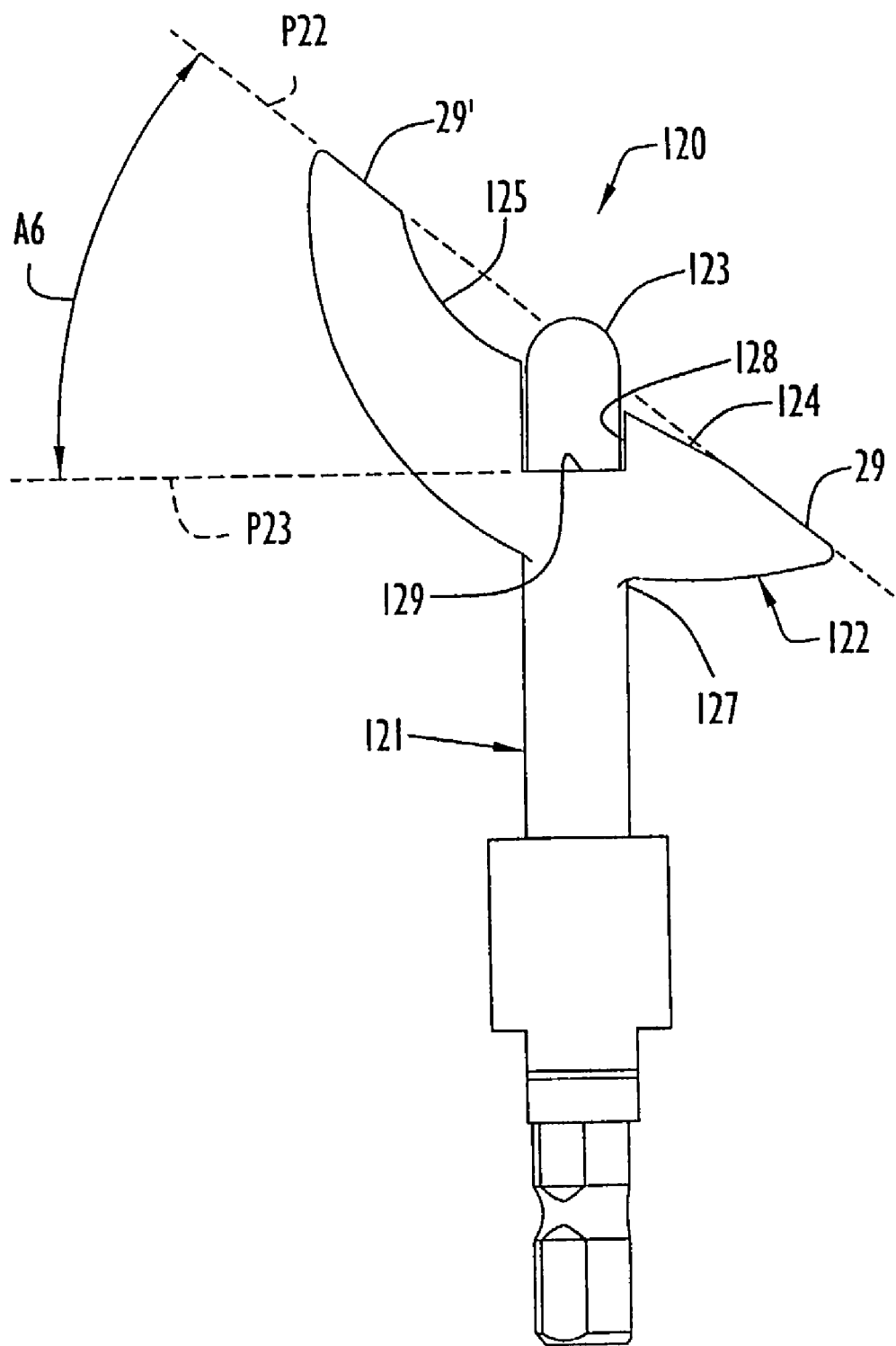
FIG. 32 is side view of a femoral fin punch for use with the trial femoral component in the methods of the present invention.
Figure 33:
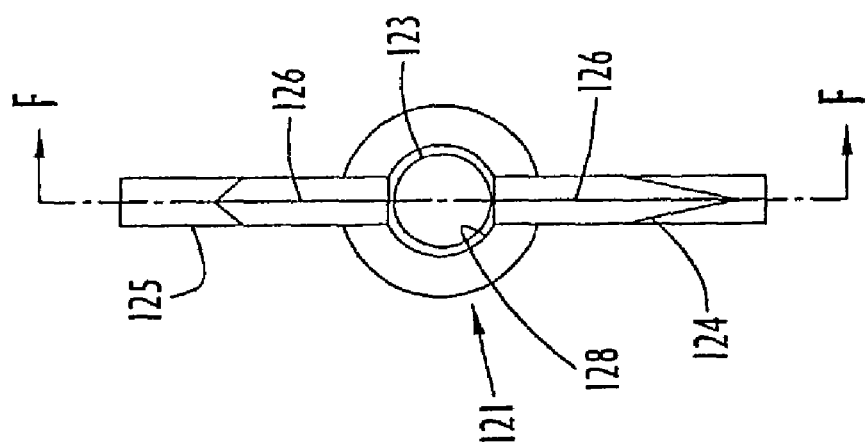
FIG. 33 is an end view of the femoral fin punch.
Figure 34:
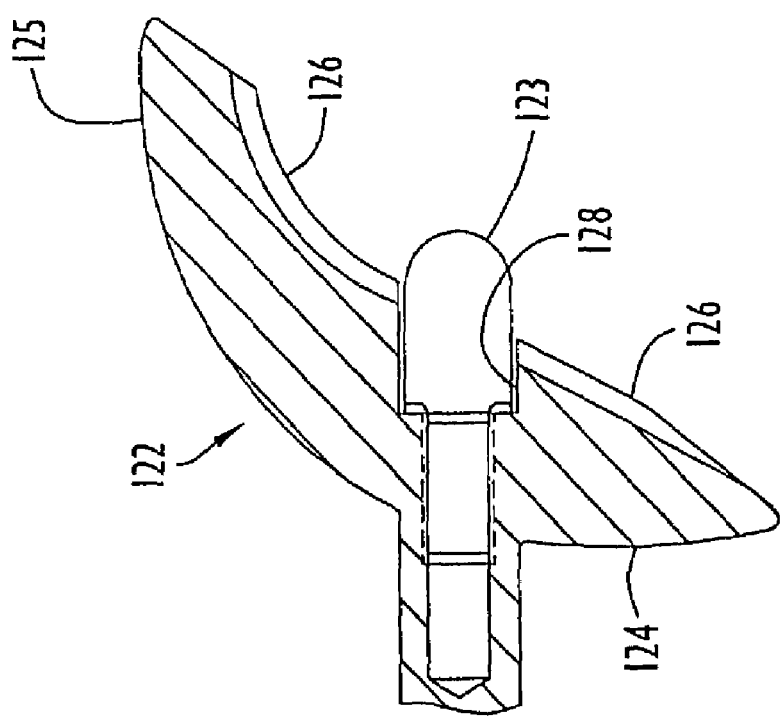
FIG. 34 is a broken sectional view of the femoral fin punch taken along line F—F of FIG. 33.

A femoral fin punch 120 is shown in FIGS. 32–34 for use with trial femoral component 40 to prepare the femur for the femoral fixation fin of the actual femoral component. The femoral fin punch 120 has a rearward end or handle 121 and a forward end or punch member 122 mounted to or formed as part of the handle 121. The punch member 122 has a peg element 123 axially aligned with handle 121 and a fin element comprising an anterior fin element 124 extending anteriorly from peg element 123 and a posterior fin element 125 extending posteriorly from peg element 123. The anterior and posterior fin elements have inner edges 126, respectively, that are pointed to penetrate bone. The peg element 123 has a configuration corresponding to the femoral fixation peg of the actual femoral component, and the anterior and posterior fin elements 124 and 125 have configurations corresponding to the anterior and posterior femoral fixation fin segments of the actual femoral component. The anterior and posterior fin elements 124 and 125 are dimensioned to fit within the anterior and posterior slot segments 42 and 43, respectively, of the trial femoral component 40 with a close fit. The peg element 123 is configured to fit in the bore hole 41 of the trial femoral component 40 with a close fit. When fully inserted in the bore hole and slot segments of the trial femoral component during a knee replacement procedure, the peg element seats in a previously drilled hole in the femur and the anterior and posterior fin elements punch depressions in the bone of the proper configuration, size and depth to receive the corresponding anterior and posterior femoral fixation fin segments of the actual femoral component as described further below. In the femoral punch 120, the peg element 123 is mounted or disposed in a recess 128 between the anterior and posterior fin elements, and the peg element protrudes from a bottom surface 129 of the recess contained in a plane P23. An anterior edge surface 29 of anterior fin element 124 and a posterior edge surface 29' of posterior fin element 125 are contained in plane P22 forming angle A6 with plane P23. When the punch member 122 is fully inserted in the trial femoral component, the anterior edge surface 29 abuts the end surface 45 of the anterior slot segment and the posterior edge surface 29' abuts the end surface 46 of the posterior slot segment to form a depth stop limiting penetration of the punch member into the femur. In a representative but not limiting embodiment, angle A6 is 38 degrees.

The instruments and methods of the present invention are most preferably used with the unicompartmental knee joint prostheses disclosed in the referenced application, which closely replicate the geometry and kinematics of the medial compartment of the knee, but may be used or adapted for use with other knee joint prostheses. Use of the instruments and methods of the present invention as described below is applicable to medial or lateral compartment knee joint replacement in cases of unicompartmental disease without contraindications, and the disclosure of a medial compartment procedure should be construed as illustrative and not limiting. Projected femoral and tibial component sizes and alignment goals are determined prior to surgery through radiographic analysis including standard weight-bearing anterior-posterior and lateral films, which are also used to diagnose medial compartment disease. A diagnostic arthroscopy may be performed to confirm the absence of contraindications including tricompartmental disease, inflammatory arthritic disorders such as rheumatoid arthritis, ACL insufficiency and crystal-induced arthropathies.

In a method of unicompartmental knee replacement according to the present invention, the medial, lateral, superior and inferior borders of the patella are marked with the knee in flexion. The tibial tubercle and joint line are palpated. Surgery is initiated by accessing the medial compartment of the knee through a 3–5 inch medial perapatellar incision beginning at the medial border of the patella and carried distally to the level of the tibial tubercle, with the incision paralleling the medial border of the patellar tendon to expose the medial compartment of the knee. The proximal portion of the retinacular incision is extended proximally and medially in a "hockey stick" fashion just below the distal fibers of the vastus medialis. The incision can be extended proximally and/or distally as needed. If present, the medial patellar osteophyte should be removed. The medial border of the patella can be removed, as needed, to facilitate exposure. In performing the medial meniscectomy, it may be helpful to excise the anterior horn of the meniscus and complete the meniscectomy following the proximal tibial resection.

Figure 35:
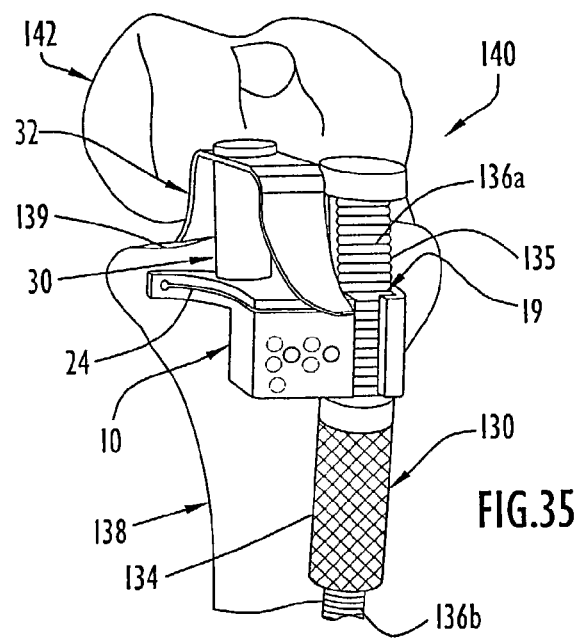
FIG. 35 is a broken perspective view showing the tibial stylus assembled to the tibial crosshead and illustrating the tibial crosshead attached to a tibial alignment guide.
Figure 36:
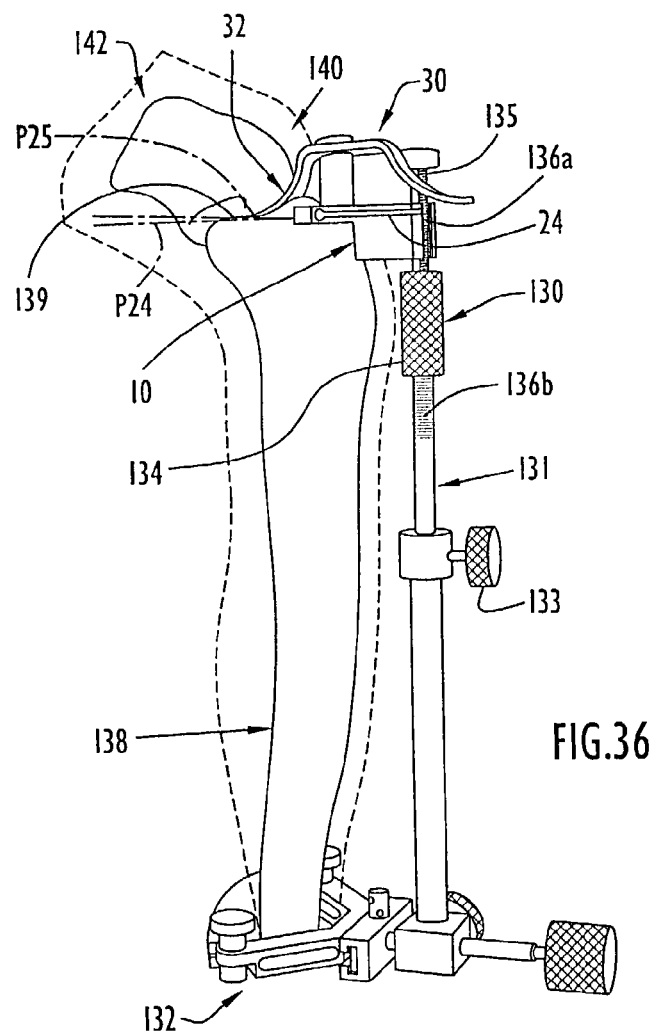
FIG. 36 is a broken perspective view showing the tibial alignment guide positioned on the tibia with a stylus arm of the tibial stylus resting on the lowermost surface of the medial tibial plateau.

As shown in FIGS. 35 and 36, the thusly exposed knee 140, which is shown as a left knee but which may be a right knee, is flexed to 90 degrees and the appropriate "left" or "right" tibial cutting guide or crosshead is attached to a tibial alignment guide. FIGS. 35 and 36 shown the tibial cutting guide 10 attached to a tibial alignment guide 130 including an extendable and retractable shaft assembly 131 having a lower end mounted to an adjustable ankle clamp 132. Selected extension and retraction of the shaft assembly 131 vertically is permitted via adjusting screw 133. The extendable shaft assembly 131 includes an extendable upper shaft 135 having a wider upper grooved portion 136a connected with a narrower lower rod portion 136b upon which an adjusting sleeve 1234 is disposed. The lower portion 136b is externally threaded, and the adjusting sleeve 134 is internally threaded to permit the adjusting sleeve to be rotated relative to the upper shaft to effect movement of the adjusting sleeve vertically upwardly and downwardly along the upper shaft. The tibial alignment guide may be a standard extramedullary tibial alignment guide of the type sold by Wright Medical Technology as Part Nos. K0063001 and K0040103. FIGS. 35 and 36 show the tibial cutting guide 10 assembled to the tibial alignment guide 130 by lowering the adjusting sleeve 134 to permit insertion of the lower portion 136b of upper shaft 135 through the anterior opening of channel 19 and by thereafter raising the adjusting sleeve so that the grooved portion 136 is positioned snugly in the channel 19 of the tibial cutting guide with the tibial cutting guide resting at the mid-point of the proximal tibial alignment guide.

The tibial alignment guide 130, with the tibial cutting guide 10 assembled thereto, is placed onto the tibia 138 by applying the ankle clamp 132, with the ankle clamp positioned at or slightly medial to the mid-point of the medial and lateral malleoli as shown in FIG. 36. The shaft assembly 131 is placed parallel to or along the long axis of the tibia, particularly the tibial shaft, and is positioned proximally at the medial third of the tibial tubercle or another appropriate landmark for correct tibial rotation. Placing the shaft assembly parallel in the sagittal plane with the long axis of the tibia provides a downward posteriorly sloped tibial resection, such as a five degree posteriorly sloped tibial resection, through the resection slot 24 of the tibial cutting guide 10 relative to the plane perpendicular to the long axis. Moving the shaft assembly away from the ankle increases posterior slope while moving the shaft assembly toward the ankle joint reduces the posterior slope. Different tibial cutting guides or crossheads providing different resection angles may be provided so that the posterior slope can be varied by using a different tibial cutting guide. As explained above, a tibial cutting guide can be provided to obtain a tibial resection of neutral, zero or no slope or angle relative to the plane perpendicular to the long axis. It is desirable to match the anatomic slope as closely as possible while avoiding excessive posterior angulation. The posterior wall of the tibial cutting guide is positioned adjacent the anterior tibia and conforms to and accommodates the anatomic configuration or geometry of the anterior tibia to facilitate the minimal incision technique.

Figure 37:
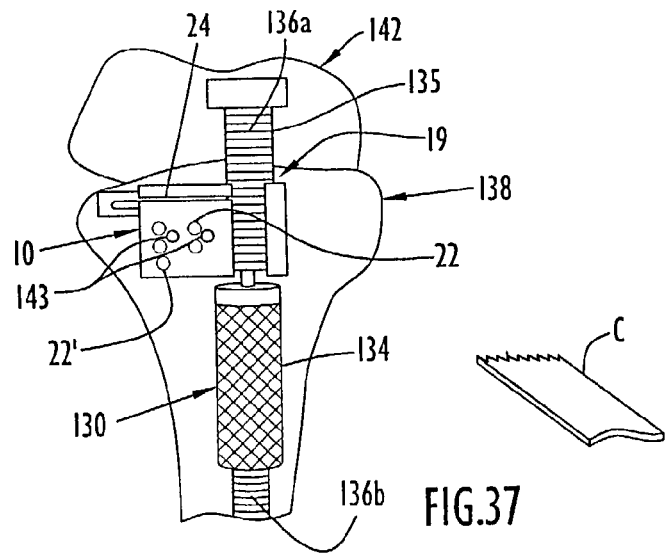
FIG. 37 is a broken perspective view of the tibial crosshead fixated to the tibia in the proper position and showing the tibial stylus removed from the tibial crosshead.
Figure 39A:
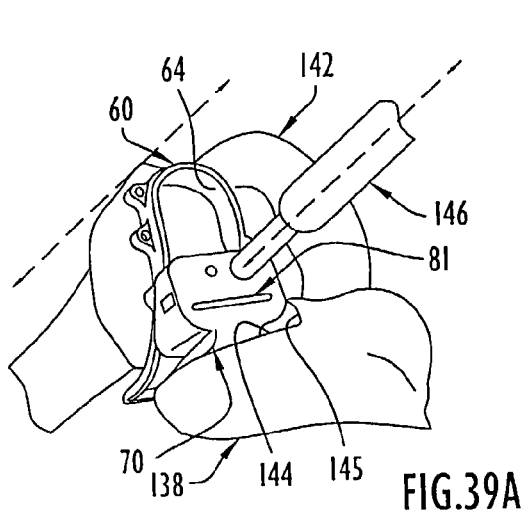
FIG. 39A is a broken perspective view illustrating the femoral resurfacing guide/posterior resection block assembly positioned on the unprepared femoral condyle.
Figure 39B:
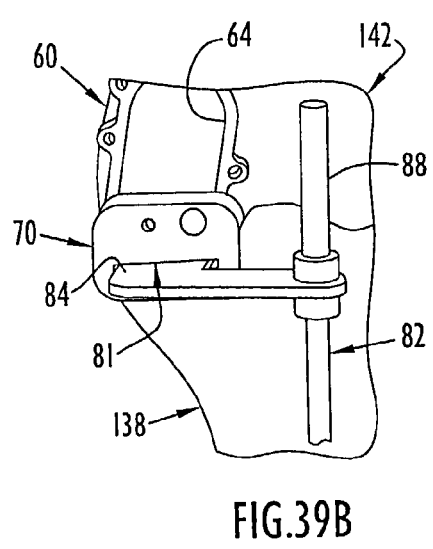
FIG. 39B is a broken anterior view illustrating the femoral resurfacing guide/posterior resection block assembly positioned on the unprepared medial femoral condyle with the femoral alignment module assembled to the posterior resection block.

If the tibial stylus 30 is being used, it is assembled onto the tibial cutting guide 10 by inserting the stem 37 of the tibial stylus through an appropriate through hole 28 of the tibial cutting guide until the tibial stylus is locked in place via the detent ball 38 as shown in FIGS. 35 and 36. The shaft assembly 131 is adjusted to adjust the height of the tibial cutting guide 10 so that the selected stylus arm is located to rest on the tibial plateau 139. Depending on which stylus arm is selected, the tibial resection will be made, in the case of a tibial stylus having 4 mm and 6 mm stylus arms, either 4 mm or 6 mm below the level where the selected stylus arm rests on the proximal tibia. FIGS. 35 and 36 illustrate the lower surface of end 39 of the stylus arm 32, i.e. a 6 mm stylus arm, resting on the tibial plateau for a tibial resection 6 mm below the level where the stylus arm 32 rests on the tibial plateau. Depending on the preferences of the surgeon, the lower surface of the stylus arm may be placed on the lowest surface of the tibial plateau. Throughout this procedure, the knee 140 is maintained in flexion, with the tibia 138 rotated 90 degrees relative to the femur 142 as shown in the drawings. The anatomic curvature of stylus arm 32 accommodates the anatomic geometry of the distal surface of the femoral condyle with the end of the stylus arm positioned between the femoral condyle and tibial plateau with the knee in flexion and also with the knee in extension. Proper tibial rotation is maintained, and the tibial cutting guide 10 is fixated to the tibia 138 via fixation pins or other fixation elements 143 inserted through the middle pair of fixation holes 22 of the tibial cutting guide 10 as shown in FIG. 37. Typically, 0.125 inch (3.2 mm) headless fixation pins will be utilized. In hard or sclerotic bone, quick disconnect drill bits may be necessary to prepare holes for the fixation pins. Prior to fixation of the tibial cutting guide 10 to the tibia, the femoral alignment module 82 may be used to evaluate and confirm proper positioning of the resection slot 24 by inserting the foot 84 of the femoral alignment module in the resection slot 24 as described below for the resection slot of the posterior resection block 70 and as shown in FIGS. 39B and 40 for the posterior resection block.

The proximal tibial resection may be performed with or without the tibial alignment guide 130 in place, in that the tibial alignment guide may be removed from the tibial cutting guide once the tibial cutting guide has been fixated to the bone and prior to the proximal tibial resection being performed. To remove the tibial alignment guide, the adjusting sleeve 134 is turned so that the narrower rod portion 136b of upper shaft 135 may be withdrawn through the anterior opening of the channel 19. Prior to performing the proximal tibial resection, the depth of the tibial cutting guide 10 may be further adjusted by removing the tibial cutting guide from the middle pair of fixation pins 143 and moving the tibial cutting guide over the fixation pins so that the fixation pins are inserted and received in the upper pair of fixation holes 22 at a plus 2 mm position or are inserted and received in the lower pair of fixation holes 22 at a minus 2 mm position. In this manner, the tibial cutting guide can be adjusted upwardly and downwardly to individualize for the particular patient the amount of bone removed from the tibia for the proximal tibial resection. For additional fixation, a divergent headless fixation pin or other fixation element may be applied via the fixation hole 22'.

Figure 38:
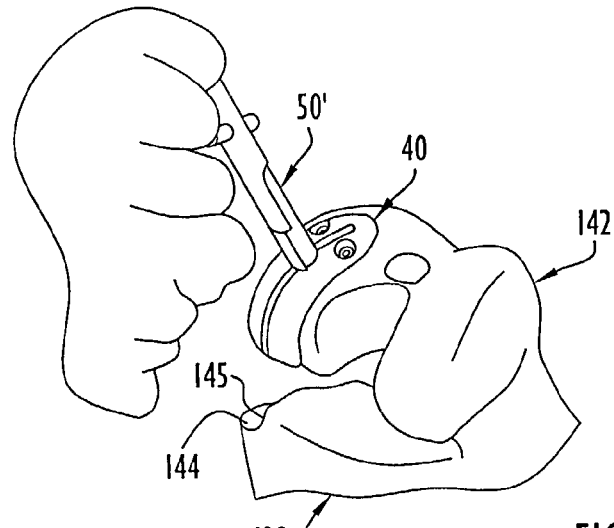
FIG. 38 is a broken perspective view showing the trial femoral component located on the femur via the modified handle assembled to the trial femoral component.

With the tibial cutting guide 10 fixated to the tibia in the correct position, the tibial stylus 30 is removed therefrom and a proximal resection of the tibia is initiated using a cutting member C through the resection slot 24 as depicted in FIG. 37. Typically, a one half inch wide (0.050 inch/1.3 mm thick) oscillating planar saw blade driven by a powered handpiece or instrument is used as the cutting member inserted through resection slot 24. The cutting member may be introduced or inserted in the slot 24 from the anterior and/or the medial side of the tibial cutting guide. A planar resected surface 144 is thusly formed in the proximal tibia as shown in FIG. 38 and extends downwardly from anterior to posterior at the previously selected posterior slope or angle relative to the plane perpendicular to the long axis as shown by plane P24 in FIG. 36, but can alternatively be of zero, neutral or no slope or angle, i.e. perpendicular to the long axis, as shown by plane P25 in FIG. 36. The proximal tibial resection is completed by forming a sagittal resected surface 145, typically using a reciprocating saw blade, aligned with the lateral border of the medial femoral condyle while taking care to avoid the anterior and posterior cruciate ligaments, the sagittal resected surface being shown in FIG. 38. In an alternative method, the sagittal resected surface 145 can be made first using the reciprocating saw blade, which can be left in place on the proximal tibia to act as a landmark for making the planar resected surface 144 in the proximal tibia as discussed above. If necessary, the posterior horn of the medial meniscus may be removed prior to preparing the femur.

Following complete exposure and appropriate soft tissue release, preliminary sizing for the actual femoral component to be implanted is determined by utilizing a trial femoral component. To facilitate the femoral procedure, a line may be etched or marked on the femoral condyle to indicate the weight bearing axis, which may be determined by observing the line of visible wear along the femoral condyle. Based on pre-operative templating, a selected size trial femoral component is attached to the trial component handle as described above. FIG. 38 shows trial femoral component 40 attached to handle 50', with the handle 50' grasped by the surgeon to locate the trial femoral component 40 on the femur 142. The trial femoral component 40 is positioned on the unprepared femoral condyle, as shown for the medial femoral condyle, to estimate correct sizing based on medial-lateral component width and overall anterior-posterior sizing. Because a posterior femoral resection has not yet been performed, the anterior/superior location of the trial femoral component will not represent the final location of the actual femoral component. Following the posterior femoral resection, the femoral component will be positioned approximately 7 mm anterior/superior to its position during trialing. Ultimately, the anterior portion of the actual femoral component should be positioned on the femoral condyle at the tidemark between the degenerative weight-bearing surface and the healthier articular cartilage. The femur may be marked with methylene blue to indicate the central weight-bearing line and medial-lateral aspects of the trial femoral component.

Final component sizing is determined with the femoral resurfacing guide 60 and posterior resection block 70. As shown in FIG. 39A, the appropriate size "left" femoral resurfacing guide for left knee implantation or the appropriate size "right" femoral resurfacing guide for right knee implantation may be attached to the appropriately sized posterior resection block 70 to form a one-piece assembly or construct by inserting the attachment posts 76 of the posterior resection block 70 in the through holes 67 of the femoral resurfacing guide 60. FIG. 39A depicts the "left" femoral resurfacing guide 60 attached to the posterior resection block 70. If desired, a threaded handle 146 can be inserted into the threaded hole 77 of the posterior resection block 70 to extend parallel to the planar resection slot 81 and perpendicular to the anterior or front wall of the resection block. The handle 146 assists in manipulating the femoral resurfacing guide 60/posterior resection block 70 assembly for placement on the femur and may be used to evaluate the flexion/extension position and the varus/valgus position of the femoral instrumentation. Of course, the femoral resurfacing guide 60 and posterior resection block 70 need not be assembled prior to being placed on the femur but can be placed on the femur in separate procedural steps. Accordingly, the following procedural description in which the femoral resurfacing guide 60 and posterior resection block 70 are assembled prior to being positioned and aligned on the femur should be considered illustrative and not limiting.

The femoral resurfacing guide 60/posterior resection block 70 assembly is positioned on the femur with the knee in flexion and the base plate 74 of the resection block disposed between the posterior aspect of the femoral condyle and the resected surface 144 as shown in FIG. 39A. The stylus 59 of the femoral resurfacing guide contacts the bone for proper positioning of the femoral resurfacing guide and to control the depth of resurfacing. The stylus 59 prevents the femoral resurfacing guide from rolling over into hyperextension and provides an indication of where the prosthetic femoral component will transition into the bone. If the surgeon attempts to fully seat the femoral resurfacing guide against the femur, the position and size of the stylus 59 prevents mal-positioning of the femoral resurfacing guide while maintaining the proper depth of resurfacing. The bottom surface of base plate 74 of the posterior resection block 70 will rest on the previously formed resected surface 144 of the proximal tibia to ensure that a planar posterior resection of the femur established via resection slot 81 is parallel to the tibial resection 144 for proper balancing of the implanted knee joint. If the joint space is too loose, spacers or shims can be introduced between the base plate and the bone to maintain the parallel relationship between the tibial resection and the posterior portion of the femoral resurfacing guide/posterior resection block assembly. If the posterior portion of the femoral resurfacing guide/posterior resection block assembly is maintained parallel to the tibial resection, the posterior resection of the femur will be parallel to the tibial resection. This linking of the femoral resection to the tibial resection helps the surgeon balance the joint space and determine proper positioning of the instruments and prosthesis.

Proper alignment and positioning may be established and confirmed using an extramedullary technique and/or an intramedullary technique. The femoral resurfacing guide 60/posterior resection block 70 assembly is positioned and aligned on the unprepared femoral condyle using one or more of the following extramedullary steps or techniques and, preferably, all or a combination of the following extramedullary steps or techniques. In a first step or technique, the knee 140 is flexed to 90 degrees and the handle 146 is positioned parallel to the femur and perpendicular to the tibia when viewed from the lateral or medial side as shown by dotted lines in FIG. 39A. The handle 146 is used to evaluate flexion/extension and varus/valgus positioning. The planar resected surface 144 of the proximal tibia may also be used to confirm correct positioning of the posterior resection block 70 in that the bottom surface of the base plate 74 rests on the resected surface 144 with resection slot 81 parallel to resected surface 144. In a second step or technique, the femoral resurfacing guide 60/posterior resection block 70 assembly is positioned in the correct medial-lateral and rotational position along the distal weight bearing surface of the femoral condyle to obtain maximum femoral coverage as shown in FIG. 39B. The inside surface 64 or track of the rail member corresponds to the outer medial-lateral geometry of the femoral component and thusly provides an indication of maximum femoral coverage, with the stylus 59 indicating where the femoral component will transition into the bone. A third step or technique for positioning and aligning the femoral resurfacing guide 60/posterior resection block 70 assembly involves ensuring that the femoral resurfacing guide/posterior resection block assembly is rotated correctly for femoral alignment as also shown in FIG. 39B. The prosthetic femoral component disclosed in the application incorporated herein by reference provides an anatomic angle, such as 7 degrees, between the distal and posterior portions, which should closely replicate the anatomic geometry of the femoral condyle. Final rotational positioning may be confirmed via the inside surface 64 of the femoral resurfacing guide 60 and by utilizing the femoral alignment module 82 as depicted in FIGS. 39B and 40. As shown in FIGS. 39B and 40, the foot 84 of the femoral alignment module 82 is inserted in the resection slot 81 of posterior resection block housing. The foot 84 protrudes posteriorly from the back surface of the housing for resection block 70, thereby establishing a location for a posterior resection of the femur through the slot 81 of the resection block. In a fourth step or technique also represented by FIGS. 39B and 40, the foot 84 is inserted in the resection slot 81 and the check rod 88 of the femoral alignment module 82 is used to confirm that the femoral resurfacing guide/posterior resection block is parallel to the long axis of the femur 142 and perpendicular to the long axis of tibia 138, thereby ensuring proper flexion-extension positioning.

An alternative or additional alignment technique includes the intramedullary alignment technique represented in FIGS. 41 and 42 and involves initiating or forming an opening 148 in the femoral intramedullary canal 149, typically using a ⅜ inch (9.5 mm) diameter drill bit or cutting member. Routine irrigation and aspiration should be performed to reduce the possibility of fat emboli. The femoral resurfacing guide 60/posterior resection block 70 assembly is coupled with the appropriate size linking instrument 100 to form a one-piece assembly or construct by inserting the horizontal linking bar 102 in the channel of the posterior resection block 70 as shown in FIG. 42. An intramedullary or valgus rod 90 having the appropriate angle, such as 3 degrees, 5 degrees or 7 degrees, is selected and is oriented via the indicia so that the valgus rod is positioned for use on the appropriate knee. For the illustrated method, the indicia indicating "left" is positioned to face upwardly for unicompartmental surgery on the left knee. The valgus rod 90 is placed into the intramedullary canal via the opening 148 without seating the vanes 93 of the valgus rod into the bone as shown in FIGS. 41 and 42. The one-piece assembly or construct formed by the femoral resurfacing guide/posterior resection block assembly and the linking instrument is coupled with the valgus rod 90 by placing the handle 92 of valgus rod 90 through the passage 109 of fixture 108. The flat surfaces on the handle 92 mate with the flat walls of passage 109. The femoral resurfacing guide/posterior resection block assembly is then positioned and aligned utilizing the extramedullary alignment steps or techniques discussed above. Femoral alignment is finalized by impacting the end of handle of the valgus rod 90 and fully seating the vanes 93 in the intramedullary canal. The seated vanes 93 prevent the valgus rod from rotating.

Figure 43:
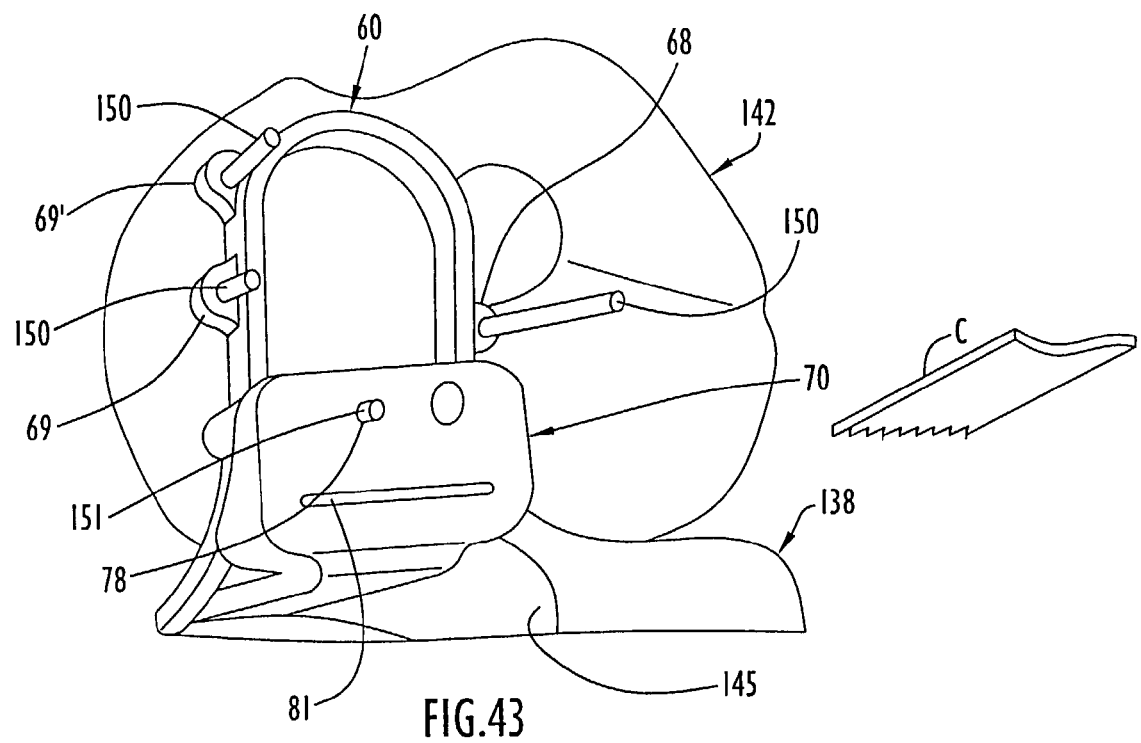
FIG. 43 is a broken perspective view illustrating the properly positioned femoral resurfacing guide/posterior resection block assembly fixated to the femur.

The femoral resurfacing guide 60/posterior resection block 70 assembly is correctly positioned with base plate 74 flush against the tibial resected surface 144 and against the posterior femoral condyle, with or without the use of shims or spacers for the base plate. The femoral resurfacing guide 60 is pinned in place via fixation pins or other fixation elements 150 inserted in the holes of eyelets 68, 69 and 69', respectively, as shown in FIG. 43. Typically, 0.125 inch (3.2 mm) headless fixation pins 150 are used. An additional fixation pin or other fixation element 151 is placed in the divergent fixation hole 78 of the posterior resection block 70 to ensure it remains stable during resection of the posterior femoral condyle. For hard or sclerotic bone, it may be necessary to pre-drill the holes with 0.125 inch (3.2 mm) quick disconnect drill bits or other cutters. The eyelets are located and oriented to cooperate with the fixation pins inserted therein to retract the patella and surrounding soft tissue for enhanced exposure of the knee joint when the femoral resurfacing guide is attached to the femur. Particularly, the patella is retracted and prevented from interfering with surgical preparation of the femur. The location and angle of the fixation pins in the eyelets provide secure fixation of the femoral resurfacing guide to the femur and adequate retraction of the patella and soft tissue, which is critical to good surgical exposure, particularly in a minimally invasive procedure.

Figure 44:
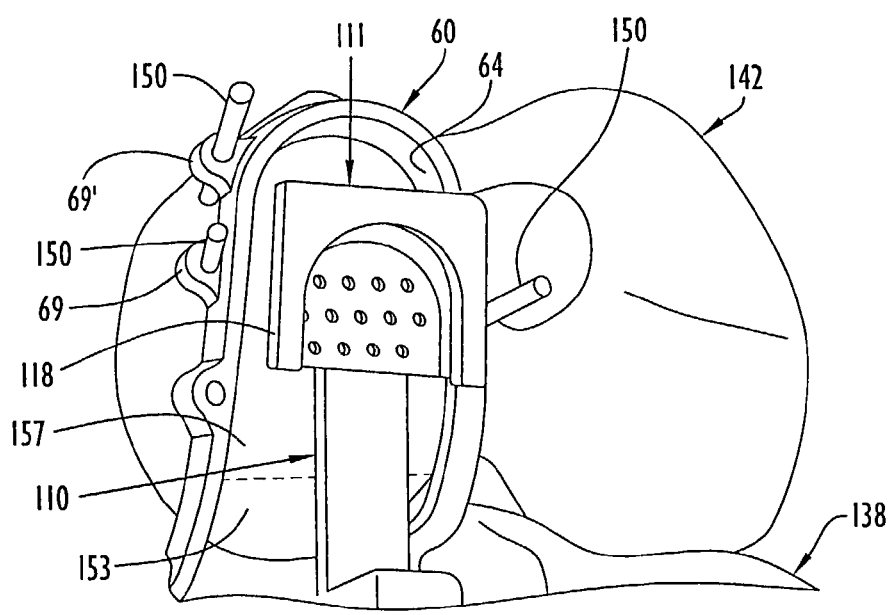
FIG. 44 is a broken perspective view depicting use of the femoral resurfacing instrument to prepare the distal aspect of the femur within a track of the femoral resurfacing guide.

A cutting member, such as cutting member C, is inserted through the resection slot 81 of the posterior resection block 70 to resect the posterior aspect of the femoral condyle along a plane parallel to the planar surface 144 of the tibia as shown in FIG. 43. Typically, a one half inch wide planar sagittal saw blade (0.050 inch/1.3 mm thick) powered by a powered handpiece or instrument is used as the cutting member inserted through the resection slot 81. The planar resection formed through the slot 81 will typically remove about 4–7 mm of bone, and more typically 7 mm of bone, from the most prominent point along the posterior aspect of the femoral condyle, resulting in a planar posterior resected surface 153 shown in FIG. 44. The rail member of femoral resurfacing guide 60 is angled in a medial-lateral direction from posterior to anterior relative to the plane of the resection slot 81 as may be best shown in FIG. 39B, but does not have to be angled as discussed above depending on the femoral component to be implanted. With the posterior resection complete, the fixation pin 151 is removed, and the posterior resection block 70 and linking instrument 100 are removed, leaving the femoral resurfacing guide 60 in place as shown in FIG. 44. The valgus rod 90 may be allowed to remain in the intramedullary canal to retract the patella and soft tissue or may be extracted from the intramedullary canal, with the sharp edges on the vanes of the valgus rod facilitating its extraction.

Figure 45A:
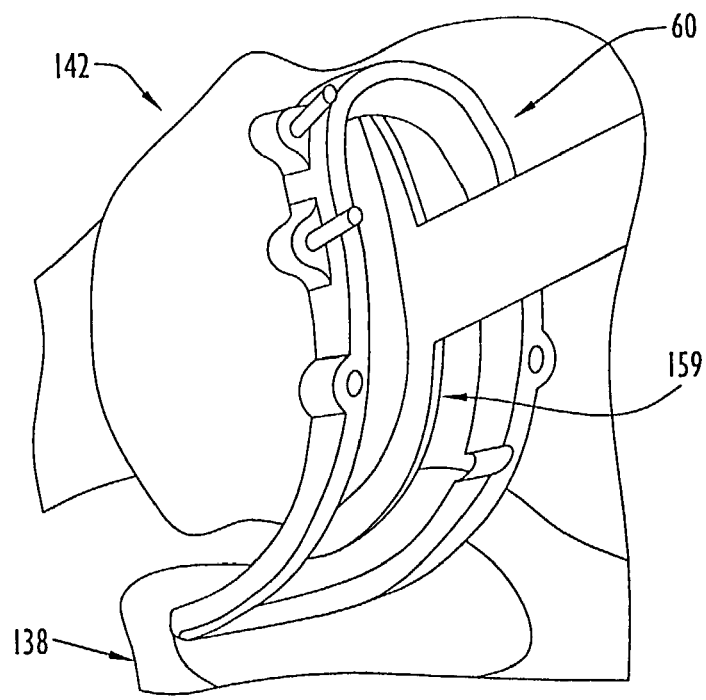
FIG. 45A is a broken perspective view depicting assessment of femoral component fit using a template.

To prepare the distal aspect of the femoral condyle for the femoral component, the appropriate size femoral resurfacing instrument 110 may be attached to a reciprocating powered handpiece or instrument, such as a power saw, via the adapter 112 to effect mechanical reciprocation of the tissue removing member 111. Of course, the tissue removing member can be manipulated manually via a manual handpiece or instrument to effect the necessary cartilage and/or bone removal. The tissue removing member 111 is placed within the area externally delineated by the inside surface 64 of the rail member, and the tissue removing surface of the tissue removing member is positioned against the most prominent surface of the femoral condyle delineated by the track. The handpiece is used to reciprocate the tissue removing member 111, and the tissue removing surface of the tissue removing member removes cartilage and/or articular bone in preparation for the femoral component. The tissue removing member is moved within the area delineated or outlined by the inside surface 64 of the rail member, with the U-shaped side wall of the tissue removing member serving as an abutment with the inside surface 64 of the femoral resurfacing guide 60. Also, the lower surface of ledge 118 maintained above or atop the anterior surface of the rail member as the tissue removing member is moved along the delineated area provides a stop to ensure that the articular surface of the femur is removed to a predetermined depth. The tissue removing member does not have to be maintained perpendicular to the femoral resurfacing guide to create the controlled depth resurfacing or tissue removal. FIG. 44 shows the femoral resurfacing instrument 110 directed along the delineated area in an upward direction; however, the femoral resurfacing instrument may be directed in a downward direction. In either case, the femoral resurfacing instrument must be directed in the upward direction to complete resurfacing of the femur at the most superior/anterior portion of the femoral resurfacing guide. The appropriate level of preparation is complete when the side wall of the tissue removing member 111 contacts the inside surface 64 of the rail member and when the lower surface of the ledge 118 contacts the front surface of the rail member along its entire path of travel along the delineated area to obtain a smooth, curved, resurfaced area or surface 157 on the distal aspect of the condyle. In cases of hard or sclerotic bone, it may be necessary to initially utilize a burr within the track of the rail member to remove the hard layer of bone prior to smoothing and finishing the femoral surface with the tissue removing member of the femoral resurfacing instrument. The bone surface may be checked and femoral component fit assessed using the trial femoral component 40 and/or an appropriate sized femoral shaping template 159 as shown in FIG. 45A to ensure a proper fit for the actual femoral component prior to removal of the femoral resurfacing guide. As shown in FIG. 45A, the template 159 has an inner surface with an anterior-posterior dimension corresponding to the anterior-posterior dimension of a prosthetic femoral component and a sagittal contour corresponding to the sagittal contour of the fixation surface of the prosthetic femoral component. The template 159 has an attached handle and is positionable on the prepared bone surface within the area delineated by the rail member of the femoral resurfacing guide 60.

During resurfacing, the area 157 is externally delineated or bounded medially, laterally and superiorly/anteriorly by the rail member of the femoral resurfacing guide and is bounded inferiorly/posteriorly by the previously prepared planar posterior resected surface 153. The resurfaced area 157 formed using the femoral resurfacing guide merges smoothly with the resected surface 153 and, during resurfacing, the femoral resurfacing guide properly and controllably guides the tissue removing member to obtain a smooth merger while preventing the tissue removing member from removing bone too far inferiorly/posteriorly. As a result of resurfacing, a layer of cartilage and/or bone is removed from the distal aspect of the femoral condyle to a controlled depth while essentially retaining the anatomic geometry of the distal aspect of the femoral condyle, as opposed to planar resections or cuts which substantially alter the anatomic geometry. Typically, about 2–4 mm of cartilage and/or bone is removed during resurfacing. The femoral condyle prepared in accordance with the present invention thusly has the prepared planar posterior resected surface or area 153 and the distal resurfaced area or surface 157 merging with and extending anteriorly from the resected surface 153. The resurfaced area matches a plurality of tangent radii of the fixation surface of the prosthetic femoral component in the sagittal plane and matches the angular sweep, i.e. 5 to 9 degrees, of the prosthetic femoral component in the coronal plane. Accordingly, the resurfaced area 157 extends anteriorly from the resected surface 153 at an angle in the medial-lateral direction corresponding to the anatomic angle of the femoral condyle. In the case of a medial femoral condyle, the resurfaced area 157 extends anteriorly from the resected surface 153 at a lateral angle. The resurfaced area thusly preserves the anatomic sweep of 5–9 degrees for the femoral condyle. The resected surface 153 and the resurfaced area 157 define a prepared surface for receiving the femoral fixation surface of the actual femoral component described in the co-pending patent application incorporated herein by reference, and the prepared surface follows the contour of the femoral fixation surface.

Figure 45B:
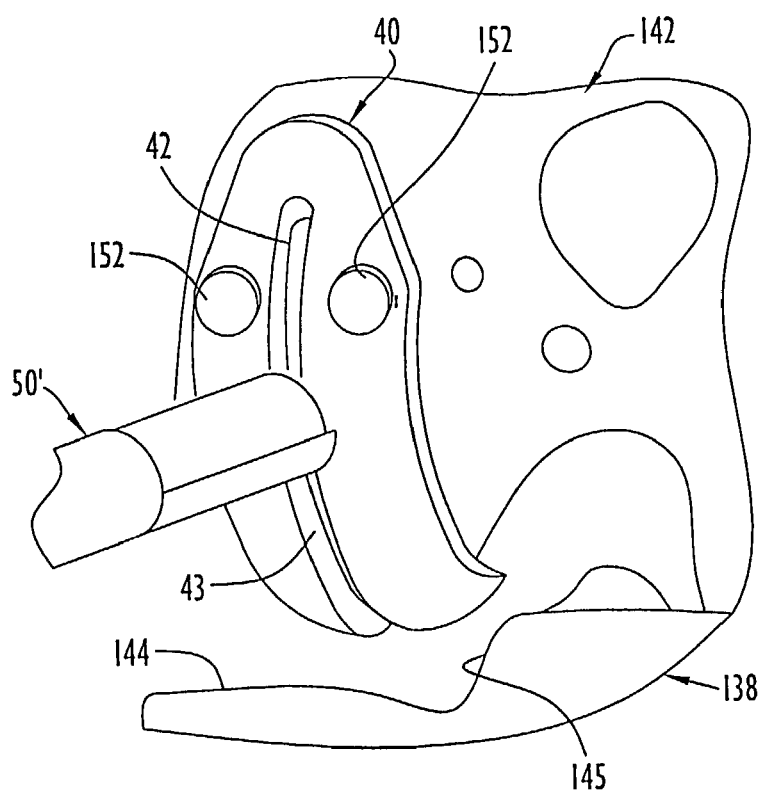
FIG. 45B is a broken perspective view of the trial femoral component positioned on the prepared femoral condyle and affixed to the femur.

After the femoral condyle has been properly resurfaced, the femoral resurfacing guide 60 is removed, and the appropriate size "left" trial femoral component for left knee implantation or the appropriate size "right" trial femoral component for right knee implantation is positioned on the prepared femoral surface as shown in FIG. 45B for "left" trial femoral component 40. It may be necessary to clean up the edges of the prepared femoral surface with a rongeur or hand rasp where the femoral resurfacing guide was seated to the bone. This will facilitate medial-lateral adjustment of the trial and prosthetic femoral components. With the handle 50' attached to the trial femoral component 40, the trial femoral component 40 is positioned flush against the flat resected surface 153 previously made on the posterior femoral condyle. Particularly, a planar rearward section of the trial femoral component fixation surface corresponding to the planar rearward section of the femoral fixation surface of the prosthetic femoral component is placed flush against the posterior resected surface 153. The trial femoral component is positioned to maximally cap the femoral condyle and to restore the normal tracking angle of the femoral condyle on the tibia without edge loading and edge contact. The handle 50' assists in evaluating the flexion/extension positioning and varus/valgus positioning. Correct medial-lateral placement of the trial femoral component is confirmed, and the trial femoral component 40 is pinned in place via fixation pins or other fixation elements 152 inserted in the anterior bore holes 44 of the trial femoral component. The handle 50' is removed or withdrawn from the trial femoral component once the trial femoral component has been fixated to the femur. Prior to pinning the trial femoral component, a trial tibial component may be positioned on the tibia as described below and a trial range of motion may be completed to ensure correct implant tracking. Trial range of motion may be performed subsequent to the trial femoral component being fixated to the femur, since the heads of the fixation elements 152 are recessed in the bore holes 44 and do not protrude beyond or interfere with the outer surface of the trial femoral component. The trial tibial component can be moved, as needed, to ensure correct implant tracking prior to preparing the femur for the fixation peg and fin of the actual femoral component. Correct implant tracking is confirmed by ensuring that the tracking pattern of the trial femoral and tibial components in flexion and extension follows the normal tibiofemoral tracking pattern.

Figure 46A:
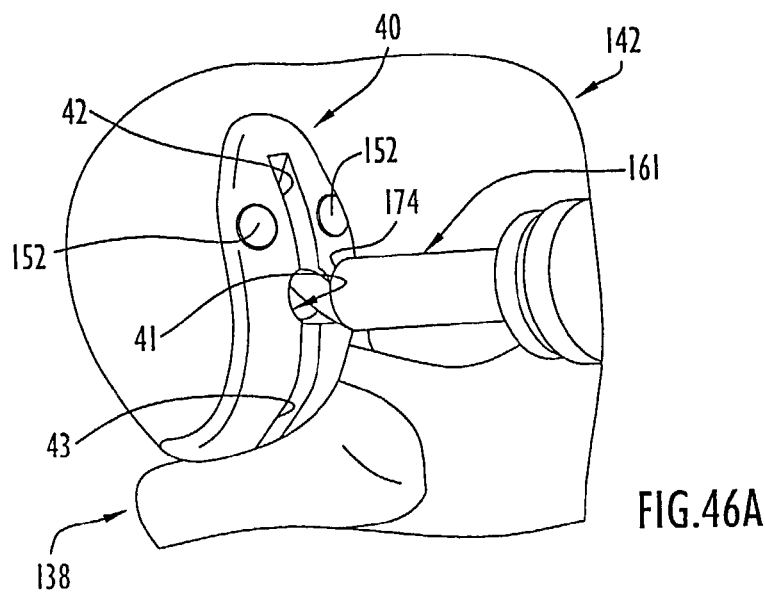
FIG. 46A is a broken perspective view showing preparation of the femur for the femoral fixation peg of the femoral component.
Figure 46B:
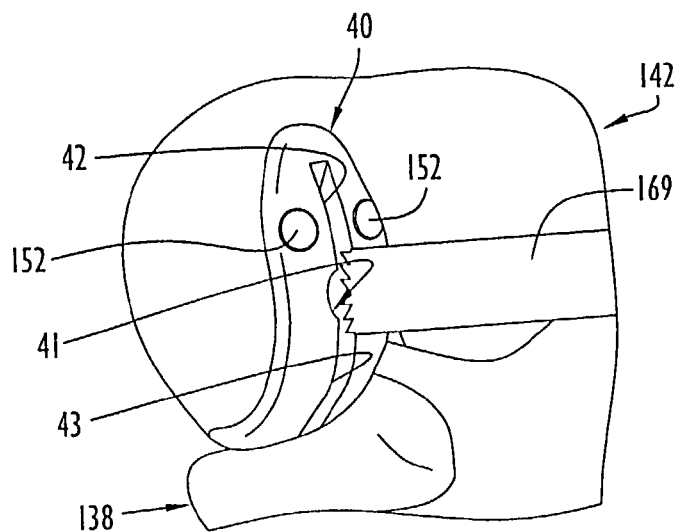
FIG. 46B is a broken perspective view depicting initial preparation of the femur for the femoral fixation fin of the femoral component.
Figure 46C:
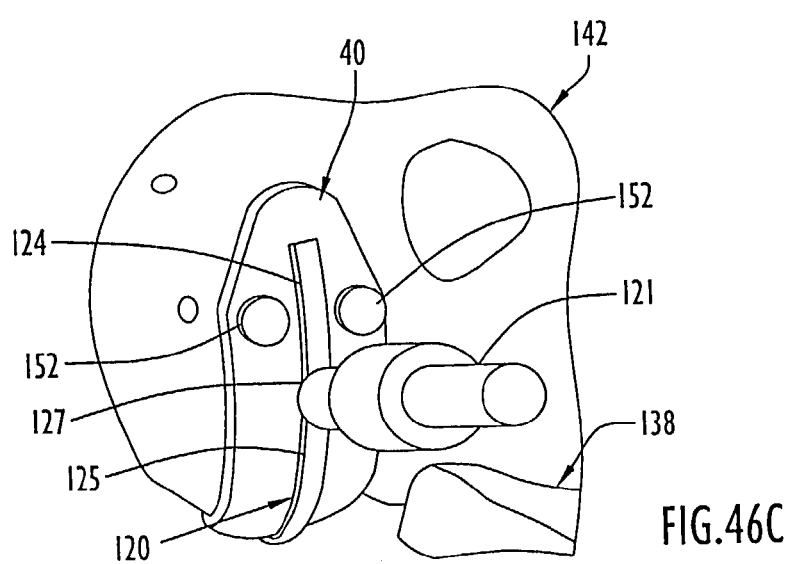
FIG. 46C is a broken perspective view showing use of the femoral fin punch to complete preparation of the femur for the femoral fixation fin.

Preparation of the femur to accommodate the femoral fixation peg of the actual femoral component is effected using a femoral peg drill or cutting member 161 of appropriate size inserted in the bore hole 41 of the trial femoral component 40 as shown in FIG. 46A. The cutting member 161 should be positioned perpendicular to the femoral surface and penetrated, drilled or reamed into the bone until a depth stop 174 on the cutting member 161 contacts the trial femoral component to limit or control penetration of the cutting member 161 to the proper depth. The femoral peg cutting member 161 can be made available in different sizes or size ranges to accommodate different sizes of prosthetic femoral fixation pegs associated with the different sizes of femoral components. Once the femoral peg hole has been formed for the femoral fixation peg, preparation for the femoral fixation fin is initiated using a cutter 169 inserted through the slot formed by slot segments 42 and 43 and by the hole 41 in the trial femoral component 40 as shown in FIG. 46B. Preferably, the cutter 169 is a planar oscillating or podiatry saw. Care should be taken not to over-resect bone in the central portion of the femur. Preparation of the femur for the femoral fixation fin is completed using the femoral fin punch 120 as shown in FIG. 46C. The anterior and posterior fin elements 124 and 125 of the punch member are placed within the anterior and posterior slot segments 42 and 43, respectively, of the trial femoral component 40, with the peg element of the punch member seated in the hole previously drilled in the femur for the peg of the actual femoral component. The handle 121 of the femoral fin punch is lightly tapped until the depth stop formed by the anterior and posterior edge surfaces 29,29' of the femoral fin punch abut the end surfaces 45,46 of the trial femoral component in the fully inserted position for the fin punch, the fin elements 124 and 125 forming slots in the femur for receiving the anterior and posterior femoral fixation fin segments of the actual femoral component. With preparation of the femur for the fin of the prosthetic femoral component thusly completed, the femoral fin punch 120 is removed.

Figure 47:
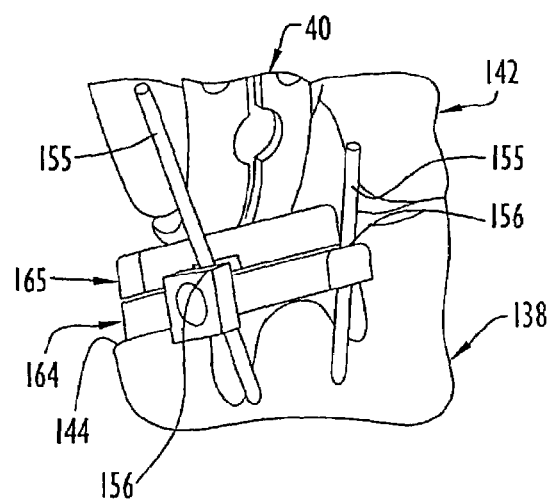
FIG. 47 is a broken perspective view showing a trial tibial component fixated on the prepared tibial plateau.

Placement and sizing for the actual or prosthetic tibial component may be determined using one of two methods. In a first method, the tibial component size that maximizes tibial coverage is determined, and a corresponding trial base 164 of a trial tibial component is aligned with the medial third of the tibial tubercle as shown in FIG. 47. The trial base 164 is oriented with its planar side wall adjacent the sagittal resected surface and its arcuate side wall at the medial border of the tibial plateau without excess overhang. The trial base 164 is pinned in place on the planar resected surface 144 using fixation pins or elements 155 inserted through anterior eyelets 156 of the trial base. Typically, 0.125 inch (3.2 mm) headless fixation pins will be used as the fixation elements 155. An appropriate size trial insert 165 of the trial tibial component is attached to the trial base 164 as shown in FIG. 47, and the knee is run through a range of motion to confirm correct implant tracking and trial component positioning. If necessary, trial tibial component size and/or positioning is/are adjusted. In a second method represented by FIG. 48, the tibial component size that maximizes tibial coverage is determined, and the appropriate medial-lateral and rotational alignment is confirmed by placing the knee through a range of motion with a free-floating trial tibial component having a trial base 164' and trial insert 165'. A line 147 is etched in the center of the trial insert 165' to facilitate assessment of proper tibiofemoral tracking, and the free-floating trial tibial component can be moved and positioned to maximize contact with the trial femoral component without "overstuffing" the knee joint. Once proper tracking is confirmed, the trial base 164' is pinned in place using fixation elements through anterior eyelets 156' as described above for trial base 164.

The trial tibial components can be one-piece monolithic components or multi-piece modular components. In modular trial tibial components, the trial inserts can be assembled to the trial bases in the same manner as described in the co-pending patent application incorporated herein by reference for assembly of the actual tibial component inserts on the actual tibial component bases. Accordingly, the trial inserts and trial bases can be provided with cooperable lip and shoulder formations as disclosed in the referenced patent application.

Figure 49:
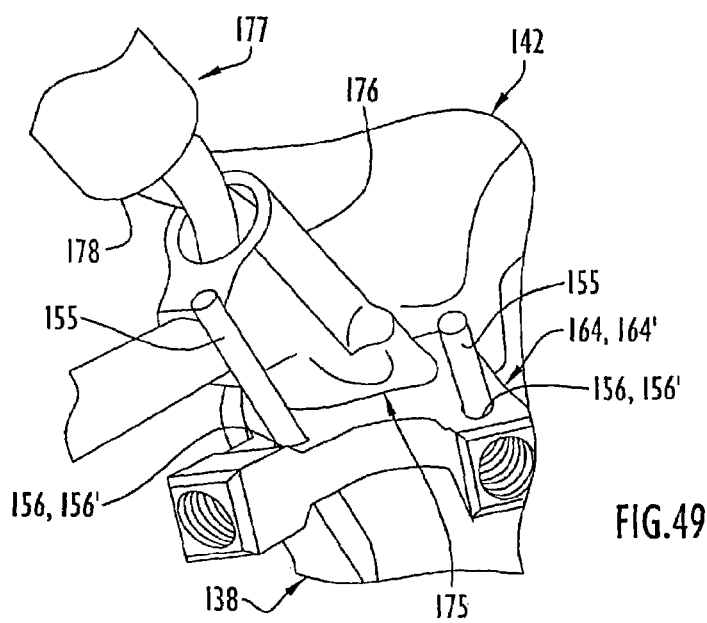
FIG. 49 is a broken perspective view illustrating preparation of the tibia for the posterior tibial fixation peg of the actual tibial component.

Preparation of the tibia for the posterior tibial fixation peg of the actual tibial component is represented in FIG. 49 and involves removing the trial femoral component 40 from the femur and removing the trial insert 165,165' from the trial base 164,164'. With the trial base 164, 164' in position on the planar resected surface of the tibial plateau, a tibial peg cutting member guide or drill guide having a handle attached thereto is applied to the trial base 164,164' so that an angled sleeve 176 of the guide 175 is aligned in communication with a posterior bore hole of the trial base 164,164'. The posterior bore hole of trial base 164,164' corresponds in location to the posterior tibial fixation peg of the actual tibial component. The sleeve 176 of the guide 175 extends angularly from the posterior bore hole toward the anterior and, if necessary, the tibia 138 can be maximally flexed and externally rotated to facilitate placement of the guide. The guide 175 is releasably or removably secured to the trial base 164,164' by engaging at least one pin on the undersurface of the guide into at least one angled hole in the trial base 164,164'. Preferably, two pins are provided on the guide 175 for engaging two angled holes, respectively, in the trial base 164,164'. With the trial base 164,164' pinned in place, a tibial peg cutting member, drill or reamer 177 is inserted through the sleeve 176 and into the posterior bore hole in the trial base 164,164'. The tibial peg cutting member 177 is advanced through the posterior bore hole to form a posterior peg hole in the tibia for the posterior tibial fixation peg, and a depth stop 178 on the tibial peg cutting member engages the sleeve 176 to ensure penetration of the cutting member 177 to the proper depth. The sleeve 176 is angled relative to the planar resected surface of the tibial plateau, and is preferably at a 50° angle to the resected tibial surface, to optimally facilitate preparation of the posterior peg hole.

Figure 50:
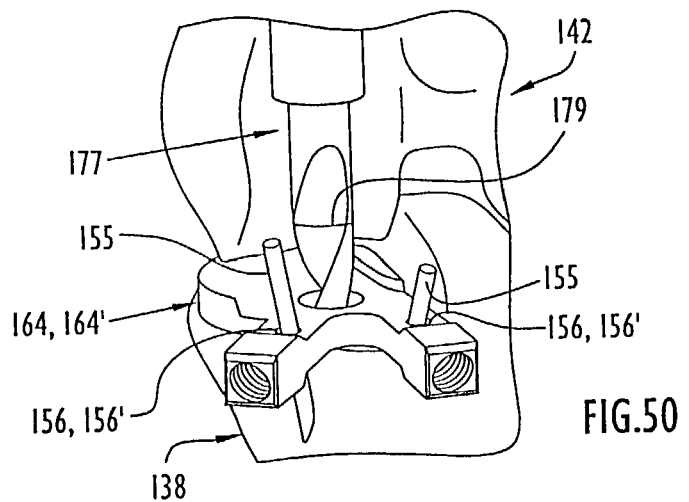
FIG. 50 is a broken perspective view depicting preparation of the tibia for the anterior tibial fixation peg of the actual tibial component.

Preparation of the tibia for the anterior tibial fixation peg is represented in FIG. 50. The tibial peg cutting member 177 is removed from the sleeve 176 upon completion of the posterior peg hole and the guide 175 is removed from the trial base 164,164'. The femur 142 is kept flexed with the tibia externally rotated. The tibial peg cutting member 177 is inserted in an anterior bore hole located in tibial base 164,164' at a location corresponding to the anterior tibial fixation peg of the actual tibial component. The tibial peg cutting member 177 is advanced through the anterior bore hole to form an anterior peg hole in the tibia to receive the anterior tibial fixation peg. The tibia is penetrated, drilled or reamed to a depth stop 179 on the tibial peg cutting member, thereby limiting or controlling penetration to the required depth. The depth stop 179 may include indicia, such as a line or marking on the cutting member 177 and, as an example, penetration of the cutting member 177 to the proper depth can be associated with alignment of the indicia 179 with an upper surface of the trial base 164,164'. The fixation elements 155 are removed from the eyelets 156,156' of the trial base 164,164' and the trial base is removed from the tibia.

Figure 51:
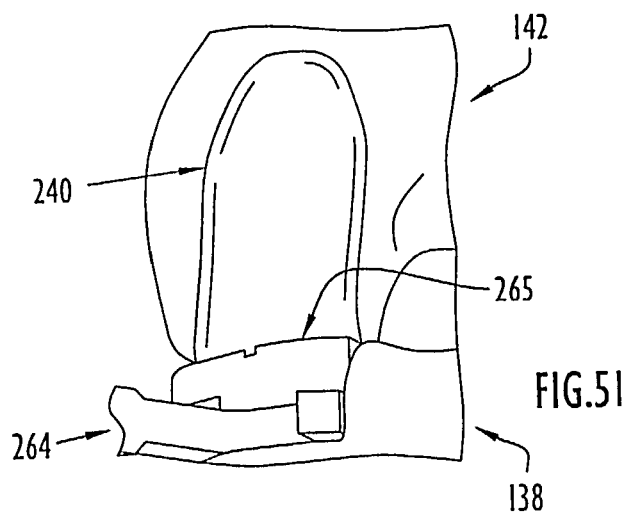
FIG. 51 is a broken perspective view showing pegged trial components placed on the prepared femoral condyle and prepared tibial plateau.

Final trial reduction may be performed using pegged trial components as depicted in FIG. 51. An appropriate size monolithic trial tibial component or a modular trial tibial component having a trial insert 265 assembled on a pegged trial base 264 is positioned on the prepared tibial plateau with anterior and posterior tibial fixation pegs of the trial base received in the anterior and posterior peg holes previously formed in the tibia 138. Component size, tracking and ease of insertion are confirmed. If difficulty is encountered during placement of the pegged trial tibial component, it may be necessary to chamfer the posterior peg hole with a round burr or other suitable instrument. A monolithic femoral trial component 240 is positioned on the prepared femoral condyle with its femoral fixation peg received in the previously formed femoral peg hole. Standard range of motion and stability testing are performed to confirm final implant alignment and to determine the appropriate thickness for the actual tibial component. Of course, final reduction could be performed using the actual tibial component and/or femoral component prior to cementitious fixation thereof. Once the femoral and tibial component sizes have been finally confirmed, all trial components are removed and the femoral and tibial surfaces are prepared for cement application. Multiple holes may be formed in the prepared surfaces of the femur and tibia, typically utilizing a 0.125 inch (3.2 mm) drill bit, for enhanced cement penetration. Both the femur and the tibia are thoroughly pulse ravaged and dried prior to cement application.

Figure 52:
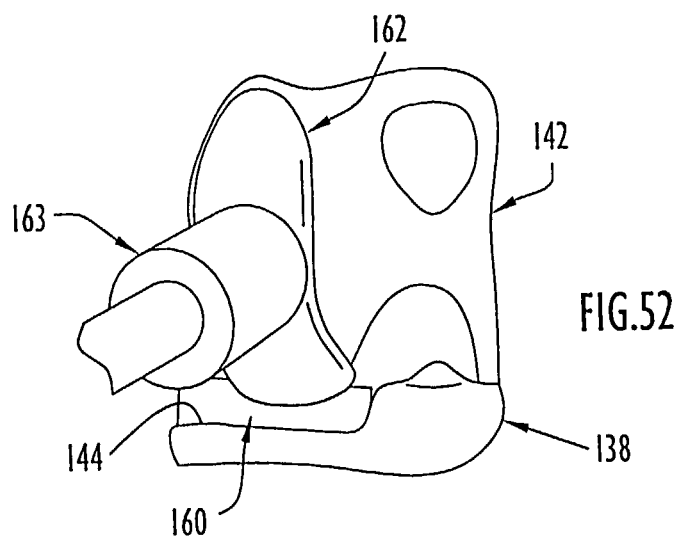
FIG. 52 is a broken perspective view depicting implantation of the actual femoral component and the actual one-piece tibial component on the prepared surfaces of the femoral condyle and tibial plateau, respectively.

Prior to final implantation of the prosthetic tibial component, a dry sterile twisted gauze is applied along the posterior border of the tibia. In order to cement the actual one-piece prosthetic tibial component 160, shown in FIG. 52, to the prepared surface of the tibia 138, cement is applied to the tibial fixation surface to fill the cement pocket. The tibial component 160 is then positioned on the planar surface 144 in the position previously established using the trial tibial component. The anterior and posterior tibial fixation pegs of the actual tibial component are aligned with and inserted in the previously prepared anterior and posterior peg holes in the tibia. The continuously planar peripheral rim of the tibial fixation surface is continuously supported on the planar surface 144 without penetrating the bone. The dovetail surrounding the cement pocket captures cement in the cement pocket. Excess cement is removed once the tibial component 160 is in place.

The prosthetic femoral component 162 is implanted by applying cement to the femoral fixation surface, thereby filling the cement pocket. The femoral component 162 is positioned on the prepared femoral surface in the position previously established using the trial femoral component. The fixation peg and fin of the actual femoral component are aligned and inserted in the corresponding peg hole and slot previously formed in the femur. A femoral component impactor 163 may be used to fully seat the femoral component 162. The planar rearward section of the femoral fixation surface is disposed in mating relation on the planar posterior surface 153, and the curved intermediate section and planar forward section of the femoral fixation surface are disposed in mating relation on the distal resurfaced area 157, the resurfaced area including a curved portion corresponding to the curved intermediate section and a planar portion corresponding to the planar forward section. All excess cement is removed. The implanted tibial and femoral components are irrigated thoroughly, and routine incision closure is performed.

Figure 48:
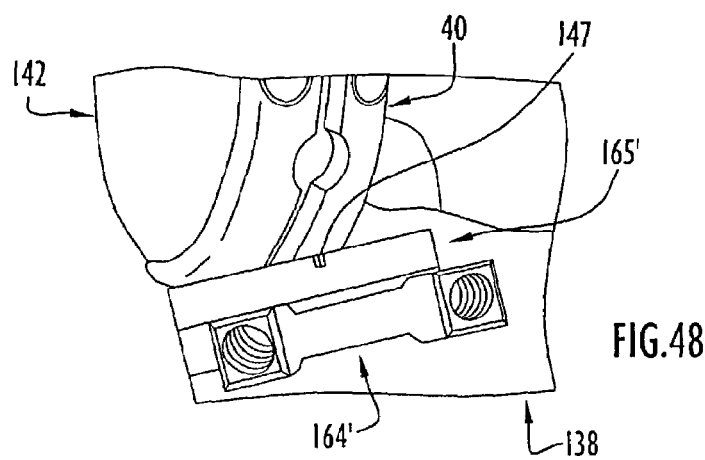
FIG. 48 is a broken perspective view depicting a floating trial tibial component positioned on the prepared tibial plateau.

Implantation of a modular tibial component as disclosed in the prior application incorporated herein by reference is similar to implantation of the one-piece tibial component except that a trial tibial component base 164,164' and a trial tibial component insert 165,165' are used to determine placement and size of the actual modular tibial component as shown in FIGS. 47 and 48. The selected size trial tibial component base 164,164' is pinned to the tibia, with a selected size tibial insert 165,165' being attached to the trial tibial component base. The knee is run through a range of motion to confirm desired implant tracking and component positioning, and the sizes of the trial base and/or the insert are adjusted as needed. In order to prepare the tibia for the fixation pegs of the actual base, a drill is inserted through pre-formed holes in the trial base component 164,164' corresponding to the pegs of the actual tibial component.

Figure 54:
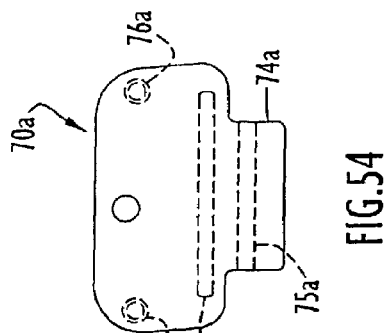
FIG. 54 is a front view of an alternative posterior resection block.
Figure 53:
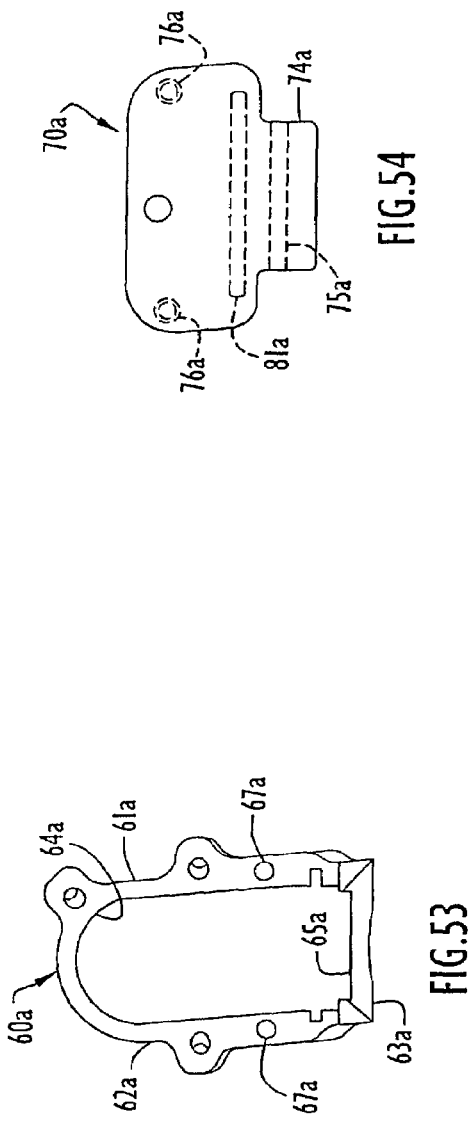
FIG. 53 is a front view of an alternative femoral resurfacing guide.

An alternative femoral resurfacing guide 60a is shown in FIG. 53, and an alternative posterior resection block 70a is shown in FIG. 54. Femoral resurfacing guide 60a is similar to femoral resurfacing guide 60 except that the medial and lateral legs 61a and 62a of femoral resurfacing guide 60a are angled five degrees from vertical. The femoral resurfacing guide 60a has through holes 67a for receiving the alignment posts of a posterior resection block and has a recessed surface 65a for supporting the tongue of the posterior resection block. The femoral resurfacing guide 60a has an inside surface 64a forming a track for a femoral resurfacing instrument. The posterior resection block 70a is similar to posterior resection block 70 except that opposing side walls of posterior resection block 70a are angled five degrees from the vertical. Posterior resection block 70a has attachment posts 76a, tongue 75a and a resection slot 81a for performing a planar resection.

Figure 55:
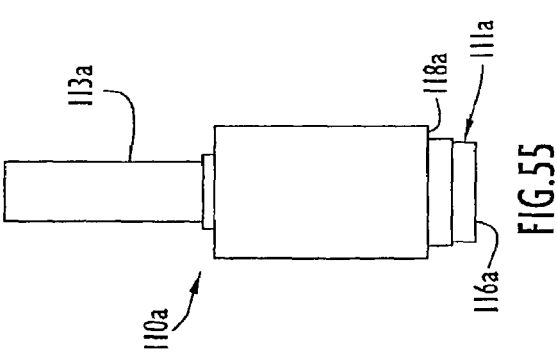
FIG. 55 is a side view of an alternative femoral resurfacing instrument.

An alternative femoral resurfacing instrument 110a for use with the femoral resurfacing guides of the present invention is shown in FIG. 55 and is an end mill cutter for resurfacing a femoral condyle within the inside surface of a femoral resurfacing guide. The end mill cutter includes a proximal shaft 113a for connection with a powered handpiece, and a tissue removing member 111a having a tissue removing or cutting surface 116a mechanically driven by the powered handpiece. Typically, the tissue removing or cutting surface will be rotatably driven by the powered handpiece. The tissue removing surface 116a can have any suitable tissue removing or cutting edges.

Figure 56:
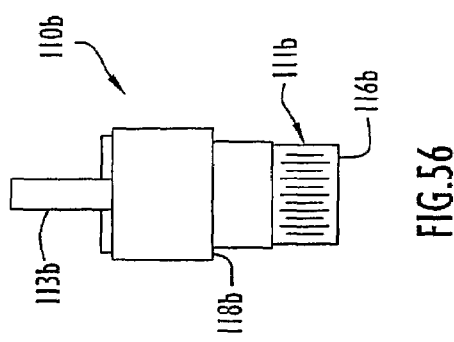
FIG. 56 is a side view of another alternative femoral resurfacing instrument.

FIG. 56 illustrates another alternative femoral resurfacing instrument 110b in the form of a reamer for use with a femoral resurfacing guide. The reamer includes a proximal shaft 113b for connection with a powered handpiece and a tissue removing member 111b with a distal tissue removing surface 116b driven, typically rotatably, by the powered handpiece. The tissue removing surface 116b can have any suitable tissue removing or cutting edges. The end mill cutter 110a and the reamer 110b have ledges 118a and 118b, respectively, forming a stop with the abutment walls of the femoral resurfacing guides to control the depth of resurfacing of a femoral condyle.

Figure 57:
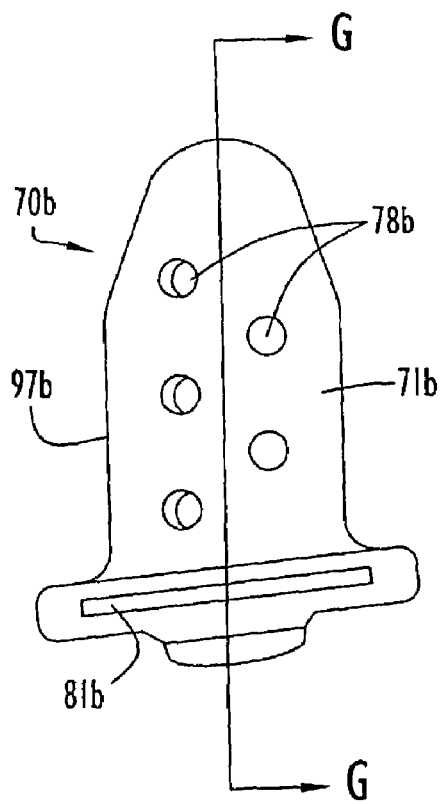
FIG. 57 is a front view of a further alternative posterior resection block according to the present invention.
Figure 58:
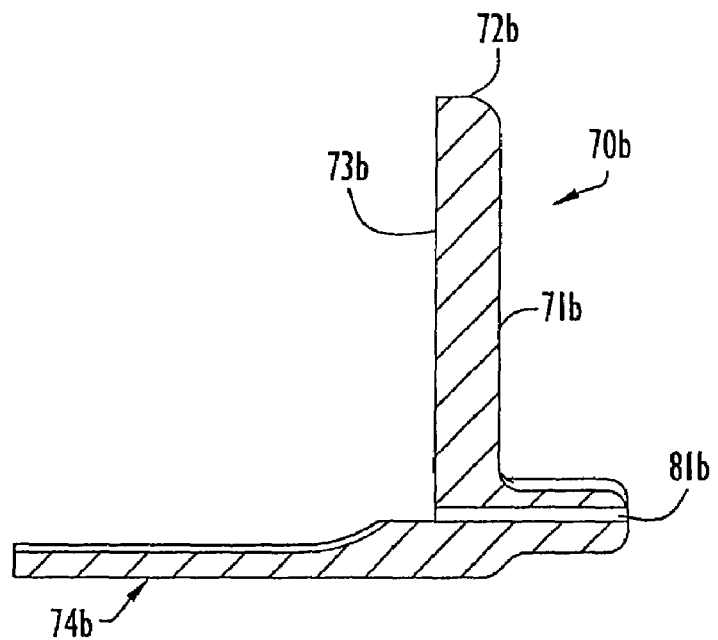
FIG. 58 is a side sectional view taken along line G—G of FIG. 57.

A further alternative posterior resection block 70b is depicted in FIGS. 57 and 58. The posterior resection block 70b includes a housing having an anterior or forward portion defined by a front surface 71b, a top surface 72b and a back surface 73b, and a base plate 74b extending from the anterior portion. The base plate 74b extends both forwardly and rearwardly from the anterior portion as best shown in FIG. 58. A resection slot 81b extends through the anterior portion of the housing from a forward or anterior end of the base plate 74b to the back surface 73b to receive a cutting member as described above for posterior resection block 70. The anterior portion of posterior resection block 70b has a peripheral edge or border 97b defining a configuration and size corresponding to the configuration and size of at least a distal portion of a prosthetic femoral component. Accordingly, the peripheral or perimetrical configuration of the anterior portion of resection block 70b corresponds to the medial-lateral and anterior-posterior configuration and size of at least part of the distal portion of the prosthetic femoral component. The posterior resection block 70b can be made available in different sizes corresponding to different sizes of femoral components and permits the surgeon to judge femoral component sizing and fit prior to forming the planar resection along the posterior aspect of the femoral condyle. One or more fixation holes 78b are formed through the anterior portion of resection block 70b for receiving fixation elements for fixating the resection block 70b to the femur as discussed above for resection block 70. Resection block 70b is utilized independently of a resurfacing guide in a two-step procedure in which the resection block 70b is first fixated to the femur and a cutting member is inserted through the resection slot 81b to form the planar resected surface along the posterior aspect of a femoral condyle as described above for resection block 70. When the resection block 70b is positioned on the femoral condyle prior to establishing the planar surface along the posterior aspect thereof, the anterior portion of resection block 70b provides an indication of prosthetic femoral component sizing and fit. The bottom surface of base plate 74b is planar and parallel to the resection slot 81b so that the resection slot is parallel to a planar resected surface of the tibial plateau when the bottom surface is placed thereon. After the resected surface is formed along the posterior aspect of the femoral condyle using a cutting member inserted through the resection slot 81b, the resection block 70b is removed from the femur and a resurfacing guide is thereafter attached to the femur to resurface the distal aspect of the femoral condyle as described above. The anterior portion of the resection block 70b is angled in the medial-lateral direction relative to the resection slot 81b to correspond to the angular sweep of the prosthetic femoral component disclosed in the applications incorporated herein by reference. It should be appreciated, however, that where the femoral component does not have an angular sweep, the central longitudinal axis of the anterior portion of the resection block 70b can be perpendicular to the resection slot 81b.

Figure 59:
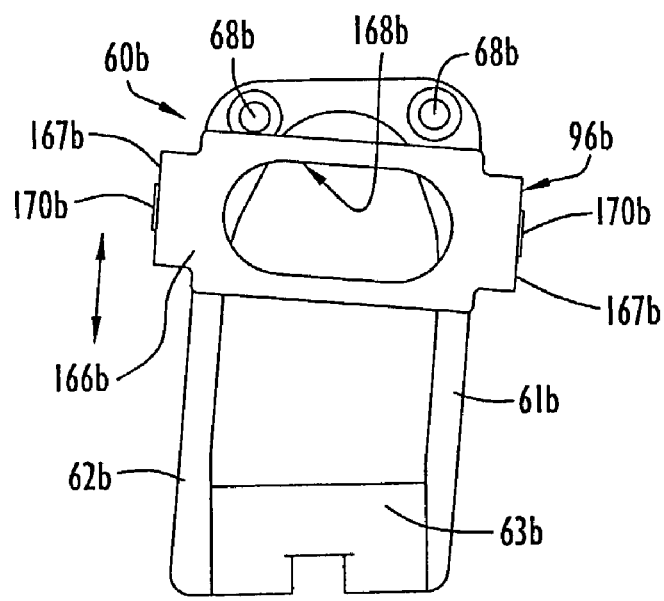
FIG. 59 is a front view of another alternative femoral resurfacing guide.
Figure 60:
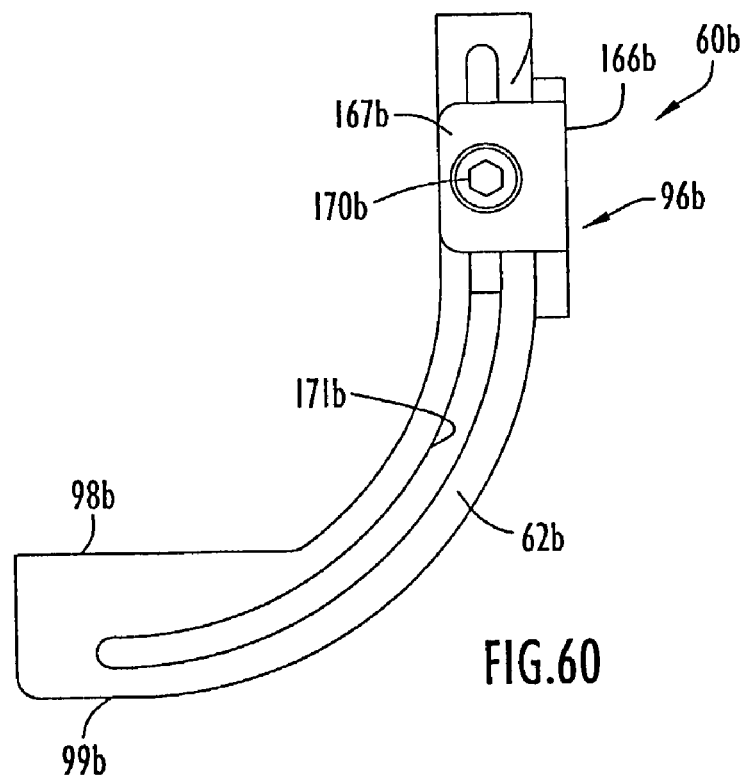
FIG. 60 is a side view of the femoral resurfacing guide of FIG. 59.

FIGS. 59 and 60 illustrate another alternative femoral resurfacing guide 60b, which is representative of a femoral resurfacing guide in which the medial and lateral legs of the rail member have slots therein for movement of a slide 96b along the rail member. The rail member for femoral resurfacing guide 60b delineates an area of a femoral condyle to be resurfaced and includes legs 61b and 62b having posterior ends connected by a transverse connecting pad 63b. The area delineated by the rail member of femoral resurfacing guide 60b is similar to the area delineated by the rail member of femoral resurfacing guide 60 except that the delineated area for femoral resurfacing guide 60b is more steeply tapered at the top of the rail member to correspond to the configuration of a prosthetic femoral component. Also, the femoral resurfacing guide 60b has a pair of fixation holes 68b located at the top of the rail member. The posterior portion of the rail member is adapted for positioning between a planar resected surface prepared along a tibial plateau and a posterior planar surface prepared along the posterior aspect of a corresponding femoral condyle, with the posterior portion of the rail member being of sufficient thickness and having top and bottom parallel planar surfaces 98b and 99b, respectively, to abut with the previously prepared femoral and tibial surfaces. Of course, the rail member can be provided with a stylus as described above for femoral resurfacing guide 60. The slide 96b comprises a front face 166b disposed over the front surface of the rail member and side flanges 167b angled rearwardly therefrom such that the legs 61b and 62b are disposed between the side flanges. The front face 166b extends across the delineated area in the medial-lateral direction, and a window 168b in the front face provides access to the delineated area. The slide 96b is slidable along the rail member in the anterior-posterior direction via connector elements 170b extending through side flanges 167b and through slots 171b in legs 61b and 62b. Connector elements 170b move within the slots 171b as the slide is moved along the rail member while serving to secure the slide on the rail member. The femoral resurfacing guide 60b is used to resurface a femoral condyle in a manner similar to that described above for femoral resurfacing guide 60, except that a tissue removing member is inserted through the window 168b to contact the femoral condyle for removal of anatomical tissue therefrom. Movement of the tissue removing member along the delineated area in the anterior-posterior direction causes the slide to move anteriorly-posteriorly therewith relative to and along the rail member as shown by an arrow in FIG. 59. Depending on the size of the tissue removing member, the tissue removing member may also be moved relative to and within the window. The front surface of the front face of the slide forms an abutment wall engageable with a ledge of the tissue removing instrument to control the depth of resurfacing as described above. The femoral resurfacing guide 60b is particularly well adapted for use with a high speed burr as the tissue removing instrument.

Figure 61:
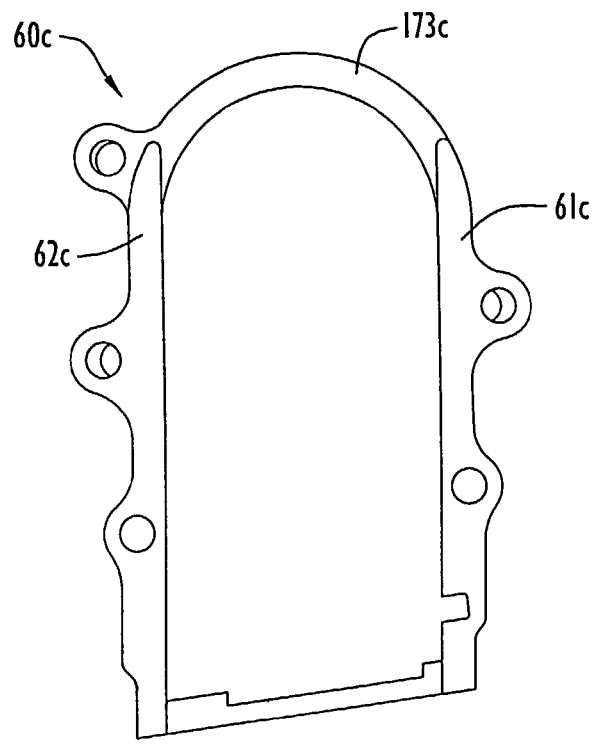
FIG. 61 is a front view of yet another alternative femoral resurfacing guide.
Figure 62:
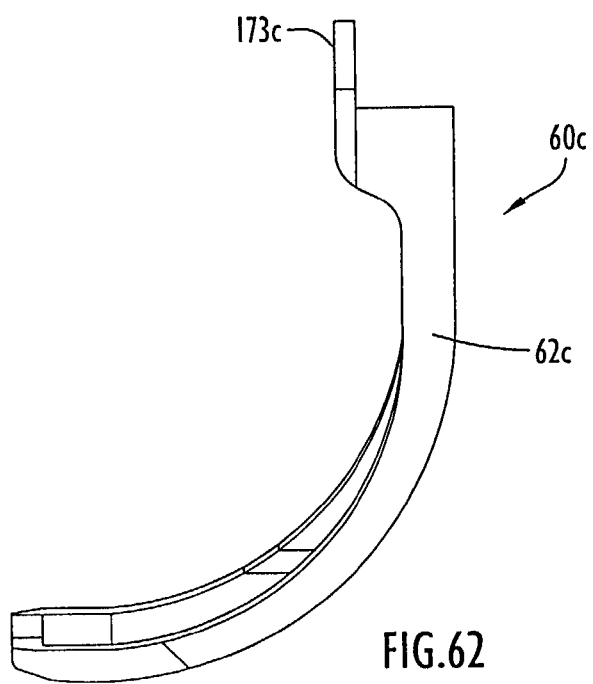
FIG. 62 is a side view of the femoral resurfacing guide of FIG. 61.
Figure 63:
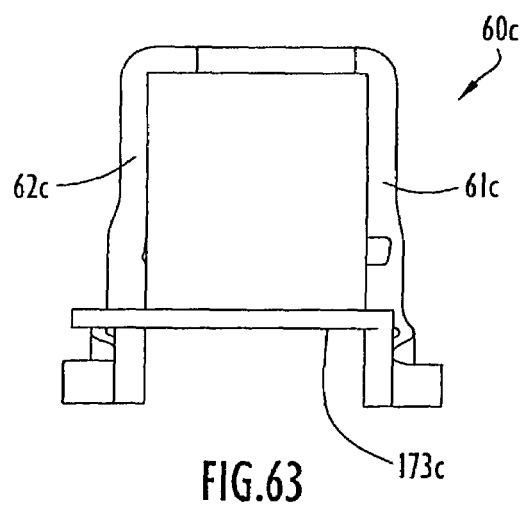
FIG. 63 is a top view of the femoral resurfacing guide of FIG. 61.

An additional alternative femoral resurfacing guide 60c is depicted in FIGS. 61–63. The femoral resurfacing guide 60c is similar to femoral resurfacing guide 60 except that the top of the rail member for femoral resurfacing guide 60c is formed by a cross member 173c that is recessed from or spaced behind the front surfaces of the legs 61c and 62c as best shown in FIGS. 62 and 63. The cross member also serves as a stylus similar to the stylus 59. When the femoral resurfacing guide 60c is affixed to a femoral condyle to effect resurfacing, the cross member 173c is located on the femoral condyle further anteriorly than the top of the rail member for femoral resurfacing guide 60. The cross member 173c is disposed close to the surface of the femoral condyle at, near or beyond where the distal aspect of the femoral condyle begins to curve toward the anterior aspect of the femoral condyle. A tissue removing member used to resurface the femoral condyle can be moved anteriorly beyond the area of the femoral condyle delineated by the rail member of femoral resurfacing guide 60c since the tissue removing member can be moved over the cross member 173c out to where the femoral condyle curves away toward the anterior aspect thereof.

Figure 64:
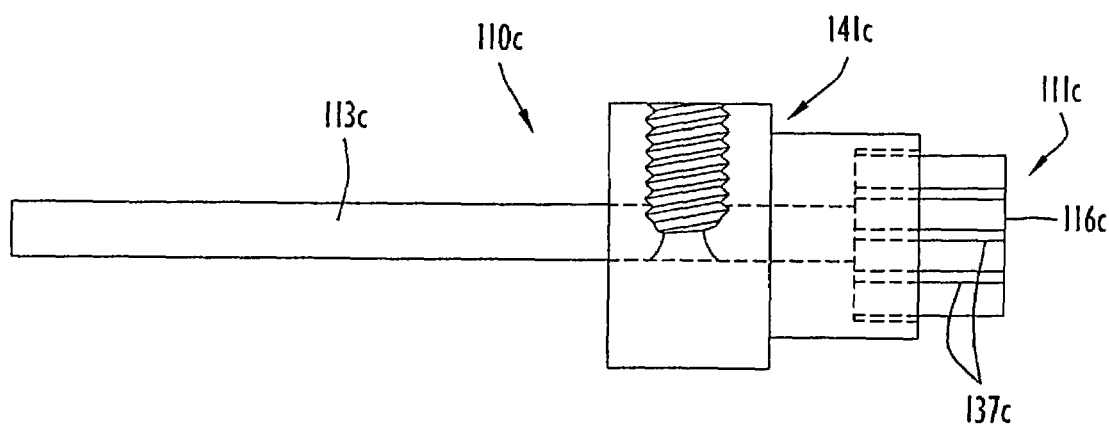
FIG. 64 is a side view of yet another femoral resurfacing instrument.

FIG. 64 depicts another alternative femoral resurfacing instrument 110c for use with a femoral resurfacing guide. The instrument 110c is in the form of a burr and particularly a burr designed to be rotated at relatively high speeds by a powered handpiece. The tissue removing instrument 110c comprises a tissue removing member 111c mounted at the end of a shaft 113c for being coupled to a powered handpiece. The tissue removing member 111c is substantially cylindrical in configuration with a plurality of flutes forming cutting edges 137c therealong. The cutting edges 137c extend along the end face 116c of the tissue removing member, the end face 116c defining a tissue removing surface for the tissue removing member. The tissue removing member 111c is assembled to a fixture 141c of the femoral resurfacing instrument 110c, and the shaft 113c is held in place in a passage of the fixture via a set screw. The tissue removing member 111c is partially disposed in a recess of the fixture such that the fixture forms a ledge 118c cooperable with an abutment wall of a femoral resurfacing guide to limit the depth of resurfacing as described above. Although the instrument 110c is depicted as a two-part assembly, it should be appreciated that the burr can be provided without the fixture and can be a single member or part with the ledge integrally, unitarily formed therewith.

It should be appreciated that the area delineated by the rail members can be one continuous, unbroken delineated area or may comprise a plurality of individual delineated area segments as represented in dotted lines in FIG. 13. Using a rail member that delineates one continuous unbroken area has the advantage of simplifying procedural steps, thereby reducing the time and cost of surgery. The dotted lines in FIG. 13 illustrate the femoral resurfacing guide 60 with a divider 127 extending anteriorly-posteriorly from the top of the rail member to the connecting pad 63. The divider 127, which may be formed integrally, unitarily with the rail member, is centered between the legs 61 and 62 but can be disposed at any suitable location. Also, the divider 127 follows the anterior-posterior contour of the legs 61 and 62. The area delineated by the rail member having divider 127 comprises two delineated area segments, one on each side of the divider. The rail member thusly defines two tracks 64' on each side of divider 127 externally delineating the delineated area segments. In order to resurface a femoral condyle, a tissue removing member having a size to fit within the delineated area segments is moved along the surface of the femoral condyle as described above, except that the tissue removing member is moved with the track of each delineated area segment to resurface the femoral condyle along each delineated area segment. The front surface of the divider 127 cooperates with a ledge of the tissue removing instrument to form a stop for controlling the depth of resurfacing as described above for the rail members not having a divider. As a result of resurfacing, two resurfaced area segments are formed along the femoral condyle separated by an unfinished segment of the femoral condyle beneath the divider 127. After the delineated area segments have been resurfaced and the femoral resurfacing guide has been removed from the femoral condyle, the unfinished segment of the femoral condyle previously covered by the divider is resurfaced to the depth of the resurfaced area segments using a tissue removing member, the previously formed resurfaced area segments serving as a guide to control the depth of resurfacing for the unfinished segment of the femoral condyle. The rail member can be provided with any number of dividers of various configurations such that the rail member can externally delineate any number of delineated area segments of various shapes and sizes.

The dotted lines in FIG. 13 are also representative of a femoral resurfacing guide in which the fixation holes or eyelets may be located within the delineated area. In the solid line view of FIG. 13, the eyelets 68, 69 and 69' are located along the legs of the rail member outside the area that is externally delineated by the rail member. In the dotted line view, eyelets 68 defining fixation holes are located along the divider 127 and are thusly within the area that is externally delineated by the rail member. Where the fixation holes are provided within the externally delineated area, the fixation holes located outside the delineated area may be eliminated.

With the present invention, femoral preparation is accomplished with minimally invasive instrumentation through a small incision without everting the patella. A minimal amount of bone is removed from a single femoral condyle that results in a plurality of tangential radii that match the geometry of the fixation surface of the prosthetic femoral component. Various instruments may be used as the femoral resurfacing instruments, including rasps, end mill cutters, reamers and burrs, to remove bone through a femoral resurfacing guide that matches the femoral component's sagittal geometry. The area from which bone is removed may be matched with the angular sweep of the prosthetic femoral component. The posterior resection block attaches and references from the femoral resurfacing guide without removing the femoral resurfacing guide. Femoral instrumentation also allows for anatomic extramedullary and intramedullary axis references. The femoral resurfacing instruments are controlled through a captured rail member that follows the configuration of the prosthetic femoral component. The inside surface of the rail member matches the outside dimensions of the prosthetic femoral component. Accordingly, the surgeon is able to template prior to bone removal. A controlled depth of resurfacing is achieved with the present invention while preventing over and under cutting with about 3 mm of bone typically being removed from the distal aspect of the condyle. The tissue removing members do not have to be perpendicular to the femoral resurfacing guides to create the controlled depth of resurfacing. The femoral resurfacing guides are advantageously referenced from an anterior-distal stylus that represents the position of the anterior-distal aspect of the femoral component. Femoral resurfacing guides having different medial-lateral angles relative to the resection slot of the posterior resection block may be provided. Resurfacing may be accomplished with the femoral resurfacing guides by resurfacing one continuous, unbroken delineated area or by resurfacing a plurality of delineated area segments. The resurfacing guides may be used to resurface the posterior aspect of the femoral condyle as well as the distal aspect. A significant area of contact is maintained between the implanted prosthetic femoral and tibial components, and the contact is maintained as the knee goes from extension into flexion without edge loading and abnormal stresses. The implanted prosthetic femoral component follows the normal tracking line of the femur, which starts a little lateral on the prosthetic femoral component and tracks medially and posteriorly as the knee goes from extension into flexion.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of surgically preparing a femoral condyle to receive a prosthetic femoral component in a minimally invasive unicompartmental knee replacement procedure, comprising the steps of accessing a knee through a minimal incision; positioning a femoral resurfacing guide on a femoral condyle of the knee to externally delineate an area of the femoral condyle to be resurfaced to receive a prosthetic femoral component, said step of positioning including externally delineating the area with a rail member of the femoral resurfacing guide; and removing anatomical tissue from the externally delineated area by moving a tissue removing instrument along the externally delineated area within the confines of the rail members, wherein said step of removing includes contacting an engagement wall of the tissue removing instrument with an abutment wall of the femoral resurfacing guide to limit removal of anatomical tissue to a predetermined depth, and wherein said step of removing includes accessing the externally delineated area by introducing the tissue removing instrument through a window of a slide movably carried by the rail member and moving the slide along the rail member as the tissue removing instrument is moved along the externally delineated area, and said step of contacting includes contacting the engagement wall with a surface of the slide defining the abutment wall.

2. The method recited in claim 1 wherein said step of removing includes removing anatomical tissue with a rasp.

3. The method recited in claim 1 wherein said step of removing includes removing anatomical tissue with an end mill cutter.

4. The method recited in claim 1 wherein said step of removing includes removing anatomical tissue with a reamer.

5. The method recited in claim 1 wherein said step of removing includes removing anatomical tissue with a burr.

6. The method recited in claim 1 wherein said step of contacting includes contacting the engagement wall with a surface of the rail member defining the abutment wall.

7. A method of surgically preparing a femoral condyle to receive a prosthetic femoral component in a minimally invasive unicompartmental knee replacement procedure, comprising the steps of accessing a knee through a minimal incision; establishing a planar surface on a posterior aspect of a femoral condyle of the knee; positioning a femoral resurfacing guide on the femoral condyle to externally delineate a distal aspect of the femoral condyle; removing anatomical tissue from the externally delineated distal aspect; and removing the femoral resurfacing guide from the femoral condyle, wherein said step of positioning includes externally delineating the distal aspect at least medially, laterally and anteriorly with a rail member of the femoral resurfacing guide, wherein said step of removing anatomical tissue includes moving a tissue removing instrument along the externally delineated distal aspect, wherein said step of removing includes accessing the externally delineated distal aspect by introducing the tissue removing instrument through a window of a slide movably carried by the rail member and moving the slide along the rail member in response to moving the tissue removing member along the externally delineated distal aspect.

8. The method recited in claim 7 wherein said step of removing anatomical tissue includes retaining the anatomic geometry of the externally delineated distal aspect.

9. The method recited in claim 7 wherein said step of removing anatomical tissue includes manually moving the tissue removing instrument along the externally delineated distal aspect.

10. The method recited in claim 7 wherein said step of removing anatomical tissue includes mechanically moving the tissue removing instrument along the externally delineated distal aspect.

11. A method of surgically preparing a femoral condyle to receive a prosthetic femoral component in a minimally invasive unicompartmental knee replacement procedure, comprising the steps of accessing a knee through a minimal incision; positioning a resection block on the femur of the knee with the knee in flexion such that a planar resection slot through the resection block extends in a plane along a posterior aspect of a femoral condyle of the femur; positioning a femoral resurfacing guide on the femoral condyle with the knee in flexion such that the femoral resurfacing guide externally delineates a distal aspect of the femoral condyle; inserting a cutting member through the resection slot to effect a planar surface along the posterior aspect of the femoral condyle; and moving a tissue removing member within the externally delineated distal aspect to effect a resurfaced area along the distal aspect of the femoral condyle merging with the planar surface.

12. The method recited in claim 11 and further including the step of fixating the resection block and the femoral resurfacing guide to the femur subsequent to said steps of positioning and prior to said steps of inserting and moving.

13. The method recited in claim 11 and further including the step of attaching the resection block to the femoral resurfacing guide prior to said steps of positioning.

14. The method recited in claim 11 wherein said steps of positioning the resection block includes inserting a planar tab of an alignment module in the resection slot, aligning a check rod of the alignment module, which extends perpendicular to the tab, parallel to the long axis of the corresponding tibia to establish a position for the resection slot, and withdrawing the tab from the resection slot after proper positioning of the resection block is established.

15. The method recited in claim 14 wherein said step of positioning the resection block is performed with the femoral resurfacing guide assembled with the resection block to form a one-piece construct.

16. The method recited in claim 11 wherein said steps of positioning include inserting an intramedullary rod in the intramedullary canal of the femur, coupling a linking instrument to the resection block by inserting a horizontal linking bar of the linking instrument in a channel of the resection block that extends parallel to the resection slot, and coupling the intramedullary rod to a vertical linking bar of the linking instrument that extends at an angle to the horizontal linking bar such that the vertical linking bar is perpendicular to the intramedullary rod.

17. The method recited in claim 16 wherein said steps of coupling are performed with the femoral resurfacing guide assembled with the resection block to form a one-piece construct.

18. A method of surgically preparing a femoral condyle to receive a prosthetic femoral component in a minimally invasive unicompartmental knee replacement procedure, comprising the steps of:

accessing a knee through a minimal incision;

positioning a femoral resurfacing guide on a femoral condyle of the knee wherein the step of positioning includes defining an open unimpeded space with a rail member of the femoral resurfacing guide, the open unimpeded space corresponding to an implant resurface area to be resurfaced by a resurfacing rasp instrument and wherein the resurfacing rasp instrument can reciprocate upward or downward within the rail member without impingement and without leaving an island of bone in the implant resurface area; and removing anatomical tissue from the implant resurface area by reciprocating a resurfacing rasp instrument within the rail member of the femoral resurfacing guide.

19. The method of claim 18, wherein said step of positioning further includes contacting the femoral condyle with a stylus of the femoral resurfacing guide, the stylus sized and positioned to contact a distal and substantially anterior surface of the femoral condyle during positioning to thereby prevent mal-positioning of the femoral resurfacing guide while maintaining a proper depth of resurfacing.

20. The method of claim 19, wherein the stylus is further positioned to indicate where the prosthetic femoral component will transition into the femoral condyle.

21. The method of claim 18, wherein opposing medial and lateral sidewalls of said resurfacing rasp instrument are sized to closely abut opposing medial and lateral inside surfaces of said rail member of said femoral resurfacing guide to thereby guide said resurfacing rasp instrument during reciprocation.

22. The method of claim 18, wherein a lower surface of a ledge of the resurfacing rasp instrument is maintained above or atop an anterior surface of the rail member as the resurfacing rasp instrument is reciprocated along the implant resurface area, whereby abutment between said lower surface of the ledge of the resurfacing rasp instrument and the anterior surface of the rail member provides a stop to ensure that the articular surface of the femur is removed to a predetermined depth.

23. The method of claim 22, further comprising determining completion of said step of resurfacing by assessing when a side wall of the resurfacing rasp instrument contacts an inside surface of the rail member and when the lower surface of the ledge of the resurfacing rasp instrument contacts the anterior surface of the rail member along the resurfacing rasp instrument's entire path of travel along the implant resurface area to thereby obtain a smooth, curved, resurfaced area on the distal aspect of the femoral condyle.

24. The method of claim 18, further comprising directing the femoral resurfacing instrument in an upward direction to complete resurfacing of the femur at an anterior-most portion of the femoral resurfacing guide.

25. A method of surgically preparing a femoral condyle to receive a prosthetic femoral component in a minimally invasive unicompartmental knee replacement procedure, comprising the steps of:

accessing a knee through a minimal incision;

positioning a femoral resurfacing guide on a femoral condyle of the knee wherein the step of positioning includes defining an open unimpeded space with a rail member of the femoral resurfacing guide, the open unimpeded space corresponding to an implant resurface area to be resurfaced by an end mill cutter and wherein the end mill cutter can remove anatomical tissue from the femoral condyle throughout the implant resurface area without leaving an island of bone in the implant resurface area; and removing anatomical tissue from the implant resurface area by moving an end mill cutter within the rail member of the femoral resurfacing guide throughout the implant resurface area.

26. The method of claim 25, wherein said step of positioning further includes contacting the femoral condyle with a stylus of the femoral resurfacing guide, the stylus sized and positioned to contact a distal and substantially anterior surface of the femoral condyle during positioning to thereby prevent mal-positioning of the femoral resurfacing guide while maintaining a proper depth of resurfacing.

27. The method of claim 26, wherein the stylus is further positioned to indicate where the prosthetic femoral component will transition into the femoral condyle.

28. The method of claim 18, wherein a lower surface of a ledge of the end mill cutter is maintained above or atop an anterior surface of the rail member as the end mill cutter is reciprocated along the implant resurface area, whereby abutment between said lower surface of the ledge of the end mill cutter and the anterior surface of the rail member provides a stop to ensure that the articular surface of the femur is removed to a predetermined depth.

29. The method of claim 22, further comprising determining completion of said step of resurfacing by assessing when a side wall of the end mill cutter contacts an inside surface of the rail member and when the lower surface of the ledge of the end mill cutter contacts the anterior surface of the rail member along the end mill cutter's entire path of travel along the implant resurface area to thereby obtain a smooth, curved, resurfaced area on the distal aspect of the femoral condyle.

* * * * *